US012090148B2

(12) United States Patent
Trugman et al.

(10) Patent No.: US 12,090,148 B2
(45) Date of Patent: Sep. 17, 2024

(54) TREATMENT OF MIGRAINE

(71) Applicant: Allergan Pharmaceuticals International Limited, Dublin (IE)

(72) Inventors: Joel Trugman, Hoboken, NJ (US); Michelle Finnegan, Brooklyn, NY (US)

(73) Assignee: Allergan Pharmaceuticals International Limited, Dublin (IE)

( * ) Notice: Subject to any disclaimer, the term of this patent is extended or adjusted under 35 U.S.C. 154(b) by 0 days.

(21) Appl. No.: 17/389,223

(22) Filed: Jul. 29, 2021

(65) Prior Publication Data

US 2022/0031686 A1 Feb. 3, 2022

Related U.S. Application Data

(60) Provisional application No. 63/201,254, filed on Apr. 20, 2021, provisional application No. 63/129,362, filed on Dec. 22, 2020, provisional application No. 63/092,211, filed on Oct. 15, 2020, provisional application No. 63/087,175, filed on Oct. 2, 2020, provisional application No. 63/070,449, filed on Aug. 26, 2020, provisional application No. 63/103,353, filed on Jul. 29, 2020.

(51) Int. Cl.
A61K 31/4545 (2006.01)
A61P 25/06 (2006.01)

(52) U.S. Cl.
CPC .......... *A61K 31/4545* (2013.01); *A61P 25/06* (2018.01)

(58) Field of Classification Search
CPC .............................. A61K 31/4545; A61P 25/06
See application file for complete search history.

(56) References Cited

U.S. PATENT DOCUMENTS

| | | | |
|---|---|---|---|
| 4,166,452 A | 9/1979 | Generales, Jr. |
| 4,256,108 A | 3/1981 | Theeuwes |
| 4,265,874 A | 5/1981 | Bonsen et al. |
| 7,205,293 B2 | 4/2007 | Bell et al. |
| 7,390,798 B2 | 6/2008 | Williams et al. |
| 7,629,338 B2 | 12/2009 | Wood |
| 7,893,079 B2 | 2/2011 | Wood et al. |
| 8,481,556 B2 | 7/2013 | Bell et al. |
| 8,754,096 B2 | 6/2014 | Bell et al. |
| 8,883,807 B2 | 11/2014 | Bell et al. |
| 8,895,572 B2 | 11/2014 | Burgey et al. |
| 8,912,210 B2 | 12/2014 | Bell et al. |
| 9,067,941 B2 | 6/2015 | Burgey et al. |
| 9,109,209 B2 | 8/2015 | Cabirol et al. |
| 9,174,989 B2 | 11/2015 | Chen et al. |
| 9,227,972 B2 | 1/2016 | Bell et al. |
| 9,227,973 B2 | 1/2016 | Bell et al. |
| 9,296,750 B2 | 3/2016 | Bell et al. |
| 9,376,431 B2 | 6/2016 | Xiang et al. |
| 9,409,916 B2 | 8/2016 | Bell et al. |
| 9,487,523 B2 | 11/2016 | Belyk et al. |
| 9,499,541 B2 | 11/2016 | Bell et al. |
| 9,499,545 B2 | 11/2016 | Bell et al. |
| 9,624,478 B2 | 4/2017 | Cabirol et al. |
| 9,833,448 B2 | 12/2017 | Bell et al. |
| 9,833,488 B2 | 12/2017 | Buyuktimkin et al. |
| 9,850,246 B2 | 12/2017 | Chen et al. |
| 10,106,541 B2 | 10/2018 | Chen et al. |
| 10,117,836 B2 | 11/2018 | Johnson et al. |
| 10,117,936 B2 | 11/2018 | Nebuloni et al. |
| 10,272,077 B2 | 4/2019 | Bell et al. |
| 11,717,515 B2 | 8/2023 | Trugman et al. |
| 11,857,542 B2 | 1/2024 | Trugman et al. |
| 11,925,709 B2 | 3/2024 | Johnson et al. |
| 2004/0076668 A1 | 4/2004 | Berchielli et al. |
| 2005/0196439 A1 | 9/2005 | Sherwood et al. |
| 2010/0179166 A1 | 7/2010 | Bell et al. |
| 2010/0227903 A1 | 9/2010 | Geers et al. |
| 2012/0122899 A1 | 5/2012 | Bell et al. |
| 2012/0122900 A1 | 5/2012 | Bell et al. |
| 2012/0122911 A1 | 5/2012 | Bell et al. |
| 2015/0023888 A1 | 1/2015 | Cook et al. |
| 2016/0051561 A1 | 2/2016 | Etter |
| 2016/0220552 A1 | 8/2016 | Mahjour et al. |
| 2016/0346214 A1 | 12/2016 | Johnson et al. |
| 2017/0189443 A1 | 7/2017 | Parsons |
| 2018/0008576 A1 | 1/2018 | Kleideiter et al. |
| 2018/0092899 A1 | 4/2018 | Liu et al. |
| 2018/0127417 A1 | 5/2018 | Chen et al. |
| 2019/0070161 A1 | 3/2019 | Mahjour et al. |
| 2019/0085061 A1 | 3/2019 | Burstein |

(Continued)

FOREIGN PATENT DOCUMENTS

| | | | |
|---|---|---|---|
| CN | 101018781 A | 8/2007 |
| CN | 101208303 A | 6/2008 |

(Continued)

OTHER PUBLICATIONS

Bell et al., MEDI 20: Discovery of AGN-241689: A potent, orally-acting CGRP receptor antagonist for migraine prophylaxis, 253 American Chemical Society, Abstracts, p. 20 (Apr. 2-6, 2017) (Year: 2017).*

Allergan PLC., "Allergan Outlines Open Science Model and Highlights Key Development Programs at R&D Day," Press Release. Nov. 2015, 5 pages. [Retrieved from the Internet] URL: http://www.multivu.com/players/English/7671931-allergan-r-d-day/.

American Headache Society., "Clinical Data Presented at American Headache Society Meeting Shows Promise of New Treatments for Migraine Prevention," Press Release, Jun. 2016, 5 pages. [Retrieved from the Internet] URL: https://americanheadachesociety.org/news/clinical-data-presented-at-american-headache-society-meeting-shows-promise-of-new-treatments-for-migraine-prevention/.

Ansel C.H., et al., "Pharmaceutical Dosage Forms and Drug Delivery Systems", 7th Edition, Lippincott Williams & Wilkins, 1999, pp. 367-369.

(Continued)

*Primary Examiner* — Timothy R Rozof
(74) *Attorney, Agent, or Firm* — Foley Hoag LLP; Hathaway P. Russell; Benjamin A. Vaughan

(57) ABSTRACT

The present disclosure provides methods for the treatment of migraine by the administration of atogepant or a pharmaceutically acceptable salt thereof.

10 Claims, 37 Drawing Sheets

(56) References Cited

U.S. PATENT DOCUMENTS

| | | |
|---|---|---|
| 2019/0135927 A1 | 5/2019 | Levin |
| 2019/0209478 A1 | 7/2019 | Johnson et al. |
| 2019/0374518 A1 | 12/2019 | Trugman et al. |
| 2020/0383983 A1 | 12/2020 | Brin et al. |
| 2021/0085612 A1 | 3/2021 | Johnson et al. |
| 2021/0379029 A1 | 12/2021 | Trugman et al. |
| 2022/0031686 A1 | 2/2022 | Trugman et al. |
| 2022/0193051 A1 | 6/2022 | Trugman et al. |
| 2022/0340650 A1 | 10/2022 | Jakate et al. |
| 2023/0130736 A1 | 4/2023 | Boinpally et al. |
| 2023/0158128 A1 | 5/2023 | Brin et al. |
| 2023/0248655 A1 | 8/2023 | Johnson et al. |
| 2023/0248715 A1 | 8/2023 | Liu et al. |
| 2023/0321055 A1 | 10/2023 | Trugman et al. |
| 2023/0330072 A1 | 10/2023 | Trugman et al. |

FOREIGN PATENT DOCUMENTS

| | | |
|---|---|---|
| CN | 101448821 B | 3/2013 |
| JP | 2008/512480 A | 4/2008 |
| JP | 2008/512481 A | 4/2008 |
| JP | 2010/529119 A | 8/2010 |
| JP | 2011/504481 A | 2/2011 |
| JP | 2012/528827 A | 11/2012 |
| KR | 10-2013-0087037 A | 8/2013 |
| RU | 2216317 C2 | 11/2003 |
| WO | WO-2004/082602 A2 | 9/2004 |
| WO | WO-2004/092166 A2 | 10/2004 |
| WO | WO-2004/092168 A1 | 10/2004 |
| WO | WO-2006/031606 A2 | 3/2006 |
| WO | WO-2006/031610 A2 | 3/2006 |
| WO | WO-2006/069754 A1 | 7/2006 |
| WO | WO-2007/092642 A2 | 8/2007 |
| WO | WO-2007/133491 A1 | 11/2007 |
| WO | WO-2008/153849 A1 | 12/2008 |
| WO | WO-2009/050234 A1 | 4/2009 |
| WO | WO-2009/065922 A2 | 5/2009 |
| WO | WO-2009/100090 A1 | 8/2009 |
| WO | WO-2009/126530 A2 | 10/2009 |
| WO | WO-2010/114801 A1 | 10/2010 |
| WO | WO-2010/139717 A1 | 12/2010 |
| WO | WO-2011/156578 A1 | 12/2011 |
| WO | WO-2012/064910 A1 | 5/2012 |
| WO | WO-2012/121758 A1 | 9/2012 |
| WO | WO-2012/122279 A1 | 9/2012 |
| WO | WO-2015/038736 A2 | 3/2015 |
| WO | WO-2015/119848 A1 | 8/2015 |
| WO | WO-2015/120014 A1 | 8/2015 |
| WO | WO-2017/051385 A1 | 3/2017 |
| WO | WO-2019/050759 A1 | 3/2019 |
| WO | WO-2019/087161 A1 | 5/2019 |
| WO | WO-2019/234709 A1 | 12/2019 |
| WO | WO-2020/051137 A1 | 3/2020 |
| WO | WO-2020/150703 A1 | 7/2020 |
| WO | WO-2020/214906 A1 | 10/2020 |
| WO | WO-2021/062282 A1 | 4/2021 |
| WO | WO-2022/140537 A1 | 6/2022 |
| WO | WO-2023/049920 A1 | 3/2023 |
| WO | WO-2023/173005 A3 | 11/2023 |

OTHER PUBLICATIONS

Bagley C.L., et al., "Validating Migraine-Specific Quality of Life Questionnaire v2.1 in Episodic and Chronic Migraine," Headache, Mar. 2012; vol. 5 2(3): pp. 409-421.

Bigal M.E., et al., "Body mass index and episodic headaches: a population-based study," Archives of internal medicine, Oct. 2007, vol. 167 (18), pp. 1964-1970.

Bigal M.E., et al., "Obesity and migraine: a population study," Neurology, 2006, vol. 66(4), pp. 545-550.

Cala M.L., et al., "The Activity Impairment in Migraine Diary (AIM-D): A novel migraine-specific patient-reported outcome measure to assess functioning based on activity impairment in episodic and chronic migraine patients", MTIS2018-005, Cephalalgia, 2018, vol. 38, pp. 1-115.

Clinical Trial: 12-Week Placebo-controlled Study of Atogepant for the Preventive Treatment of Migraine in Participants With Episodic Migraine, https://www.clinicaltrials.gov/ct2/show/NCT03777059 (2018).

Clinical Trial: Efficacy, Safety, and Tolerability of Multiple Dosing Regimens of Oral Atogepant (AGN-241689) in Episodic Migraine Prevention, https://clinicaltrials.gov/ct2/show/NCT02848326 (2016).

Clinical Trial: Study to Evaluate the Safety and Tolerability of Treatment With Atogepant 60 mg Daily for the Prevention of Migraine in Participants With Episodic Migraine, https://clinicaltrials.gov/ct2/show/NCT03700320.

Edvinsson L. et al., "Neuropeptides in Migraine and Cluster Headache Review Article", Cephalalgia, Oct. 14, 1994 (Oct. 14, 1994), pp. 320-327, XP055542226.

Gelaye B., et al., "Body composition status and the risk of migraine: a meta-analysis," Neurology, May 2017, vol. 88 (19), pp. 1795-1804.

Gennaro Alfonso R., "Remington: The Science and Practice of Pharmacy", 2000, 20th edition, Table of Contents.

Global Health Metrics, "Global burden of 369 diseases and injuries in 204 countries and territories, 1990-2019: a systematic analysis for the Global Burden of Disease Study 2019", The Lancet, 396 (10258), pp. 1204-1222.

Goodman & Gilman's The Pharmacological Basis of Therapeutics, Joel G. Hardman et al., eds., McGraw-Hill Professional, 10th ed. 2001, Table of Contents.

Ho T.W., et al., "Randomized Controlled Trial of an Oral CGRP Receptor Antagonist, MK-0974, in Acute Treatment of Migraine", Neurology, Apr. 2008, vol. 70(16), pp. 1304-1312.

Ho T.W., et al., "Randomized Controlled Trial of the CGRP Receptor Antagonist Telcagepant for Migraine Prevention", Neurology, Sep. 2014, vol. 83(11), pp. 958-966.

Ho T.W., et al., "Randomized Controlled Trial of the CGRP Receptor Antagonist Telcagepant for Prevention of Headache in Women with Perimenstrual Migraine", Cephalalgia, Feb. 2016, vol. 36(2), pp. 148-161.

Holland P.R., and Goadsby P.J., "Targeted CGRP Small Molecule Antagonists for Acute Migraine Therapy," Neurotherapeutics, Apr. 2018, vol. 15 (2), pp. 304-312.

International Search Report and Written Opinion for Application No. PCT/IB2019/054781, dated Oct. 22, 2019, 10 pages.

Kasarala G et al., "Standard Liver Tests," Clinical Liver Disease, Jul. 2016, vol. 8 (1), pp. 13-18.

Kristoffersen E.S., et al., "Migraine, Obesity, and Body Fat Distribution—a Population-Based Study," The journal of headache and pain, Aug. 2020, vol. 21 (1), pp. 97.

Lars Edvinsson: "CGRP as the target of new migraine therapies—successful translation from bench to clinic", Nature Reviews, Apr. 24, 2018 (Apr. 24, 2018). XP055476796.

Merck, B.I. and Co Inc Harleysville PA USA et al: "Discovery of AGN-241689: A potent, orally-acting CGRP receptor antagonist for migraine prophylaxis", Abstracts of Papers, ACS National Meeting & Exposition; 253rd National Meeting of the American-Chemical-Society (ACS) on Advanced Materials, Technologies, Systems, and Processes; San Francisco, CA, USA, Apr. 2-6, 2017. American Chemical Society, vol. 253. Apr. 2, 2017 (Apr. 2, 2017). p. 20. XP009516497.

Messina R., et al., "CGRP—A Target for Acute Therapy in Migraine: Clinical Data," Cephalalgia, An International Journal of Headache, 2019, vol. 39(3), pp. 420-427.

Negro A., et al., "CGRP Receptor Antagonists: An Expanding Drug Class for Acute Migraine?," Expert Opinion on Investigational Drugs, 2012, vol. 21(6), pp. 807-818.

Neuschwander-Tetri B.A et al., "The upper limits of normal for serum ALT levels reported by clinical laboratories depend on local reference populations," Arch Intern Med., Mar. 2004, vol. 168(6), pp. 663-666.

Ornello R., et al., "Migraine and body mass index categories: a systematic review and meta-analysis of observational studies," The journal of headache and pain, Mar. 2015, vol. 16 (1), 14 pgs.

(56) References Cited

OTHER PUBLICATIONS

Peterlin B.L., et al., "Obesity and migraine: the effect of age, gender and adipose tissue distribution," Headache, Jan. 2010, vol. 50 (1), pp. 52-62.
Remington J.P "Remington's Pharmaceutical Sciences," 17th Edition Edited by Alfonso R. Gennaro, Mack Publishing Co, Journal of Pharmaceutical Science, 1985, vol. 74 (10).
Rowe R.C., et al., "Handbook of Pharmaceutical Excipients," APhA Publications, 4th edition, 2003. pp.1-6.
Scher A.I., et al., "Factors associated with the onset and remission of chronic daily headache in a population-based study, " Pain, Nov. 2003, vol. 106 (1-2), pp. 81-89.
Silberstein S.D., et al., "Pharmacologic treatment for episodic migraine prevention in adult," American Academy of Neurology, Apr. 2012, vol. 78 (17), pp. 1337-1345.
Winter A.C. "Body mass index, migraine, migraine frequency and migraine features in women," Cephalalgia, Feb. 2009, vol. 29(2), pp. 269-278.
Yang M., et al., "Validation of the Headache Impact Test (HIT-6™) Across Episodic and Chronic Migraine," Cephalalgia, Feb. 2011; vol. 31(3), pp. 357-367.
"Pharmacokinetics in Patients with Impaired Hepatic Function: Study Design, Data Analysis, and Impact on Dosing and Labeling," U.S. Food and Drug Administration (2003).
60th Annual Scientific Meeting, American Headache Society, 60th Annual Scientific Meeting American Headache Society, AHS 2018. San Francisco, CA, United States. Jun. 28-Jul. 1, 2018.
Anonymous: "Highlights of Prescribing Information: Qulipta", retreived online via <https://www.rxabbvie.com/pdf/qulipta_pi.pdf> (2021).
Anonymous: "Highlights of Prescribing Information: Ubrelvy (ubrogepant) tablets," retrieved online via <https://www.rxabbvie.com/pdf/ubrelvY-P i.pdf> (2021).
Armstrong., "Biohaven hopes to give Allergan a headache," Evaluate Vantage, retrieved online <https://www.evaluate.com/vantage/articles/interviews/biohaven-hopes-give-allergan-headache>: 3 pages (2018).
Arulmozhi et al., "Migraine: Current concepts and emerging therapies", Vascular Pharmacology, 43: 176-187 (2005).
Ashina et al. "Plasma levels of calcitonin gene-related peptide in chronic tension-type headache," Neurology 55.9: 1335-1340. (2000).
Awawdeh et al. "Quantitative analysis of substance P, neurokinin A and calcitonin gene related peptide in pulp tissue from painful and healthy human teeth," International endodontic Journal 35.1 : 30-36 (2002).
Barbanti et al., "The role of anti-CGRP antibodies in the pathophysiology of primary headaches," Neurol Sci 38 (Suppl. 1): pp. S31-S35 (2017).
Beer et al. "Systemic neuropeptide levels as predictive indicators for lethal outcome in patients with postoperative sepsis," Critical care medicine 30.8 : 1794-1798 (2002).
Belikov., "Pharmaceutical Chemistry," M. High School: 6 pages (1993).
Bellamy et al. "Salivary levels of CGRP and VIP in rhinosinusitis and migraine patients," Headache: The Journal of Head and Face Pain 46.1 : 24-33(2006).
Bennet et al. "Alleviation of mechanical and thermal allodynia by CGRP8-37 in a rodent model of chronic central pain," Pain 86.1-2 : 163-175 (2000).
Boinpally et al., "63rd Annual Scientific Meeting American Headache Society: Evaluation of the pharmacokinetic interaction and safety of atogepant coadministered with esomeprazole magnesium", Headache 61(S1): pp. 1-178 (2021).
Boinpally et al., "Single-Dose Pharmacokinetics and Safety of Atogepant in Adults With Hepatic Impairment: Results From an Open-Label, Phase 1 Trial," Clinical Pharmacology in Drug Development 10(7): pp. 726-733 (2021).
Boinpally et al., "Single-Dose Pharmacokinetics and Safety of Ubrogepant in Adults With Hepatic Impairment: Results From an Open-Label, Phase 1 Trial," Clinical Pharmacology in Drug Development, 0(0): 1-8 (2022).

Brauser, D., "Phase 3 Strive and Arise Trials Show Efficacy, Safety for Erenumab in Migraine Prevention," Medscape Medical News, 2017.
Burstein et al. "An association between migraine and cutaneous allodynia," Annals of neurology 47.5 614-624. (2000).
Cady et al. "Elevated saliva calcitonin gene-related peptide levels during acute migraine predict therapeutic response to rizatriptan," Headache: The Journal of Head and Face Pain 49.9: 1258-1266. (2009).
Chedid et al., "Hepatocellular Carcinoma: Diagnosis and Operative Management," ABCD Arq Bras Cir Dig 30(4): pp. 272-278 (2017).
Chen et al. "Menopausal flushes and calcitonin-gene-related peptide," The Lancet 342.8862:p. 49.(1993).
Cheng et al. "The concentration of inhibitor which causes 50 percent inhibition (I) of an enzymatic reaction," Biochem. Pharmacol 22 : 3099-3108 (1973).
Cho et al. "Development of Novel Fast-Dissolving Tacrolimus Solid Dispersion-Loaded Prolonged Release Tablet". European Journal of Pharmaceutical Sciences. Jan. 2014 [Online], 4:1-7. (Year: 2014).
Clinical Trial NCT02828020: Efficacy, Safety, and Tolerability Study of Oral Ubrogepant in the Acute Treatment of Migraine (ACHIEVE I), https://clinicaltrials.gov/ct2/history/NCT02828020?V_1=View#StudyPageTop (2016).
Clinical Trial NCT02867709: Efficacy, Safety, and Tolerability of Oral Ubrogepant in the Acute Treatment of Migraine (ACHIEVE II), https://clinicaltrials.gov/ct2/show/results/NCT02867709 (2016).
Connor et al., "Randomized, controlled trial of telcagepant for the acute treatment of migraine", Neurology, 2009, pp. 970-977, 73.
Dahlof CGH. "Infrequent or non-response to oral sumatriptan does not predict response to other triptans—review of four trials," Cephalagia, Feb. 2006, vol. 26 (2), pp. 98-106.
Deen et al. "Blocking CGRP in migraine patients—a review of pros and cons," The Journal of Headache and Pain 18(96): 9 pages (2017).
Delay-Goyet et al. "Relative involvement oi substance P and CGRP mechanisms in antidromic vasodilation in the rat skin," Acta physiologica scandinavica 146.4 : 537-538.(1992).
Do et al., "Therapeutic novelties in migraine: new drugs, new hope?," The Journal of Headache and Pain, 20: Article 37 pp. 1-13 (2019).
Doods "Development of CGRP antagonists for the treatment of migraine," Current opinion in investigational Drugs 2.9: 1261-1268. (2001).
Doods et al. "Pharmacological profile of BIBN4096BS, the first selective small molecule CGRP antaaonist," British Journal of Pharmacology 29.3 : 420-423. (2000).
Edvinsson et al. "Characterization of the effects of a non-peptide CGRP receptor antagonist in SK-N-MC cells and isolated human cerebral arteries," European journal of pharmacology 415. : 39-44. (2001).
Edvinsson et al. "Neuropeptides in migraine and cluster headache," Cephalalgia 14.5 : 320- 327 (1994).
Edvinsson et al., "Basic mechanisms of migraine and its acute treatment", Pharmacology and Therapeutics, 136: 319-333 (2012).
Escott et al. "Trigeminal ganglion stimulation increases facial skin blood flow in the rat: a major role for calcitonin gene-related peptide," Brain research 669.i : 93-99 (1995).
Evans et al. "The asymmetric synthesis of. alpha.-amino acids. Electrophilic azidation of chiralimide enolates, a practical approach to the syntheses of (R) and (S)-alpha azido carboxylic acids," Journal of the American Chemical Society 112.10 : 4011-4030. (1990).
Foster et al. "Calcitonin gene-related peptide is chemotactic for human T lymphocytes," Annals of the New York Academy of Sciences 657.1 : 397-404. (1992).
Friesen et al., "Hydroxypropyl Methylcellulose Acetate Succinate-Based Spray-Dried Dispersions: An Overview," Molecular Pharmaceutics, 5(6): 1003-1019 (2008).
Goadsby et al. "Release of vasoactive peptides in the extracerebral circulation of humans and the cat during activation of the trigerninovascular system," Annals of Neurology: Official Journal of the American Neurological Association and the Child Neurology Society 23.2 : 193-196 (1988).

(56) References Cited

OTHER PUBLICATIONS

Goadsby et al. "Vasoactive peptide release in the extracerebral circulation of humans during migraine headache," Annals of Neurology: Official Journal of the American Neurological Association and the Child Neurology Society 28.2 183-187. (1990).
Goadsby et al., "Safety, tolerability, and efficacy of orally administered atogepant for the prevention of episodic migraine in adults: a double-blind, randomised phase 2b/3 trail" (2020).
Goadsby, "Bench to bedside advances in the 21st century for primary headache disorders: migraine treatments for migraine patients," Brain 139(10): pp. 2571-2577 (2016).
Guo et al., "The Applications of Vitamin E Tpgs in Drug Delivery," European Journal of Pharmaceutical Sciences, 49(2): 175-186 (2013).
Harmon et al. "Reaction of arylsulfonyl azides with N-methylindole," The Journal of Organic Chemistry, 38.1, 11-16 (1973).
Herzog et al. "CGRP receptors in the gerbil spiral modular artery mediate a sustained vasodilation via a transient cAMP-mediated Ca2+-decrease," The Journal of membrane biology 189.3, 225-236. (2002).
Ho et al., "Efficacy and Tolerability of MK-097 (telcagepant), a new oral antagonist of cacitonin gene-related peptide receptor, compared with zoimitriptant for acute migraine; a randomised, placebo-controlled parallel-treatment trial":, vol. 372,pp. 2115-2123, The Lancet, 2008, pp. 2115-2123, 372.
Hoffman et al. "Capsaicin-sensitive nerve fibers induce epithelial cell proliferation, inflammatory cell immigration and transforming growth factor-alpha expression in the rat colonic mucosa in vivo," Scandinavian Journal of Gastroenterology 37.4,414-422: (2002).
Holzer et al. "Job queues and wages," Title Quarterly Journal of Economics 106.3, 739-768: (1991).
Holzer et al., "Evaluation o Sodium Stearyl Fumarate as a Tablet Lubricant," International Journal of Pharmaceutics, 2(3-4): 145-153 (Abstract Only)(1979).
International Preliminary Report on Patentability for Application No. PCT/US2021/043791 dated Nov. 18, 2021.
International Preliminary Report on Patentability for International Application No. PCT/IB2019/054780 dated Dec. 8, 2020.
International Preliminary Report on Patentability for International Application No. PCT/US2015/013672 dated Aug. 9, 2016.
International Preliminary Report on Patentability for International Application No. PCT/US2020/028666 dated Oct. 28, 2021.
International Search Report and Written Opinion for Application No. PCT/IB2019/054780, dated Oct. 28, 2019, 8 pages.
International Search Report and Written Opinion for Application No. PCT/US2022/077061 dated Jan. 4, 2023.
International Search Report and Written Opinion for International Application No. PCT/US2020/028666 dated Aug. 28, 2020.
International Search Report and Written Opinion for International Application No. PCT/US2020/052891 dated Feb. 17, 2021.
International Search Report and Written Opinion for International Application No. PCT/US2021/064853 dated Mar. 18, 2022.
International Search Report and Written Opinion of the International Searching Authority Application No. PCT/US15/13672 dated Apr. 21, 2015.
International Search Report with Written Opinion corresponding to International Patent Application No. PCT/US2011/060081, dated Dec. 19, 2011.
Jakate et al., "Effects of CYP3A4 and P-glycoprotein inhibition or induction on the pharmacokinetics of ubrogepant in healthy adults: Two phase 1, open-label, fixed-sequence, single-center, crossover trials," Cephalalgia Reports, 4: 1-10 (2021).
Johnson et al., "A pharmacogenomic evaluation of migraine therapy", Expert Opinion on Pharmacotherapy, 8: 1821-1835 (2007).
Kibbe, "Handbook of Pharmaceuticals Excipients", 2000, Pharmaceutical Press, XP002773202, p. 386.
Kopruszinski et al., "Prevention of stress- or nitric oxide donor-induced medication overuse headache by a calcitonin gene-related peptide antibody in rodents," Cephalalgia, 37(6): 560-570 (2017).
Lance "Headache Pathogenesis: Monoarnines," Neuropeptides, Purines & Nitric Oxide 3-9 (1997).

Lassen et al. "CGRP may play a causative role in migraine," Cephalalgia 22.1 (2002): 54-61.
Late-Breaking Abstracts: 60th Annual Scientific Meeting, American Headache Society, 60th Annual Scientific Meeting American Headache Society, AHS 2018. San Francisco, CA, United States. Jun. 28-Jul. 1, 2018.
Li et al. "Effect of CGRP receptor antagonist CGRP8-37 on nociceptive response, NOS expression and NO content in the dorsal horn of spinal cord during formalin-induced inflammatory pain in rats," Chinese Journal of Applied Physiology. 20(3): 291-295. (2004).
Lipton R.B, et al., "Impact of NSAID and Triptan Use on Developing Chronic Migraine: Results from the American Migraine Prevalence and Prevention (AMPP) Study," Headache, Nov./Dec. 2013, vol. 53 (10), pp. 1548-1563.
Magellan RX Management, Ubrogepant (Ubrelvy™) New Drug Update; retrieved online <https://www.hhs.texas.gov/sites/default/files/documents/about-hhs/communications-events/meetings-events/dur/may-2020/may-2020-durb-agenda-item-5c.pdf>: 8 pages (2020).
May et al. "Intractable eye pain: indication for triotans," Cephalalgia 22.3, 195-196:(2002).
Menard et al. "A calcitonin gene-related peptide receptor antagonist prevents the development of tolerance to spinal morphine analgesia," Journal of Neuroscience 16. 7, 2342-2351 (1996).
Messali A.J., et al., "Treatment persistence and switching in triptan users: a systematic literature review," Headache, Jul.-Aug. 2014, vol. 54 (7), pp. 1120-1130.
Molina et al. "Induction of Insulin Resistance In Vivo by Amylin and Calcitonin Gene-Related Peptide," Diabetes 39.2, 260-265 (1990).
National Center for Biotechnology Information ""Homo sapiens mRNA encoding RAMP1 ,"" GenBank Accession No. AJ001014, 2 pages, (2008).
National Center for Biotechnology Information "Homo sapiens (clone HSNME29) CGRP type 1 receptor mRNA, complete ends," GenBank Accession No. L76380,2 pages, (1996).
Negro A., et al., "Serotonin receptor agonists in the acute treatment of migraine: a review on their therapeutic potential," Journal of Pain Research, Mar. 2018, vol. 11, pp. 515-526.
Olesen et al. "Calcitonin gene-related peptide receptor antagonist BIBN 4096 BS for the acute treatment of migraine," New England Journal of Medicine 350.11, 1104-1110. (2004).
Petersen et al. "BIBN4096BS Antagonizes Human a-calcitonin Gene Related Peptide-C35 induced Headache and Extracerebral Artery Dilatation," Clinical Pharmacology & Therapeutics 77.3 :202-213.(2005).
Pitt et al., "Determination of the Tensile Strength of Elongated Tablets," Powder Technology, 238: 169-175 (2013).
Ramadhani et al. "Preparation and Characterisation of KOL-LIPHOR P188 and P 237 Solid Dispersion Oral Tablets Containing the Poorly Water Soluble DrugDisulfiram". International Journal of Pharmaceutics. Sep. 2014 [Online], 475:514-522. (Year: 2014).
Remington, "The Science and Practice of Pharmacy", 2000, Lippincott Williams&Wilkins, XP002773203. pp. 861-862.
Repka et al., "Melt Extrusion: Process to Product," Expert Opinion on Durg Delivery, Dec. 6, 2011, 9(1): 105-125.
Rohrenbeck et al. "Upregulation of COX-2 and CGRP expression in resident cells of the C36 Borna disease virus-infected brain is dependent upon inflammation," Neurobiology of disease 6.1 : 15-34.(1999).
Rowe et al., "Handbook of Pharmaceutical Excipients", 2000, Pharmaceutical Press, XP002773225, p. 201.
Russo., "CGRP-Based Migraine Therapeutics: How Might They Work, Why So Safe, and What Next?," ACS Pharmacology & Translational Science, 2(1): 2-8 (2019).
Salmon et al. "Altered neuroadaptation in opiate dependence and neurogenic inflammatory nociceotion in aCGRP-deficient mice," Nature neuroscience 4.4, : 357-358. (2001).
Saunders , B., "Allergan 2015 R&D Day", (Nov. 5, 2015), Powerpoint Presentation, slide 1-3 and 49-51. (Allergan plc, 2015).
Schini-Kerth et al. "CGRP enhances induction of NO synthase in vascular smooth muscle C38 cells via a cAMP-dependent mecha-

(56) References Cited

OTHER PUBLICATIONS nism," American Journal of Physiology—Heart and Circulatory Physiology 267.6 : 2483-2490 (1994).
Schuster et al., "Calcitonin Gene-Related Peptide-Targeted Therapies for Migraine and Cluster Headache: A Review," Clinical Neuropharmacology, 40(4): 169-174 (2017).
Scott., "Ubrogepant: First Approval," Drugs, 80: 323-328 (2020).
Serrano D., et al., "Effects of Switching Acute Treatment on Disability in Migraine Patients Using Triptans," Headache, Oct. 2013, vol. 53 (9), pp. 1415-1429.
Spetz et al. "Momentary increase in plasma calcitonin gene-related peptide is involved in hot flashes in men treated with castration for carcinoma of the prostate," The Journal of urology 166.5, 1720-1723.(2001).
Szkutnik-Fiedler et al., "Pharmacokinetics, Pharmacodynamics and Drug-Drug Interactions of New Anti-Migraine Drugs-Lasmiditan, Gepants, and Calcitonin-Gene-Related Peptide (CGRP) Receptor Monoclonal Antibodies," Pharmaceutics, 12(12): 1-22 (2020).
Tepper et al., "Erenumab in chronic migraine with medication overuse" Neurology, 92(20): e2309-2320 (2019).
Tepper et al., "Safety and efficacy of erenumab for preventive treatment of chronic migraine: a randomised, double-blind, placebo-controlled phase 2 trial," The Lancet Neurology, 16(6): 425-434 (2017).
Viana M., et al., "Triptan non-responders: do they exist and who are they?," Cephalalgia, Aug. 2013, vol. 33 (11 ), pp. 891-896.
Voss et al., "A phase IIb randomized, double-blind, placebo-controlled trial of ubrogepant for the acute treatment of migraine," Cephalalgia, 36(9): 887-898 (2016).
Walker et al. "Mice lacking the neuropeptide a-calcitonin gene-related peptide are protected against diet-induced obesity," Endocrinology 151.9 : 4257-4269. (2010).
Wallengren "Dual effects of CGRP-antagonist on allergic contact dermatitis in human skin." Contact dermatitis 43.3, : •137-143 (2000).
Williamson et al. ""The CGRP Family: Calcitonin Gene-Related Peptide (CGRP), Amylin, and Adrenomedullin, Landes,"" Bioscience 245-247.(2000).
Williamson et al. "Sumatriptan inhibits neurogenic vasodilation of dural blood vessels in the anaesthetized rat-intravital microscope studies," Cephalalaia 17.4 : 525-531 (1997).
Written Opinion of the International Search Report for PCT/US2011/060081 dated Dec. 19, 2011.
Written Opinion of the International Search Report for PCT/US2011/060081.
Wu et al., "Regulatory perspectives of Type II prodrug development and time-dependent toxicity management: Nonclinical Pharm/Tox analysis and the role of comparative toxicology," Toxicology 236(1-2): pp. 1-6 (2007).
Yu et al. "Effects of calcitonin gene-related peptide-(8-37) on withdrawal responses in rats with inflammation," European journal of pharmacology 347.2-3, 275-282. (1998).
Zhang et al. "Arthritic calcitonin/a calcitonin gene-related peptide knockout mice have reduced nociceptive hypersensitivity," Pain 89.2-3, : 265-273. (2001 ).
Zheng et al. ""Severity of neurological signs and degree of inflammatory lesions in the brains of rats with Borna disease correlate with the induction of nitric oxide synthase,"" Journal of virology 67.10, 5786-5791. (1993).
Ailani et al., "Atogepant for the Preventive Treatment of Migraine" The New England Journal of Medicine, vol. 385, No. 8, pp. 695-706 (2021).
Amerge (naratriptan hydrochloride) tablets, Highlights of Prescribing Information (2016).
Dodick et al., "Ubrogepant for the treatment of migraine", *New England Journal of Medicine* 381.23: 2230-2241 (2019).
Edvinsson et al., "CGRP as the target of new migrainetherapies—successful translation from bench to clinic", Nature Reviews, 14: 338-350 (2018).
Imitrex (sumatriptan) tablets, Highlights of Prescribing Information.
International Search Report and Wirtten Opinion for Application No. PCT/US2023/064027 dated Sep. 26, 2023.
Lipton et al., "Effect of ubrogepant vs placebo on pain and the most bothersome associated symptom in the acute treatment of migraine: the Achieve II randomized clinical trial." *Jama* 322.19: 1887-1898 (2019).
Mullin et al., "Potential for treatment benefit of small molecule CGRP receptor antagonist plus monoclonal antibody in migraine therapy", Neurology, vol. 94, No. 20, Jan. 13, 2020, pp. e2121-e2125.
Mullin, "Acute treatment benefit from oral CGRP receptor antagonist and monoclonal antibody combination: rimegepant 75mg for acute treatment of attacks during preventive therapy with erenumab", 61st Annual Scientific Meeting American Headache Society, Jun. 1, 2019, pp. 176-177.
Mullin, "Successful gepant-monoclonal antibody combination: Rimegepant 75mg for acute treatment of attacks during preventive therapy with erenumab", Cephalalgia Sep. 1, 2019 Sage Publications Ltd NLD, vol. 39, No. 1, Supplement, Sep. 1, 2019.
Partial EP Search Report for EP Application No. 20869848.0 dated Sep. 21, 2023.
Rapoport et al., "Triptans are all Different", Arch Neurol, 58(9): 1479-1480 (2001).
Reuter, "A Review of Monoclonal Antibody Therapies and Other Preventative Treatments in Migraine", Headache, Woodbury, NJ, United States, vol. 58, Apr. 26, 2018, pp. 48-59.
Schwedt et al., "Time course efficacy of atogepant for the preventive treatment of migraine: Results from the randomized, double-blind Advance trial" Cephalgia, vol. 42, No. 1, p. 3-11 (2022).
Tepper, "CGRP and headache: a brief review", Neurological Sciences (Testo Stampato), Springer Verlag, Milan, IT, vol. 40, No. 1, Mar. 5, 2019, pp. 99-105.
"61st Annual Scientific Meeting", American Headache Society, 208 pages, (Jul. 11-14, 2019).
Ailani et al., "An optional second dose of ubrogepant is effective in achieving 2-hour pain freedom in the acute treatment of migraine (166)", Neurology, 94(15), (2020).
CHMP Guideline, "Guideline on the evaluation of the pharmacokinetics of medicinal products in patients with decreased renal function", European Medicines Agency, 15 pages, (2015).
Curto et al., "Ubrogepant for the treatment of migraine." Expert Opinion on Pharmacotherapy 21(7) (2020): 755-759.
Dodick et al., "Ubrogepant Achieves Onset of Pain Relief at 1 Hour for the Acute Treatment of Migraine (1223)", Neurology, 94(15), (2020).
Dodick et al., "Ubrogepant for the Acute Treatment of Migraine When Administered During the Prodrome (Premonitory Phase): Results From a Phase 3, Randomized, Double-blind, Placebo-Controlled, Crossover Study (S47. 001)." Neurology, (100)17 (2023).
Dos Santos et al., "Small molecule CGRP receptor antagonists for the preventive treatment of migraine: a review." European Journal of Pharmacology 922 (2022): 174902.
Extended European Search Report for EP Application No. 20869848.0 dated Dec. 22, 2023.
Food and Drug Administration, "The Impact of Renal Impairment on Patient Drug Response Assessing the Need for a Consensus Approach", Pharmaceutical Science and Clinical Pharmacology Advisory Committee Meeting, (2019).
Goadsby et al., "Efficacy of Ubrogepant for the Treatment of Migraine Symptoms During the Prodrome (Premonitory Phase): Results From the Prodrome Trial" (2023)., Neurology, [Online] pp. 1-6.
Goadsby et al., "Safety and tolerability of ubrogepant following intermittent, high-frequency dosing: randomized, placebo-controlled trial in healthy adults." Cephalalgia 39.14 (2019): 1753-1761.
Hutchinson et al., "Ubrogepant for the Acute Treatment of Migraine: Pooled Safety and Tolerability From Achieve I and Achieve II Phase 3 Studies (117)", Neurology, 94(15), (2020).
International Search Report and Written Opinion for International Application No. PCT/US23/76576 dated Feb. 23, 2024.

(56) References Cited

OTHER PUBLICATIONS

Kielbasa et al., "A new era for migraine: pharmacokinetic and pharmacodynamic insights into monoclonal antibodies with a focus on galcanezumab, an anti-CGRP antibody", Cephalalgia 39.10: 1284-1297 (2019).

Lipton et al., "Efficacy, safety, and tolerability of rimegepant 75 mg orally dissolving tablet for the acute treatment of migraine: Results from a phase 3, double-blind, randomized, placebo-controlled trial, Study 303", Headache, 59: 21-22 (2019).

McCarthy, "Oral rimegepant increased freedom from pain and from most bothersome symptom at 2 h in acute migraine." Annals of internal medicine 171(10) (2019): JC59.

Medsafe, "Drug Metabolism—The Importance of Cytochrome P450 3A4", retrieved online https://www.medsafe.govt.nz/profs/PUArticles/March2014DrugMetabolismCytochromeP4503A4.htm (2014).

Talal et al., "Assessment of hepatic impairment and implications for pharmacokinetics of substance use treatment", Clinical pharmacology in drug development 6.2: 206-212 (2017).

Yoshida et al. "Systematic and quantitative assessment of the effect of chronic kidney disease on CYP2D6 and CYP3A4/5." Clinical Pharmacology & Therapeutics 100.1 (2016): 75-87.

Yuan et al., "CGRP therapeutics for the treatment of migraine-a narrative review." Ann Head Med 1 (2020): 1-22.

Israel et al., "CGRP Monoclonal Antibodies for the Preventative Treatment of Migraine," Current Pain and Headache Reports 22.5 (2018): 1-6.

Meglio, "Dose-Dependent Weight Reductions Observed With Atogepant", Neurology Live, Jun. 15, 2022.

Supplementary European Search Report for EP Application No. 21850713.5 dated Jun. 26, 2024.

Tepper, "Anti-Calcitonin Gene-Related Peptide (CGRP) Therapies: Update on a Previous Review After the American Headache Society 60th Scientific Meeting, San Francisco, Jun. 2018 11," Headache 58.7 (2018): 276-290.

\* cited by examiner

*P<0.05; P<0.01; *P<0.001
LS, least-squares; mITT, modified intent-to-treat; SE, standard error.
For weekly data, baseline was defined as monthly migraine days/4, and change from baseline in weekly migraine days was to be calculated for consecutive 7-day periods beginning with day 1.

*P<0.05; P<0.01; *P<0.001
mITT, modified intent-to-treat.
a Day of initial dose excluded, as migraine attacks occurring prior to study drug administration were included.

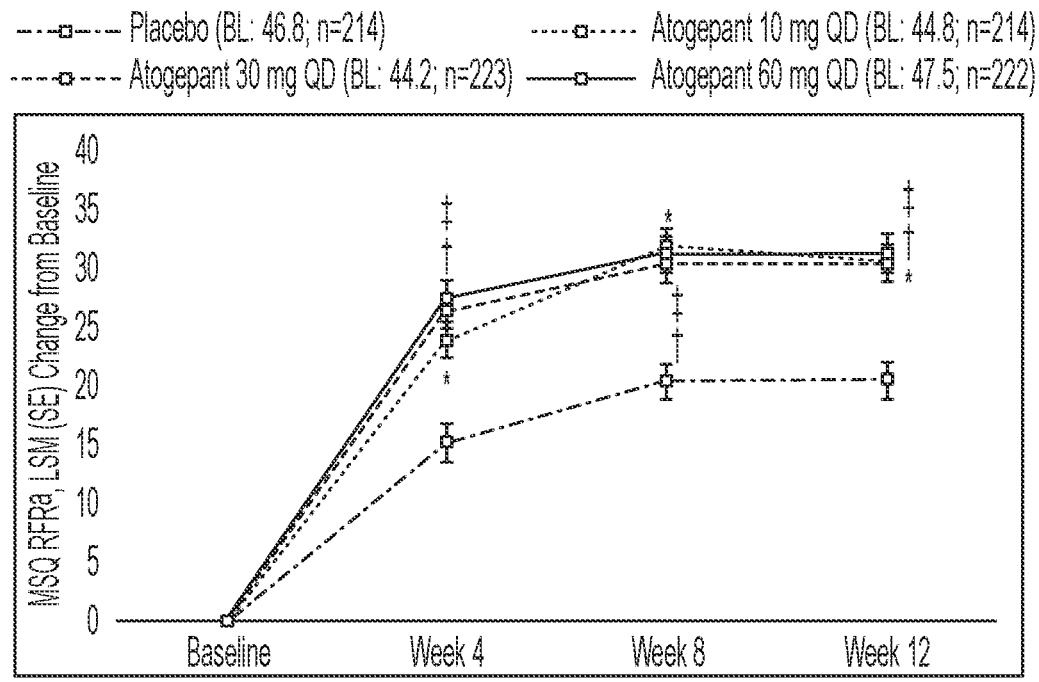

Migraine-Specific Quality of Life Questionnaire Role Function-Restrictive Domain[a] Score: Weeks 4, 8, and 12

BL, baseline mean; LSM, least squares mean; LSMD, least squares mean difference; MSQ, Migraine-Specific Quality of Life Questionnaire; QD, once daily; RFR, Role Function-Restrictive Domain; SE, standard error.
[a] Role Function-Restrictive domain assesses how migraines limit one's daily social and work-related activities. Participants respond to items using a 6-point scale ranging from "none of the time" to "all of the time."
[b] Raw domain scores are rescaled to a 0 to 100 scale, where higher scores indicate better quality of life.
*LSMD (95% CI): Week 4: 8.6 (4.4, 12.9); $P<0.0001$; Week 8: 11.3 (7.1, 15.5); $P<0.0001$; Week 12: 9.9 (5.5, 14.4); $P<0.0001$;
†LSMD (95% CI): Week 4: 11.2 (7.0, 15.4); $P<0.0001$; Week 8: 9.9 (5.8, 14.0); $P<0.0001$; Week 12: 10.1 (5.7, 14.5); $P<0.0001$;
‡LSMD (95% CI): Week 4: 12.3 (8.1, 16.5); $P<0.0001$; Week 8: 10.8 (6.7, 14.9); $P<0.0001$; Week 12: 10.8 (6.4, 15.2); $P<0.0001$.

FIGURE 11

| Weeks | n | LS Mean Δ From Baseline | 95% CI |
|---|---|---|---|
| 1-4 | 397 | -7.61 | -8.26, -6.96 |
| 5-8 | 360 | -8.16 | -8.89, -7.42 |
| 9-12 | 346 | -8.53 | -9.22, -7.84 |
| 13-16 | 334 | -8.66 | -9.37, -7.94 |
| 17-20 | 323 | -9.02 | -9.72, -8.32 |
| 21-24 | 313 | -9.11 | -9.80, -8.43 |
| 25-28 | 301 | -9.16 | -9.88, -8.44 |
| 29-32 | 288 | -9.22 | -9.93, -8.51 |
| 33-36 | 288 | -9.61 | -10.28, -8.94 |
| 37-40 | 283 | -9.61 | -10.27, -8.95 |
| 41-44 | 273 | -9.77 | -10.48, -9.06 |
| 45-48 | 262 | -9.79 | -10.48, -9.10 |
| 49-52 | 247 | -10.17 | -10.90, -9.44 |

FIGURE 16A CONTINUED

| Weeks | n | LS Mean Δ From Baseline | 95% CI |
|---|---|---|---|
| 1-4 | 397 | -5.56 | -6.13,-4.99 |
| 5-8 | 360 | -5.82 | -6.50,-5.13 |
| 9-12 | 346 | -6.13 | -6.75,-5.51 |
| 13-16 | 334 | -6.22 | -6.87,-5.56 |
| 17-20 | 323 | -6.38 | -7.04,-5.73 |
| 21-24 | 313 | -6.43 | -7.08,-5.77 |
| 25-28 | 301 | -6.40 | -7.09,-5.72 |
| 29-32 | 288 | -6.51 | -7.18,-5.84 |
| 33-36 | 288 | -6.94 | -7.57,-6.31 |
| 37-40 | 283 | -6.93 | -7.56,-6.30 |
| 41-44 | 273 | -7.01 | -7.68,-6.34 |
| 45-48 | 262 | -7.02 | -7.68,-6.36 |
| 49-52 | 247 | -7.20 | -7.91,-6.50 |

FIGURE 16B CONTINUED

HIT-6, Headache Impact Test-6; LS, least-squares; mITT, Modified intent-to-treat; SE, standard error.
n=number of participants with evaluable data at both baseline and a specific time point in the mITT population.

| Weeks | n | LS Mean Δ From Baseline | 95% CI |
|---|---|---|---|
| 4 | 514 | -7.63 | -8.31, -6.95 |
| 8 | 491 | -9.14 | -9.87, -8.42 |
| 12 | 471 | -9.60 | -10.33, -8.87 |
| 16 | 448 | -10.15 | -10.93, -9.37 |
| 20 | 442 | -10.56 | -11.35, -9.76 |
| 24 | 423 | -10.55 | -11.39, -9.71 |
| 28 | 418 | -10.99 | -11.83, -10.15 |
| 32 | 407 | -11.15 | -11.98, -10.32 |
| 36 | 402 | -11.29 | -12.14, -10.43 |
| 40 | 394 | -11.76 | -12.60, -10.91 |
| 44 | 384 | -11.46 | -12.32, -10.60 |
| 48 | 377 | -11.86 | -12.72, -10.99 |
| 52 | 364 | -12.10 | -12.98, -11.22 |

FIGURE 18 CONTINUED

TREATMENT OF MIGRAINE

CROSS-REFERENCE TO RELATED APPLICATIONS

The present application claims the benefit of Provisional Application No. 63/103,353, filed Jul. 29, 2020; Provisional Application No. 63/070,449, filed Aug. 26, 2020; Provisional Application 63/087,175, filed Oct. 2, 2020; Provisional Application No. 63/092,211, filed Oct. 15, 2020; Provisional Application No. 63/129,362, filed Dec. 22, 2020; and Provisional Application No. 63/201,254, filed Apr. 20, 2021, the disclosures of which are incorporated herein by reference.

FIELD

The present disclosure is related to medicaments and methods for treating migraine.

BACKGROUND

Migraine is a highly prevalent, severe, and disabling neurological condition with a significant unmet need for effective treatments. (Holland, P. R. & Goadsby, P. J. Neurotherapeutics (2018). Migraine affects over 1 billion people worldwide, and it was reported as the second leading cause of disability in the 2016 Global Burden of Disease study. See GBD 2019 Diseases and Injuries Collaborators. Global Burden of 369 diseases and injuries in 204 countries and territories, 1990-2019: a systemic analysis for the Global Burden of Disease Study 2019, Lancet 2020; 396:1204-22.

When attacks are frequent or disabling, prevention becomes a focus of migraine treatment. Current preventive treatments for migraine include oral medications, such as valproic acid, flunarizine, topiramate, and propranolol, as well as injectable treatments, such as monoclonal antibodies targeting calcitonin gene-related peptide (CGRP).

Currently available CGRP-targeted preventive treatments are limited to monoclonal antibodies, administered by injection. Oral CGRP treatments are approved for acute but not preventive treatment, and yet patients and physicians overwhelmingly prescribe oral migraine preventives, suggesting a treatment gap. There remains a need for optimized and targeted methodologies and dosing regimens to use oral CGRP treatments to prophylactically treat migraines.

SUMMARY

In embodiments, the present disclosure provides methods of prophylactically treating migraine, involving administering atogepant or a pharmaceutically acceptable salt thereof in an amount of 10 mg QD, 30 mg QD, or 60 mg QD, to a patient in need of treatment.

In embodiments, the present disclosure provides methods of prophylactically treating migraine, involving administering atogepant or a pharmaceutically acceptable salt thereof in an amount of 10 mg QD, 30 mg QD, or 60 mg QD, wherein treatment with atogepant results in a reduction in mean monthly migraine days of at least 3.6 days, or at least 3.8 days, or at least 4.2 days, relative to no treatment.

In embodiments, the present disclosure provides a method of prophylactically treating migraine, involving administering atogepant or a pharmaceutically acceptable salt thereof in an amount of 10 mg QD, 30 mg QD, or 60 mg QD, wherein the prophylactic treatment results in a reduction in mean monthly headache days of at least 3.9 days, or at least 4 days, or at least 4.2 days relative to no treatment.

In embodiments, the present disclosure provides a method of prophylactically treating migraine, involving administering atogepant or a pharmaceutically acceptable salt thereof in an amount of 10 mg QD, 30 mg QD, or 60 mg QD, wherein the prophylactic treatment results in a reduction in mean monthly acute medication use days of at least 3.6 days, or at least 3.8 days relative to no treatment.

In embodiments, the present disclosure provides methods of prophylactically treating migraine, involving administering atogepant or a pharmaceutically acceptable salt thereof in an amount of 10 mg QD, 30 mg QD, or 60 mg QD, wherein the prophylactic treatment results in at least 50% reduction in monthly migraine days relative to no treatment.

BRIEF DESCRIPTION OF THE FIGURES

FIG. 11 shows the migraine-specific quality of life questionnaire role function-restrictive domain score for weeks 4, 8, and 12 for all three atogepant doses and placebo. Significant differences vs. placebo were observed at the earliest time point assessed (week 4) and seen throughout the treatment period. All atogepant groups achieved within-group minimally important difference among the MSQ v 2.1 domains at weeks 4, 8 and 12.

As shown in FIG. 20, treatment with atogepant over the 52-week treatment period was associated with weight loss.

FIG. 21 is a CDF plot of weight loss for the safety population in the long-term safety study at 3 months; FIG. 22 is a CDF plot of weight loss for the safety population in the long-term safety study at 6 months; FIG. 23 is a CDF plot of weight loss for the safety population in the long-term safety study at 9 months; and FIG. 24 is a CDF plot of weight loss for the safety population in the long-term safety study at 12 months.

DETAILED DESCRIPTION

Figure 1:
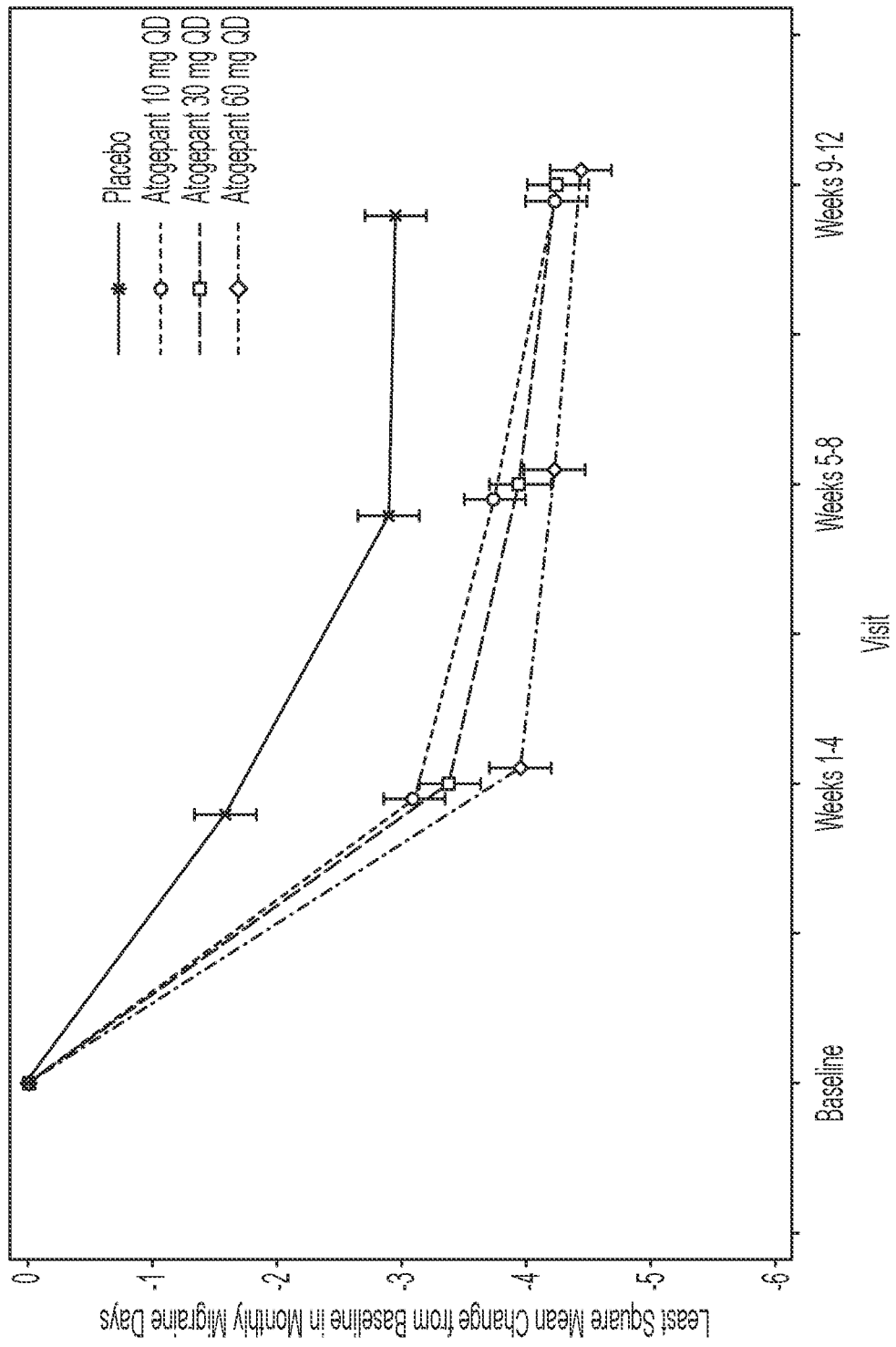
FIGS. 1 and 2 show the least square mean (+/−standard error of the least squares (SE)) of change from baseline in monthly migraine days (MMRM-mixed effects model for repeated measures) during the double-blind treatment period for the mITT population in Study A. There was a significant reduction in mean monthly migraine days across all three atogepant doses.

The present disclosure provides methods for treating migraine in a patient in need thereof. In embodiments, the present disclosure provides methods for the prophylactic treatment of patients suffering from migraine. In embodiments, the present disclosure provides methods for the treatment of migraine comprising administering a prophylactically effective amount of atogepant or a pharmaceutically acceptable salt thereof. The structure of atogepant is shown below:

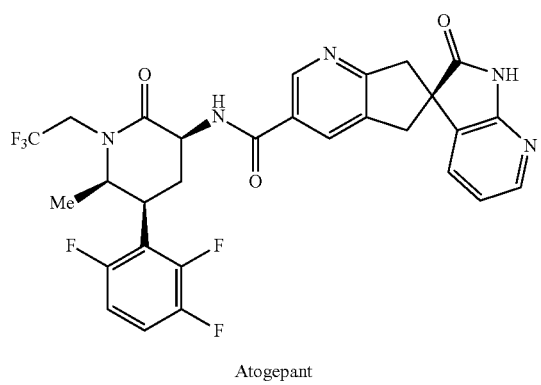 [SMILES: C[C@@H]1[C@H](c2c(F)ccc(F)c2F)C[C@H](NC(=O)c2cnc3c(c2)C[C@@]2(C3)C(=O)Nc3ncccc32)C(=O)N1CC(F)(F)F]

Atogepant

Atogepant is a small molecule CGRP receptor antagonist which may be administered orally, reaching maximum plasma concentrations by 2 hours, with a half-life of approximately 11 hours.

Prophylactic treatment can reduce the frequency and intensity of migraine attacks. In embodiments, the prophylactic methods can result in freedom from symptoms associated with migraine attacks, including headaches. In embodiments, the administration of atogepant may provide for fewer symptoms or symptoms of reduced intensity. In embodiments, the non-headache symptoms of migraine may be reduced or eliminated. In embodiments, the prophylactic methods of the present disclosure are directed to the entire range of symptoms experienced by a patient during a migraine attack, and not solely at the prevention of headaches associated with a migraine attack.

The indications for preventative treatment of migraine have been published by the American Academy of Neurology. See Update: Pharmacologic Treatment for Episodic Migraine Prevention in Adults, American Academy of Neurology, 2012. Prophylactic treatment is generally proposed for patients who suffer from two or more migraine attacks per month. Prophylactic treatment can also be used for patients who experience less frequent migraine attacks that are more potent or even disabling.

In embodiments, a patient in need of treatment may suffer from one or more symptoms of migraine including, for example, sinusitis, nausea, nasopharyngitis, photophobia, appetite changes, cognition and concentration difficulties, cold extremities, diarrhea or other bowel changes, excitement or irritability, fatigue, frequent urination, memory changes, weakness, yawning, stretching, seeing bright spots or flashes of light, vision loss, seeing dark spots, tingling sensations, speech problems, aphasia, tinnitus, gastric stasis, pulsating or throbbing pain on one or both sides of the head, extreme sensitivity to light, sounds, or smells, worsening pain during physical activity, and vomiting, abdominal pain or heartburn, loss of appetite, lightheadedness, blurred vision, and fainting. In embodiments, the administration of a prophylactically effective amount of atogepant results in the improvement, reduced frequency, or reduced intensity of symptoms.

In embodiments, the present disclosure provides a method for the prophylactic treatment of migraine comprising regularly administering to a patient in need thereof a therapeutically effective amount of atogepant, or a pharmaceutically acceptable salt thereof. In embodiments, atogepant is administered orally at a once-daily dose of 10 mg. In embodiments, atogepant is administered orally at a once-daily dose of 30 mg. In embodiments, atogepant is administered orally at a once-daily dose of 60 mg. In embodiments, atogepant is administered orally at a once-daily dose of 10 mg. In embodiments, atogepant is administered orally at a once-daily dose of 10 mg for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks.

In embodiments, atogepant is administered orally at a once-daily dose of 30 mg. In embodiments, atogepant is administered orally at a once-daily dose of 30 mg for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks.

In embodiments, atogepant is administered orally at a once-daily dose of 60 mg. In embodiments, atogepant is administered orally at a once-daily dose of 60 mg for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks.

In embodiments, atogepant, or a pharmaceutically acceptable salt thereof, is administered to a patient identified as susceptible to treatment with atogepant or a pharmaceutically acceptable salt thereof. A patient that suffers from episodic migraine may be considered susceptible to treatment with atogepant (for example 10 mg QD, 30 mg QD, or 60 mg QD) if after a treatment period of one month, two months, or three months, the patient achieves at least 70% reduction in migraine or probable migraine days, or at least 75% reduction, at least 80% reduction, at least 85% reduction, at least 90% reduction, at least 95% reduction or 100% reduction in migraine or probable migraine days.

In embodiments, atogepant or a pharmaceutically acceptable salt thereof, is administered to a patient suffering from episodic migraine for at least one month, or at least two months, or at least three months, and results in at least three fewer mean monthly migraine days, or at least 3.5 fewer mean monthly migraine days, or at least 3.6 fewer mean monthly migraine days, or at least 3.7 fewer monthly migraine days, or at least 3.8 mean monthly migraine days, or at least 4 fewer mean monthly migraine days, or at least 4.2 fewer monthly migraine days relative to no treatment.

In embodiments, the present disclosure provides a method for preventing migraine, such as a method for preventing migraine in a patient having fewer than fifteen migraine days per month (such as ≤14 migraine days per month, or between 4 and 14 migraine days per month), wherein the method comprises administering atogepant in an amount of 10 mg QD, 30 mg QD, or 60 mg QD, resulting in a reduction in mean monthly migraine days. In embodiments, treatment results in at least 3.4 fewer mean monthly migraine days, or at least 3.5 fewer mean monthly migraine days, or at least 3.6 fewer mean monthly migraine days, or at least 3.7 fewer mean monthly migraine days, or at least 3.8 mean monthly migraine days, or at least 4 fewer mean monthly migraine days, or at least 4.2 fewer monthly migraine days.

In embodiments, the present disclosure provides a method for preventing migraine (such as a method for preventing migraine in patients having fewer than fifteen migraine days per month), wherein atogepant is administered in an amount of 10 mg QD, 30 mg QD, or 60 mg QD to a population of human patients, resulting in a reduction in mean monthly migraine days. In embodiments, treatment results in at least 3.4 fewer mean monthly migraine days, or at least 3.5 fewer mean monthly migraine days, or at least 3.6 fewer mean monthly migraine days, or at least 3.7 fewer monthly migraine days, or at least 3.8 mean monthly migraine days, or at least 4 fewer mean monthly migraine days, or at least 4.2 fewer monthly migraine days. In embodiments, at least about 70% of the patients in the population of human patients have taken at least one prior preventive migraine therapy. In embodiments, the atogepant is administered for at least one month, or at least two months, or at least three months.

For example, in embodiments, the present disclosure provides a method for prophylactically treating migraine, comprising administering atogepant in an amount of 10 mg QD, resulting in a reduction in mean monthly migraine days. In embodiments, treatment results in at least 3.4 fewer monthly migraine days, or at least 3.5 fewer mean monthly migraine days, or at least 3.6 fewer mean monthly migraine days, or at least 3.65 fewer mean monthly migraine days, or at least 3.69 fewer mean monthly migraine days.

In embodiments, the present disclosure provides a method for preventing migraine, such as a method for preventing migraine in a patient having fewer than fifteen migraine days per month (such as ≤14 migraine days per month, or between 4 and 14 migraine days per month), wherein the method comprises administering atogepant in an amount of 10 mg QD, resulting in a reduction in mean monthly migraine days. In embodiments, administering atogepant results in at least 3.4 fewer monthly migraine days, or at least 3.5 fewer mean monthly migraine days, or at least 3.6 fewer mean monthly migraine days, or at least 3.65 fewer mean monthly migraine days, or at least 3.69 fewer mean monthly migraine days.

In embodiments, the present disclosure provides a method for preventing migraine, such as a method for preventing migraine in patients having fewer than 15 migraine days per month (such as ≤14 migraine days per month, or between 4 and 14 migraine days per month), wherein the method comprises administering atogepant in an amount of 10 mg QD to a population of human patients, resulting in a reduction in mean monthly migraine days. In embodiments, at least about 70% of the patients in the population have taken at least one prior preventive migraine therapy. In embodiments, administering atogepant results in at least 3.4 fewer mean monthly migraine days, or at least 3.5 fewer mean monthly migraine days, or at least 3.6 fewer mean monthly migraine days, or at least 3.65 fewer mean monthly migraine days, or at least 3.69 fewer mean monthly migraine days.

In embodiments, the present disclosure provides a method for prophylactically treating migraine, comprising administering atogepant in an amount of 30 mg QD, resulting in a reduction in mean monthly migraine days. In embodiments, treatment results in at least 3.4 fewer monthly migraine days, or at least 3.5 fewer mean monthly migraine days, or at least 3.6 fewer mean monthly migraine days, or at least 3.7 fewer mean monthly migraine days, or at least 3.8 fewer mean monthly migraine days, or at least 3.8 fewer mean monthly migraine days, or at least 3.86 fewer mean monthly migraine days.

In embodiments, the present disclosure provides a method for preventing migraine, such as a method for preventing migraine in a patient having fewer than fifteen migraine days per month (such as ≤14 migraine days per month, or between 4 and 14 migraine days per month), wherein the method comprises administering atogepant in an amount of 30 mg QD, resulting in a reduction in mean monthly migraine days. In embodiments, treatment results in at least 3.4 fewer mean monthly migraine days, or at least 3.5 fewer mean monthly migraine days, or at least 3.6 fewer mean monthly migraine days, or at least 3.7 fewer mean monthly migraine days, or at least 3.8 fewer mean monthly migraine days, or at least 3.8 fewer mean monthly migraine days, or at least 3.86 fewer mean monthly migraine days.

In embodiments, the present disclosure provides a method for preventing migraine, such as a method for preventing migraine in patients having fewer than 15 migraine days per month (such as ≤14 migraine days per month, or between 4 and 14 migraine days per month), wherein the method comprises administering atogepant in an amount of 30 mg QD to a population of human patients, resulting in a reduction in mean monthly migraine days. In embodiments, at least about 70% of the patients in the population have taken at least one prior migraine therapy. In embodiments, treatment results in at least 3.4 fewer mean monthly migraine days, or at least 3.5 fewer mean monthly migraine days, or at least 3.6 fewer mean monthly migraine days, or at least 3.7 fewer mean monthly migraine days, or at least 3.8 fewer mean monthly migraine days, or at least 3.8 fewer mean monthly migraine days, or at least 3.86 fewer mean monthly migraine days.

In embodiments, the present disclosure provides a method for prophylactically treating migraine, comprising administering atogepant in an amount of 60 mg QD, resulting in a reduction in mean monthly migraine days. In embodiments, treatment results in at least 3.4 fewer monthly migraine days, or at least 3.5 fewer mean monthly migraine days, or at least 3.6 fewer mean monthly migraine days, or at least 3.7 fewer mean monthly migraine days, or at least 3.8 fewer mean monthly migraine days, or at least 3.8 fewer mean monthly migraine days, or at least 3.9 fewer mean monthly migraine days, or at least 4.0 fewer mean monthly migraine days, or at least 4.1 fewer mean monthly migraine days, or at least 4.2 fewer mean monthly migraine days.

In embodiments, the present disclosure provides a method for preventing migraine, such as a method for preventing migraine in a patient having fewer than fifteen migraine days per month (such as ≤14 migraine days per month, or between 4 and 14 migraine days per month), wherein the method comprises administering atogepant in an amount of 60 mg QD, resulting in a reduction in mean monthly migraine days. In embodiments, administering atogepant results in at least 3.4 fewer mean monthly migraine days, or at least 3.5 fewer mean monthly migraine days, or at least 3.6 fewer mean monthly migraine days, or at least 3.7 fewer mean monthly migraine days, or at least 3.8 fewer mean monthly migraine days, or at least 3.8 fewer mean monthly migraine days, or at least 3.9 fewer mean monthly migraine days, or at least 4.0 fewer mean monthly migraine days, or at least 4.1 fewer mean monthly migraine days, or at least 4.2 fewer mean monthly migraine days.

Treatment with atogepant can result in an early and sustained reduction in monthly migraine days. For example, treatment with atogepant can result in a treatment effect as early as the first full day after starting treatment with atogepant. In embodiments, the present disclosure provides a method of preventing migraine, such as a method for preventing migraine in a patient having fewer than fifteen migraine days per month (such as ≤14 migraine days per month, or between 4 and 14 migraine days per month), the method comprising administering atogepant in an amount of 10 mg or 30 mg or 60 mg, wherein patients treated with atogepant are less likely to have a migraine on the day following atogepant administration than patients who received placebo.

In embodiments, the present disclosure provides a method for preventing migraine, such as a method for preventing migraine in patients having fewer than 15 migraine days per month (such as ≤14 migraine days per month, or between 4 and 14 migraine days per month), wherein the method comprises administering atogepant in an amount of 60 mg QD to a population of human patients, resulting in a reduction in mean monthly migraine days. In embodiments, at least about 70% of the patients in the population have taken at least one prior migraine therapy. In embodiments, administering atogepant results in at least 3.4 fewer mean monthly migraine days, or at least 3.5 fewer mean monthly migraine days, or at least 3.6 fewer mean monthly migraine days, or at least 3.7 fewer mean monthly migraine days, or at least 3.8 fewer mean monthly migraine days, or at least 3.8 fewer mean monthly migraine days, or at least 3.9 fewer mean monthly migraine days, or at least 4.0 fewer mean monthly migraine days, or at least 4.1 fewer mean monthly migraine days, or at least 4.2 fewer mean monthly migraine days.

In embodiments, the present disclosure provides a method for the prophylactic treatment of migraine comprising administering 10 mg atogepant or 30 mg atogepant or 60 mg atogepant to a patient in need thereof, wherein the patient achieves at least 50% reduction in 3-month average of monthly migraine days.

In embodiments, the present disclosure provides a method for preventing migraine, such as a method of preventing migraine in a patient having fewer than fifteen migraine days per month (such as ≤14 migraine days per month, or between 4 and 14 migraine days per month), the method comprising administering 10 mg atogepant or 30 mg atogepant or 60 mg atogepant, wherein the patient achieves at least 50% reduction in 3-month average of monthly migraine days.

In embodiments, the present disclosure provides a method for the prophylactic treatment/prevention of migraine in patients having fewer than fifteen migraine days per month (such as ≤14 migraine days per month, or between 4 and 14 migraine days per month), the method comprising administering 10 mg atogepant or 30 mg atogepant or 60 mg atogepant to a population of patients, wherein at least about 50% of patients achieve ≥50% reduction in a 3-month average of monthly migraine days, or at least about 55% of patients achieve ≥50% reduction in a 3-month average of monthly migraine days, or at least about 58% of patients achieve ≥50% reduction in a 3-month average of monthly migraine days, or at least about 60% of patients achieve ≥50% reduction in a 3-month average of monthly migraine days. In embodiments, at least about 70% of the patients in the population of patients have taken at least one prior migraine therapy.

In embodiments, the present disclosure provides a method for the prevention of migraine in patients having fewer than fifteen migraine days per month (such as ≤14 migraine days per month, or between 4 and 14 migraine days per month), the method comprising administering 10 mg atogepant to a population of patients, wherein at least about 50% of patients achieve ≥50% reduction in a 3-month average of monthly migraine days, or at least about 55% of patients achieve ≥50% reduction in a 3-month average of monthly migraine days.

In embodiments, the present disclosure provides a method for the preventive treatment of migraine in patients having fewer than fifteen migraine days per month (such as ≤14 migraine days per month, or between 4 and 14 migraine days per month), the method comprising administering 10 mg atogepant for at least four weeks to a population of patients, wherein at least about 40%, or at least about 45%, or at least about 49% of patients achieve ≥50% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 10 mg atogepant for at least four weeks to a population of patients, wherein at least about 20% of patients, or at least about 25% of patients, or at least about 27% of patients, achieve ≥75% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 10 mg atogepant for at least four weeks to a population of patients, wherein at least about 7%, or at least about 10%, or at least about 12%, or at least about 14% of patients achieve 100% reduction in monthly migraine days.

In embodiments, the present disclosure provides a method for the preventive treatment of migraine in patients having fewer than fifteen migraine days per month (such as ≤14 migraine days per month, or between 4 and 14 migraine days per month), the method comprising administering 10 mg atogepant for at least 8 weeks to a population of patients, wherein at least about 50%, or at least about 55%, or at least about 60% of patients achieve ≥50% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 10 mg atogepant for at least 8 weeks to a population of patients, wherein at least about 30%, or at least about 35%, or at least about 39% of patients achieve ≥75% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 10 mg atogepant for at least 8 weeks to a population of patients, wherein at least about 15%, or about 17%, or about 21% of patients achieve a 100% reduction in monthly migraine days.

In embodiments, the present disclosure provides a method for the preventive treatment of migraine in patients having fewer than fifteen migraine days per month (such as ≤14 migraine days per month, or between 4 and 14 migraine days per month), the method comprising administering 10 mg atogepant for at least 12 weeks to a population of patients, wherein at least about 55%, or 60%, or 64% of patients achieve ≥50% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 10 mg atogepant for at least 12 weeks to a population of patients, wherein at least about 35%, or 40%, or 43% of patients achieve ≥75% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 10 mg atogepant for at least 12 weeks to a population of patients, wherein at least about 15%, or about 17%, or about 21% of patients achieve a 100% reduction in monthly migraine days.

In embodiments, the present disclosure provides a method for the prevention of migraine in patients having fewer than fifteen migraine days per month (such as ≤14 migraine days per month, or between 4 and 14 migraine days per month), the method comprising administering 30 mg atogepant to a population of patients, wherein at least about 50% of patients achieve ≥50% reduction in a 3-month average of monthly migraine days, or at least about 55% of patients achieve ≥50% reduction in a 3-month average of monthly migraine days, or at least about 58% of patients achieve ≥50% reduction in a 3-month average of monthly migraine days.

In embodiments, the present disclosure provides a method for the preventive treatment of migraine in patients having fewer than fifteen migraine days per month (such as ≤14 migraine days per month, or between 4 and 14 migraine days per month), the method comprising administering 30 mg atogepant for at least 4 weeks to a population of patients, wherein at least about 40%, or about 45%, or about 48%, or about 49% of patients achieve ≥50% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 30 mg atogepant for at least 4 weeks to a population of patients, wherein at least about 20%, or about 25%, or about 26%, or about 27% of patients achieve ≥75% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 30 mg atogepant for at least four weeks to a population of patients, wherein at least about 7%, or at least about 10%, or at least about 11% of patients achieve 100% reduction in monthly migraine days.

In embodiments, the present disclosure provides a method for the preventive treatment of migraine in patients having fewer than fifteen migraine days per month (such as ≤14 migraine days per month, or between 4 and 14 migraine days per month), the method comprising administering 30 mg atogepant for at least 8 weeks to a population of patients, wherein at least about 50%, or at least about 55%, or at least about 60%, or at least about 61% of patients achieve ≥50% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 30 mg atogepant for at least 8 weeks to a population of patients, wherein at least about 30%, or at least about 35%, or at least about 36% of patients achieve ≥75% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 30 mg atogepant for at least 8 weeks to a population of patients, wherein at least about 15%, or about 17%, or about 18% of patients achieve a 100% reduction in monthly migraine days.

In embodiments, the present disclosure provides a method for the preventive treatment of migraine in patients having fewer than fifteen migraine days per month (such as ≤14 migraine days per month, or between 4 and 14 migraine days per month), the method comprising administering 30 mg atogepant for at least 12 weeks to a population of patients, wherein at least about 50%, or 55%, or 60% of patients achieve ≥50% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 30 mg atogepant for at least 12 weeks to a population of patients, wherein at least about 35%, or 40%, or 43% of patients achieve ≥75% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 30 mg atogepant for at least 12 weeks to a population of patients, wherein at least about 15%, or about 20%, or about 25%, or about 27% of patients achieve a 100% reduction in monthly migraine days.

In embodiments, the present disclosure provides a method for the prevention of migraine in patients having fewer than fifteen migraine days per month (such as ≤14 migraine days per month, or between 4 and 14 migraine days per month), the method comprising administering 60 mg atogepant to a population of patients, wherein at least about 50% of patients achieve ≥50% reduction in a 3-month average of monthly migraine days, or at least about 55% of patients achieve ≥50% reduction in a 3-month average of monthly migraine days, or at least about 58% of patients achieve ≥50% reduction in a 3-month average of monthly migraine days, or at least about 60% of patients achieve ≥50% reduction in a 3-month average of monthly migraine days.

In embodiments, the present disclosure provides a method for the preventive treatment of migraine in patients having fewer than fifteen migraine days per month (such as ≤14 migraine days per month, or between 4 and 14 migraine days per month), the method comprising administering 60 mg atogepant for at least 4 weeks to a population of patients, wherein at least about 50%, or about 55%, or about 60%, or about 61% of patients achieve ≥50% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 60 mg atogepant for at least 4 weeks to a population of patients, wherein at least about 25%, or about 30%, or about 35%, or about 39% of patients achieve ≥75% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 60 mg atogepant for at least four weeks to a population of patients, wherein at least about 10%, or at least about 15%, or at least about 19% of patients achieve 100% reduction in monthly migraine days.

In embodiments, the present disclosure provides a method for the preventive treatment of migraine in patients having fewer than fifteen migraine days per month (such as ≤14 migraine days per month, or between 4 and 14 migraine days per month), the method comprising administering 60 mg atogepant for at least 8 weeks to a population of patients, wherein at least about 50%, or at least about 55%, or at least about 60%, or at least about 65%, or at least about 66% of patients achieve ≥50% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 60 mg atogepant for at least 8 weeks to a population of patients, wherein at least about 30%, or at least about 35%, or at least about 40% of patients achieve ≥75% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 60 mg atogepant for at least 8 weeks to a population of patients, wherein at least about 15%, or about 20%, or about 22%, or about 24% of patients achieve a 100% reduction in monthly migraine days.

In embodiments, the present disclosure provides a method for the preventive treatment of migraine in patients having fewer than fifteen migraine days per month (such as ≤14 migraine days per month, or between 4 and 14 migraine days per month), the method comprising administering 60 mg atogepant for at least 12 weeks to a population of patients, wherein at least about 50%, or at least about 60%, or at least about 65%, or at least about 70%, or at least about 71% of patients achieve ≥50% reduction in monthly migraine days.

In embodiments, the present disclosure provides a method for the preventive treatment of migraine in patients having fewer than fifteen migraine days per month (such as ≤14 migraine days per month, or between 4 and 14 migraine days per month), the method comprising administering 60 mg atogepant for at least 12 weeks to a population of patients, wherein at least about 40%, or at least about 45%, or at least about 47%, or at least about 49% of patients achieve ≥75% reduction in monthly migraine days. In embodiments, the present disclosure provides a method for the preventive treatment of migraine in patients having fewer than fifteen migraine days per month (such as ≤14 migraine days per month, or between 4 and 14 migraine days per month), the method comprising administering 60 mg atogepant for at least 12 weeks to a population of patients, wherein at least about 15%, or at least about 20%, or at least about 25%, or at least about 27% of patients achieve a 100% reduction in monthly migraine days.

In embodiments, the present disclosure provides a method for prophylactically treating migraine in a patient in need thereof comprising administering atogepant in a therapeutically effective amount, resulting in fewer headache days per month. In embodiments, treatment results in a change from baseline of at least 3.8 fewer mean monthly headache days, or at least 3.9 fewer monthly mean monthly headache days, or at least 4 fewer monthly mean monthly headache days, or at least 4.1 fewer monthly mean monthly headache days, or at least 4.2 fewer mean monthly headache days.

In embodiments, the present disclosure provides a method for preventing migraine (such as a method for preventing migraine in patients having fewer than fifteen migraine days per month), wherein atogepant is administered in an amount of 10 mg QD, 30 mg QD, or 60 mg QD to a population of human patients, resulting in fewer headache days per month. In embodiments, at least about 70% of patients in the population have taken at least one prior migraine therapy. In embodiments, treatment results in a change from baseline of at least 3.8 fewer mean monthly headache days, or at least 3.9 fewer monthly mean monthly headache days, or at least 4 fewer monthly mean monthly headache days, or at least 4.1 fewer monthly mean monthly headache days, or at least 4.2 fewer mean monthly headache days.

For example, in embodiments, the present disclosure provides a method for preventing migraine (such as a method for preventing migraine in patients having fewer than fifteen migraine days per month), wherein atogepant is administered in an amount of 10 mg QD to a population of human patients, resulting in fewer headache days per month. In embodiments, at least about 70% of patients in the population have taken at least one prior migraine therapy. In embodiments, administering atogepant results in a change from baseline of at least 3.8 fewer mean monthly headache days, or at least 3.9 fewer monthly mean monthly headache days.

In embodiments, the present disclosure provides a method for preventing migraine (such as a method for preventing migraine in patients having fewer than fifteen headache days per month), wherein atogepant is administered in an amount of 30 mg QD to a population of human patients, resulting in fewer headache days per month. In embodiments, at least about 70% of patients in the population have taken at least one prior migraine therapy. In embodiments, treatment results in a change from baseline of at least 3.8 fewer monthly headache days, or at least 3.9 fewer monthly mean monthly headache days, or at least 4 fewer monthly mean monthly headache days.

In embodiments, the present disclosure provides a method for preventing migraine (such as a method for preventing migraine in patients having fewer than fifteen migraine days per month), wherein atogepant is administered in an amount of 30 mg QD to a population of human patients, resulting in fewer headache days per month. In embodiments, at least about 70% of patients in the population have taken at least one prior migraine therapy. In embodiments, treatment results in a change from baseline of at least 3.8 fewer mean monthly headache days, or at least 3.9 fewer monthly mean monthly headache days, or at least 4 fewer monthly mean monthly headache days, or at least 4.1 fewer monthly mean monthly headache days, or at least 4.2 fewer mean monthly headache days.

In embodiments, the present disclosure provides a method for prophylactically treating migraine in a patient in need thereof, the method comprising administering atogepant in an amount of 10 mg, 30 mg, or 60 mg, resulting in fewer acute medication use days per month. In embodiments, treatment with atogepant results in a reduction in mean monthly acute medication use days of at least 3.5 days, or at least 3.6 days, or at least 3.66 days, or at least 3.68 days, or at least 3.7 days, or at least 3.8 days, or at least 3.85 days.

In embodiments, the present disclosure provides a method for preventing migraine (such as a method for preventing migraine in patients having fewer than fifteen migraine days per month), wherein atogepant is administered in an amount of 10 mg QD, 30 mg QD, or 60 mg QD to a population of human patients, resulting in fewer acute medication use days per month. In embodiments, at least about 70% of the patients in the population of human patients have taken at least one prior migraine therapy. In embodiments, treatment with atogepant results in a reduction in mean monthly acute medication use days of at least 3.5 days, or at least 3.6 days, or at least 3.66 days, or at least 3.68 days, or at least 3.7 days, or at least 3.8 days, or at least 3.85 days.

For example, in embodiments, the present disclosure provides a method for preventing migraine (such as a method for preventing migraine in patients having fewer than fifteen migraine days per month), wherein atogepant is administered in an amount of 10 mg QD. In embodiments, at least about 70% of the patients in the population of human patients have taken at least one prior migraine therapy. In embodiments, treatment with atogepant results in a reduction in mean monthly acute medication use days of at least 3.5 days, or at least 3.6 days, or at least 3.66 days.

In embodiments, the present disclosure provides a method for preventing migraine (such as a method for preventing migraine in patients having fewer than fifteen migraine days per month), wherein atogepant is administered in an amount of 30 mg QD. In embodiments, at least about 70% of the patients in the population of human patients have taken at least one prior migraine therapy. In embodiments, treatment with atogepant results in a reduction in mean monthly acute medication use days of at least 3.5 days, or at least 3.6 days, or at least 3.66 days, or at least 3.68 days.

In embodiments, the present disclosure provides a method for preventing migraine (such as a method for preventing migraine in patients having fewer than fifteen migraine days per month), wherein atogepant is administered in an amount of 60 mg QD. In embodiments, at least about 70% of the patients in the population of human patients have taken at least one prior migraine therapy. In embodiments, treatment with atogepant results in a reduction in mean monthly acute medication use days of at least 3.5 days, or at least 3.6 days, or at least 3.66 days, or at least 3.68 days, or at least 3.7 days, or at least 3.8 days, or at least 3.85 days.

In embodiments, the present disclosure provides methods for preventing or prophylactically treating migraine to result in improved patient function. In embodiments, the present disclosure provides methods for preventing migraine (such as a method of preventing migraine in patients having fewer than fifteen migraine days per month) by administering atogepant, resulting in an improvement in the physical impairment or quality-of-life impact scores reported by patients as compared to a pre-treatment baseline and/or a patient not receiving atogepant. Migraines can impact patient quality of life, impact productivity, and prevent patients from engaging in leisure and everyday activities. "Improved patient function" can be defined as an improvement measured by factors such as a reduced pain, reduced time spent in bed, increased ambulation, healthier attitude, more varied lifestyle and/or healing permitted by normal muscle tone. Improved patient function may be measured with an improved quality of life (QOL) or Health-Related Quality of Life (HRQL). These effects can be assessed, for example, using questionnaires or surveys, such as the Migraine-Specific Quality of Life Questionnaire (MSQ), the Headache Impact Test ("Headache Impact Test-6" or "HIT-6"), or the Activity Impairment in Migraine Diary (AIM-D). Scores obtained can be compared to published values available for various general and patient populations.

The Migraine-Specific Quality of Life Questionnaire Version 2.1 is one of the most frequently utilized disease-specific tools assessing the impact of migraine on HRQL. The MSQ is a validated tool that assess the impact of migraine on function (i.e., daily social and work-related activities) over the past 4 weeks across three dimensions: Role Function-Restrictive (RR, or "RFR", relating to how migraines limit the patient's daily social and work related activities), Role Function-Preventive (RP, e.g., how migraines prevent the patient's daily social and work related activities), and Emotional Function (EF, e.g., the emotions associated with a patient's migraines). Patients respond to items using a 6-point scale: "none of the time," "a little bit of the time," "some of the time", "a good bit of the time," "most of the time" and "all of the time," which are assigned scores of 1 to 6, respectively. Raw dimension scores are computed as a sum of item responses and rescaled from a 0 to 100 scale such that higher scores indicate better quality of life. See Bagley et al., *Validating Migraine-Specific Quality of Life Questionnaire v2.1 in Episodic and Chronic Migraine*, Headache, 2012 March; 52(3):409-21.

In embodiments, the present disclosure provides a method for preventing migraine in a patient or group of patients (such as a method for preventing migraine in a patient having fewer than fifteen migraine days per month), wherein atogepant is administered in an amount of 10 mg, 30 mg, or 60 mg once daily, and wherein administration of atogepant results in improvements in the ability to perform daily activities. In embodiments, the improvement in the ability to perform daily activities is measured by the MSQ v2.1. In embodiments, treatment with atogepant results in a change from baseline in the MSQ v2.1 RFR Domain of greater than about 21.0 points, such as greater than about 25.0 points, or greater than about 30.0 points, or greater than about 30.1 points, or greater than about 30.2 points, or greater than about 30.3 points, or greater than about 30.4 points, or greater than about 30.5 points, or greater than about 31.0 points, or greater than about 31.3 points relative to baseline.

In embodiments, the present disclosure provides a method for preventing migraine in a patient or group of patients (such as a method for preventing migraine in a patient or group of patients having fewer than fifteen migraine days per month), wherein atogepant is administered in an amount of about 10 mg QD, wherein the administration of atogepant results in an improvement in the ability to perform daily activities as measured by the MSQ v2.1. In embodiments, treatment with atogepant results in a change from baseline in the MSQ v2.1 RFR Domain of greater than about 25.0 points, or greater than about 30.0 points, or greater than about 30.1 points, or greater than about 3.2 points, or greater than about 30.3 points, or greater than about 30.4 points relative to baseline. For example, in embodiments, atogepant is administered in an amount of about 10 mg QD, and the ability to perform daily activities as measured by the MSQ v2.1 RFR Domain improves by about 30.4 points relative to baseline.

In embodiments, the present disclosure provides a method for preventing migraine (such as a method for preventing migraine in a patient or group of patients (such as a method for preventing migraine in a patient or group of patients having fewer than fifteen migraine days per month), wherein atogepant is administered in an amount of about 30 mg QD, wherein administration of atogepant results in an improvement in the ability to perform daily activities as measured by the MSQ v2.1. In embodiments, treatment with atogepant results in a change from baseline in the MSQ v2.1 RFR Domain of greater than about 25.0 points, or greater than about 30.0 points, or greater than about 30.1 points, or greater than about 30.2 points, or greater than about 30.3 points, or greater than about 30.4 points, or greater than about 30.5 points relative to baseline. For example, in embodiments, atogepant is administered in an amount of about 30 mg QD, and the ability to perform daily activities as measured in the MSQ v2.1 RFR Domain improves by about 30.5 points relative to baseline.

In embodiments, the present disclosure provides a method for preventing migraine in a patient or group of patients (such as a method for preventing migraine in a patient or group of patients having fewer than fifteen migraine days per month), wherein atogepant is administered in an amount of about 60 mg QD, wherein administration of atogepant results in an improvement in the ability to perform daily activities as measured by the MSQ v2.1. In embodiments, treatment with atogepant results in a change from baseline in the MSQ v2.1 RFR Domain of greater than about 25.0 points, or greater than about 30.0 points, or greater than about 30.1 points, or greater than about 30.2 points, or greater than about 30.3 points, or greater than about 30.4 points, or greater than about 30.5 points, or greater than about 31.0 points, or greater than about 31.3 points relative to baseline. For example, in embodiments, atogepant is administered in an amount of about 60 mg QD, and the ability to perform daily activities as measured in the MSQ v2.1 RFR Domain improves by about 31.3 points relative to baseline.

The Activity in Migraine Diary (AIM-D) evaluates the impact of migraine on the performance of daily activities and physical impairment using an electronic daily diary. In particular, the AIM-D is comprised of two domains that evaluate Performance of Daily Activities (PDA) and Physical Impairment (PI). Assessed items for the AIM-D PDA domain include household chores, errands, leisure activities at home, social or leisure activities outside the home, strenuous physical activities, concentration, and thinking clearly. Assessed items for the AIM-D PI Domain include walking, moving one's body, bending forward, and moving one's head. Response options for each item range from "not difficult at all" to "I could not do it at all" on a 6-point rating scale. The AIM-D domain scores are scaled from 0-100, with higher scores indicating greater impact of migraine, and reductions from baseline in scores indicate improvement. See Cala et al., The Activity Impairment in Migraine-Diary (AIM-D): A Novel Migraine-Specific Patient-Reported Outcome Measure to Assess Functioning Based on Activity Impairment in Episodic and Chronic Migraine Patients, MTIS2018-005 (Sep. 5, 2018).

In embodiments, the present disclosure provides a method for preventing migraine (such as a method for preventing migraine in a patient having fewer than fifteen migraine days per month), wherein atogepant is administered in an amount of 10 mg, 30 mg, or 60 mg once daily, wherein administration of atogepant results in improvements in performance of daily activities and physical impairment. In embodiments, the improvement is assessed using a daily diary. In embodiments, the daily diary is the Activity Impairment in Migraine Diary (AIM-D). In embodiments, the daily activities include household chores, errands, leisure activities at home, social or leisure activities outside the home, strenuous physical activities, concentration, and thinking clearly. In embodiments, administration of atogepant results in less physical impairment in activities such as walking, moving the body, bending forward, and moving one's head.

In embodiments, the present disclosure provides a method for preventing migraine in a patient or group of patients (such as a method for preventing migraine in a patient or group of patients having fewer than fifteen migraine days per month) wherein atogepant is administered in an amount of 10 mg QD, 30 mg QD, or 60 mg QD, and reduces the patient's AIM-D Performance of Daily Activities score relative to baseline by more than about 6 points, or more than about 7 points, or more than about 7.5 points or more than about 8 points, or more than about 8.3 points, or more than about 8.6 points, or more than about 9 points, more than about 9.4 points. In embodiments, the present disclosure provides a method for preventing migraine in a patient or group of patients (such as a method for preventing migraine in a patient or group of patients having fewer than fifteen migraine days per month) wherein atogepant is administered in an amount of 10 mg QD, 30 mg QD, or 60 mg QD, and reduces the patient's AIM-D Physical Impairment score by more than about 4 points, or more than about 5 points, or more than about 5.5 points, or more than about 6 points, or more than about 6.5 points relative to baseline.

In embodiments, the present disclosure provides a method for preventing migraine in a patient or group of patients (such as a method for preventing migraine in a patient or group of patients having fewer than fifteen migraine days per month) wherein atogepant is administered in an amount of about 30 mg QD, resulting in a reduction in the AIM-D Performance of Daily Activities score of more than about 7.5 points relative to baseline, such as more than about 7.7 points, or more than about 8 points, or more than about 8.2 points, or more than about 8.4 points, or more than about 8.6 points relative to baseline. In embodiments, the reduction in the AIM-D PDA Score is about 8.6 points relative to baseline (i.e., −8.6 relative to baseline).

In embodiments, the present disclosure provides a method for preventing migraine in a patient or a group of patients (such as a method for preventing migraine in a patient or group of patients having fewer than fifteen migraine days per month) wherein atogepant is administered in an amount of about 60 mg QD, resulting in a reduction in the AIM-D Performance of Daily Activities Score of more than about 7.5 points relative to baseline, such as more than about 7.7 points, or more than about 8 points, or more than about 8.2 points, or more than about 8.4 points, or more than about 8.6 points, or more than about 8.8 points, or more than about 9 points, or more than about 9.2 points, or more than about 9.4 points relative to baseline. In embodiments, the reduction in the AIM-D PDA score is about 9.4 points relative to baseline (i.e., −9.4 relative to baseline).

In embodiments, the present disclosure provides a method for preventing migraine in a patient or group of patients (such as a method for preventing migraine in a patient or group of patients having fewer than fifteen migraine days per month) wherein atogepant is administered in an amount of about 30 mg QD, resulting in a reduction in the AIM-D Physical Impairment Score of more than about 5.2 points relative to baseline, such as more than about 5.5 points, or more than about 5.7 points, or more than about 6.0 points relative to baseline. In embodiments, the reduction in the AIM-D PI score is about 6.0 points relative to baseline (i.e., −6.0 relative to baseline).

In embodiments, the present disclosure provides a method for preventing migraine in a patient or group of patients (such as a method for preventing migraine in a patient or group of patients having fewer than fifteen migraine days per month) wherein atogepant is administered in an amount of about 60 mg QD, resulting in a reduction in the AIM-D Physical Impairment Score of more than about 5.2 points relative to baseline, such as more than about 5.5 points, or more than about 5.7 points, or more than about 6.0 points, or more than about 6.3 points, or more than about 6.5 points relative to baseline. In embodiments, the reduction in the AIM-D PI Score is about 6.5 points relative to baseline (i.e., −6.5 relative to baseline).

In embodiments, the present disclosure provides a method for preventing migraine (such as a method for preventing migraine in patients having fewer than fifteen migraine days per month) wherein atogepant is administered in an amount of 10 mg QD, 30 mg QD, or 60 mg QD, wherein administration of atogepant results in a reduction in a 6-item Headache Impact Test (HIT-6) disability score relative to baseline. The Headache Impact Test (HIT-6) is a well-known tool for assessing migraine intensity, and uses six questions to measure the adverse impact of headache on, for example, social functioning, role functioning, vitality, cognitive functioning, and psychological distress. Responses are based on frequency using a 5-point verbal response scale ranging from "never" to "always". The HIT-6 total score is the sum of the responses, and ranges from 36 to 78. See Yang et al., *Validation of the Headache Impact Test (HIT-6™) Across Episodic and Chronic Migraine*, Cephalalgia 2011 February; 31(3): 357-367. In embodiments, treatment with atogepant results in a greater than five (≥5) point decrease in HIT-6 disability score.

Long-Term Treatment with Atogepant

In embodiments, atogepant may be administered daily for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks. Based on the clinical data, atogepant may be administered safely for at least up to 52 weeks.

For example, in embodiments, atogepant may be administered at a dose of 10 mg QD, or 30 mg QD, or 60 mg QD for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks.

For example, in an embodiment, atogepant may be administered in an amount of 60 mg once daily for at least 52 weeks. In embodiments, treatment with atogepant results in a reduction in mean monthly migraine days of at least 3.8 days, or at least 4.1 days, or at least 4.3 days, or at least 4.6 days, or at least 4.7 days, or at least 4.8 days, or at least 4.9 days, or at least 5 days, or at least 5.1 days, or at least 5.19 days.

In embodiments, the present disclosure provides a method for the preventive treatment of migraine in patients having fewer than fifteen migraine days per month (such as ≤14 migraine days per month, or between 4 and 14 migraine days per month), the method comprising administering atogepant in an amount of 10 mg, 30 mg, or 60 mg for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks. For example, in embodiments, the present disclosure provides a method for the preventive treatment of migraine in patients having between 4-14 migraine days per month, the method comprising administering atogepant 60 mg QD for at least 52 weeks, wherein the treatment results in a reduction in mean monthly migraine days of at least 5 days, or at least 5.1 days, or at least 5.19 days.

In embodiments, the present disclosure provides a method for the preventive treatment of migraine comprising administering 10 mg, 30 mg, or 60 mg atogepant for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks, wherein treatment results in a >=50% improvement (reduction) in monthly migraine days at each monthly period. In embodiments, at least 60% of patients achieve >=50% improvement (reduction) in monthly migraine days at each monthly period, or at least 70%, or at least 80%. In embodiments, the present disclosure provides a method for the preventive treatment of migraine in patients having fewer than fifteen migraine days per month, the method comprising administering atogepant 60 mg QD for at least 52 weeks, wherein treatment results in at least 50% improvement (reduction) in monthly migraine days at each monthly period.

In embodiments, the present disclosure provides methods for the prevention of migraine in patients having fewer than 15 migraine days per month (such as ≤14 migraine days per month, or between 4 and 14 migraine days per month), the method comprising administering 10 mg, 30 mg, or 60 mg QD for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks, resulting in fewer headache days per month. For example, in embodiments, the present disclosure provides a method for the preventive treatment of migraine in patients having fewer than 15 migraine days per month, the method comprising administering atogepant 60 mg QD for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks, wherein treatment with atogepant results in a reduction from baseline in monthly headache days of at least 4 days, or at least 5 days, or at least 5.3 days, or at least 5.6 days, or at least 5.9 days, or at least 5.99 days. In embodiments, the present disclosure provides a method for the preventive treatment of migraine, the method comprising administering atogepant 60 mg QD for at least 52 weeks, resulting in a reduction from baseline in monthly headache days of at least 5.9 days.

In embodiments, the present disclosure provides methods for the prevention of migraine in patients having fewer than 15 migraine days per month (such as ≤14 migraine days per month, or between 4 and 14 migraine days per month), the method comprising administering 10 mg, 30 mg, or 60 mg QD for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks, resulting in a reduction in mean monthly acute medication use days. For example, in embodiments, the present disclosure provides methods for the preventive treatment of migraine in patients having fewer than 15 migraine days per month, the method comprising administering 60 mg atogepant QD for at least 4 weeks, or 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks, wherein treatment with atogepant results in a reduction in mean monthly acute medication use days of at least 4 days, or at least 4.4 days, or at least 4.5 days, or at least 4.6 days, or at least 4.7 days, or at least 4.9 days, or at least 4.93 days. In embodiments, the present disclosure provides methods for the preventive treatment of migraine, the method comprising administering atogepant 60 mg QD for at least 52 weeks, resulting in a change from baseline in acute monthly medication use days of about 4.93 days.

Atogepant and Weight Loss

Migraine and obesity are co-morbid conditions. Obesity has previously been linked both to an increased prevalence of migraine and also to increased migraine attack frequency leading to progression from episodic to chronic migraine. See Kristoffersen et al., *Migraine, Obesity, and Body Fat Distribution—a Population-Based Study*, J. Headache & Pain 21: 97 (2020); Bigal M E, Liberman J N, Lipton R B (2006) Obesity and migraine: a population study. Neurology. 66(4):545-550; Bigal M E, Tsang A, Loder E, Serrano D, Reed M L, Lipton R B (2007) Body mass index and episodic headaches: a population-based study. Arch Intern Med 167 (18):1964-1970; Peterlin B L, Rosso A L, Rapoport A M, Scher A I (2010) Obesity and migraine: the effect of age, gender and adipose tissue distribution. Headache. 50(1):52-62; Scher A I, Stewart W F, Ricci J A, Lipton R B (2003) Factors associated with the onset and remission of chronic daily headache in a population-based study. Pain. 106(1-2): 81-89; Gelaye B, Sacco S, Brown W J, Nitchie H L, Ornello R, Peterlin B L (2017) Body composition status and the risk of migraine: a meta-analysis. Neurology. 88(19):1795-1804; Ornello R, Ripa P, Pistoia F, Degan D, Tiseo C, Carolei A et al (2015) Migraine and body mass index categories: a systematic review and meta-analysis of observational studies. J Headache Pain. 16:27; Winter A C, Berger K, Buring J E, Kurth T (2009) Body mass index, migraine, migraine frequency and migraine features in women. Cephalalgia. 29(2):269-278. Each of these references are incorporated by reference herein in their entireties.

40% of patients with migraine disease are obese (BMI≥30 $kg/m^2$). Further, migraine patients with BMI≥27 27 $kg/m^2$ with obesity-related comorbidities (type 2 diabetes, hypertension, dyslipidemia, sleep apnea, cardiovascular disease).

Treatment of obesity has been associated with both improved general health and improved migraine disease.

It has been discovered that certain dosages of atogepant, when administered over a sufficient period of time, are associated with weight loss.

Accordingly, in embodiments, the present disclosure provides a method for the preventive treatment of migraine, the method comprising administering atogepant to a patient in an amount effective to both prevent migraine and reduce the patient's body weight. For example, in embodiments, the present disclosure provides a method for the preventive treatment of migraine, the method comprising administering atogepant in an amount effective to reduce both the patient's monthly migraine days and the patient's body weight. In embodiments, the patient's body weight is reduced as compared to the patient's body weight before taking atogepant.

In embodiments, the present disclosure provides a method for the preventive treatment of migraine, such as a method for preventing migraine in patients having fewer than 15 migraine days per month (such as ≤14 migraine days per month, or between 4 and 14 migraine days per month), the method comprising administering atogepant daily to a patient for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks, wherein administration of atogepant results in a reduction in body weight by at least 0.5 kg, or at least 0.6 kg, or at least 0.7 kg, or at least 0.8 kg, or at least 0.9 kg, or at least 1 kg, or at least 1.1 kg, or at least 1.2 kg, or at least 1.3 kg, or at least 1.4 kg, or at least 1.42 kg. In embodiments, atogepant is administered daily in an amount of 10 mg, 30 mg, or 60 mg.

In embodiments, the present disclosure provides a method for the preventive treatment of migraine, such as a method for preventing migraine in patients having fewer than 15 migraine days per month (such as ≤14 migraine days per month, or between 4 and 14 migraine days per month), the method comprising administering 30 mg or 60 mg atogepant QD for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks, resulting in a reduction in body weight by at least 0.5 kg, or at least 0.6 kg, or at least 0.7 kg, or at least 0.8 kg, or at least 0.9 kg, or at least 1 kg, or at least 1.1 kg, or at least 1.2 kg, or at least 1.3 kg, or at least 1.4 kg, or at least 1.42 kg. Based on the clinical data, atogepant may be administered safely for at least up to 52 weeks.

For example, in embodiments, the present disclosure provides a method for the preventive treatment of migraine, such as a method for preventing migraine in patients having fewer than 15 migraine days per month (such as ≤14 migraine days per month, or between 4 and 14 migraine days per month), the method comprising administering 30 mg atogepant QD for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks, resulting in a reduction in body weight by at least 0.5 kg, or at least 0.6 kg.

In embodiments, the present disclosure provides a method for the preventive treatment of migraine, such as a method for preventing migraine in patients having fewer than 15 migraine days per month (such as ≤14 migraine days per month, or between 4 and 14 migraine days per month), the method comprising administering 30 mg atogepant QD for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks, wherein the mean difference for percentage change from baseline in body weight is at least about 0.7%, or at least about 0.8%, or at least about 0.9%, or at least about 0.98%. In embodiments, the present disclosure provides a method for the preventive treatment of migraine, the method comprising administering 30 mg atogepant QD for at least about 12 weeks, wherein the mean difference for percentage change from baseline in body weight is about 0.98%. In embodiments, the present disclosure provides a method for the preventive treatment of migraine, such as a method for preventing migraine in patients having fewer than 15 migraine days per month (such as ≤14 migraine days per month, or between 4 and 14 migraine days per month), the method comprising administering 30 mg once daily for at least about 12 weeks, wherein treatment with atogepant results in at least about 3.2% of patients achieving a weight decrease of greater than about 7% from baseline.

In embodiments, the present disclosure provides a method for the preventive treatment of migraine, such as a method for preventing migraine in patients having fewer than 15 migraine days per month (such as ≤14 migraine days per month, or between 4 and 14 migraine days per month), the method comprising administering 60 mg atogepant QD for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks, resulting in a reduction in body weight by at least about 0.5 kg, or at least about 0.6 kg, or at least about 0.7 kg, or at least about 0.8 kg, or at least about 0.9 kg, or at least about 1 kg, or at least about 1.1 kg, or at least about 1.2 kg, or at least about 1.27 kg. In embodiments, the present disclosure provides a method for the preventive treatment of migraine, the method comprising administering 60 mg atogepant QD for at least 4 weeks, resulting in a reduction in body weight from baseline of at least about 0.6 kg, or at least about 0.7 kg, or at least about 0.8 kg, or at least about 0.81 kg. In embodiments, the present disclosure provides a method for the preventive treatment of migraine, the method comprising administering 60 mg atogepant QD for at least about 52 weeks, resulting in a reduction in body weight from baseline of at least about 1.1 kg, or at least about 1.2 kg, or at least about 1.3 kg, or at least about 1.4 kg, or at least about 1.42 kg.

In embodiments, the present disclosure provides a method for the preventive treatment of migraine, such as a method for preventing migraine in patients having fewer than 15 migraine days per month (such as ≤14 migraine days per month, or between 4 and 14 migraine days per month), the method comprising administering 60 mg atogepant QD for at least 4 weeks, or at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks, wherein the mean difference for percentage change from baseline in body weight is at least about 1.0%, or at least about 1.3%, or at least about 1.5%, or at least about 1.6%. In embodiments, the present disclosure provides a method for the preventive treatment of migraine, the method comprising administering 60 mg atogepant QD for at least about 12 weeks, wherein the mean difference for percentage change from baseline in body weight is about 1.64%.

In embodiments, the present disclosure provides a method for the preventive treatment of migraine, such as a method for preventing migraine in patients having fewer than 15 migraine days per month (such as ≤14 migraine days per month, or between 4 and 14 migraine days per month), the method comprising administering 60 mg QD atogepant for at least about 12 weeks, or at least about 16 weeks, or at least about 20 weeks, or at least about 24 weeks, or at least about 28 weeks, or at least about 32 weeks, or at least about 36 weeks, or at least about 40 weeks, or at least about 44 weeks, or at least about 48 weeks, or at least about 52 weeks to a population of patients, wherein at least about 10% of patients, or at least about 12% of patients, or at least about 14% of patients, achieve a weight decrease of greater than about 7% from baseline. In embodiments, the present disclosure provides a method for the preventive treatment of migraine, such as a method for preventing migraine in patients having fewer than 15 migraine days per month (such as ≤14 migraine days per month, or between 4 and 14 migraine days per month), the method comprising administering 60 mg atogepant once daily for at least about 12 weeks, wherein treatment with atogepant results in at least about 4.9% of patients achieving a weight decrease of greater than about 7% from baseline. In embodiments, the present disclosure provides a method for the preventive treatment of migraine, the method comprising administering 60 mg QD atogepant for at least about 6 months to a population of patients, wherein at least about 15% of patients, or at least about 18% of patients, or at least about 10% of patients, or at least about 22% of patients, achieve a weight decrease of greater than about 5% from baseline.

In embodiments, the present disclosure provides a method for the preventive treatment of migraine, the method comprising administering 60 mg QD atogepant for at least about six months to a population of patients, wherein at least about 8% of patients, or at least about 10% of patients, or at least about 12% of patients, achieve a weight decrease of greater than about 7% from baseline.

In embodiments, the present disclosure provides a method for the preventive treatment of migraine, the method comprising administering 60 mg QD atogepant for at least about 9 months to a population of patients, wherein at least about 15% of patients, or at least about 18% of patients, or at least about 10% of patients, or at least about 22% of patients, or at least about 25% of patients, achieve a weight decrease of greater than about 5% from baseline.

In embodiments, the present disclosure provides a method for the preventive treatment of migraine, the method comprising administering 60 mg QD atogepant for at least about nine months to a population of patients, wherein at least about 8% of patients, or at least about 10% of patients, or at least about 12% of patients, or at least about 14% of patients, achieve a weight decrease of greater than about 7% from baseline.

In embodiments, the present disclosure provides a method for the preventive treatment of migraine, the method comprising administering 60 mg QD atogepant for at least about 12 months to a population of patients, wherein at least about 18% of patients, or at least about 20% of patients, or at least about 22% of patients, or at least about 25% of patients, achieve a weight decrease of greater than about 5% relative to baseline. In embodiments, the present disclosure provides a method for the preventive treatment of migraine, the method comprising administering 60 mg atogepant QD for at least about 12 months, wherein at least about 22.4% of patients achieve a weight decrease of greater than about 5% relative to baseline body weight.

In embodiments, the present disclosure provides a method for the preventive treatment of migraine, the method comprising administering 60 mg QD atogepant for at least about 12 months to a population of patients, wherein at least about 10% of patients, or at least about 12% of patients, or at least about 15% of patients, achieve a weight decrease of greater than about 7% from baseline.

Definitions

"Administration" or "to administer" means the step of giving (i.e., administering) a pharmaceutical composition to a subject, or alternatively a subject receiving a pharmaceutical composition.

Calcitonin-Gene-Related-Peptide, or CGRP, encompasses any member of the calcitonin family, including any calcitonin gene related peptide and analogs, calcitonin, amylin, adrenomedullin and their analogs.

"CGRP antagonist" refers to any molecule that exhibits any one or more of the following characteristics: (a) bind to CGRP or CGRP-R and the binding results in a reduction or inhibition of CGRP activity; (b) block CGRP from binding to its receptor(s); (c) block or decrease CGRP receptor activation; (d) inhibit CGRP biological activity or downstream pathways mediated by CGRP signaling function; (e) increase clearance of CGRP; and (f) inhibit or reduce CGRP synthesis, production or release. CGRP antagonists include but are not limited to antibodies to CGRP, antibodies to the CGRP-R, small molecules that antagonize CGRP, and small molecules that antagonize CGRP-R.

The term "prophylactic" or "preventative" refers to the prevention of the onset, recurrence or spread of a disease or disorder, or of one or more symptoms associated with the disease or disorder. In one embodiment, such symptoms are those known to a person of skill in the art to be associated with the disease or disorder being prevented. In certain embodiments, the terms refer to the treatment with or administration of a compound provided herein prior to the onset of symptoms, particularly to patients at risk of disease or disorders provided herein. The terms encompass the inhibition or reduction of a symptom of the particular disease. For frequent migraines, prophylactic or preventative treatments are employed to reduce the frequency of migraines and also to reduce the severity and duration of migraines and their associated symptoms when they occur.

A "prophylactically effective amount" of a compound is an amount sufficient to prevent a disease or disorder, or prevent its recurrence. A prophylactically effective amount of a compound means an amount of therapeutic agent that can provide a prophylactic or preventative benefit in the prevention of the disease. The term "prophylactically effective amount" can encompass an amount that improves overall prophylaxis or prevention or enhances the prophylactic or preventative efficacy of another prophylactic agent.

"Effective amount" as applied to the biologically active ingredient means that amount of the ingredient which is generally sufficient to effect a desired change in the subject. For example, where the desired effect is a reduction in an autoimmune disorder symptom, an effective amount of the ingredient is that amount which causes at least a substantial reduction of the autoimmune disorder symptom, and without resulting in significant toxicity.

"Headache day" refers to any calendar day on which headache pain lasting two hours or longer occurs unless an acute headache medication (e.g., ibuprofen, triptan) was used after the start of the headache, in which case no minimum duration is specified.

"Migraine day" refers to any calendar day on which a headache occurs which meets criteria A, B, and C, or meets criteria D and E, as provided herein:
(A) Headache has at least two of the following four characteristics:
  (i) unilateral location,
  (ii) pulsating quality,
  (iii) moderate or severe pain intensity,
  (iv) aggravated by or causing avoidance of routine physical activity (e.g., walking or climbing stairs)
(B) At least one of the following:
  (i) Nausea and/or vomiting;
  (ii) Photophobia and phonophobia;
  (iii) Typical aura (i.e., visual, sensory, or speech/language) accompanying or within sixty minutes before headache begins
(C) Duration of headache lasting two hours or longer on a calendar day unless an acute, migraine-specific medication (i.e., triptan or ergot derivative) was used after the start of the headache, in which case no minimum duration is specified
OR
(D) Any headache which fulfills one criterion from (1) and at least one criterion from (2) OR fulfills at least two criteria from (1) and no criteria from (2):
  (1) Headache characteristics:
    (i) Unilateral location;
    (ii) Pulsating quality;
    (iii) Moderate or severe pain intensity;
    (iv) Aggravated by or causing avoidance of routine physical activity (e.g., walking or climbing stairs)
  (2) Symptoms
    (i) Nausea and/or vomiting;
    (ii) Photophobia and phonophobia;
    (iii) Typical aura (i.e., visual, sensory, or speech/language) accompanying or within sixty minutes before headache begins.
(E) Duration of headache lasting two hours or longer on a calendar day unless an acute, migraine-specific medication (i.e., triptan or ergot derivative) was used after the start of the headache, in which case no minimum duration is specified.

"Patient" means a human or non-human subject receiving or in need of medical or veterinary care. Accordingly, the compositions as disclosed herein can be used in treating any animal, such as, for example, mammals, or the like.

"Pharmaceutical composition" means a composition comprising an active pharmaceutical ingredient, such as, for example, a CGRP antagonist, and at least one additional ingredient, such as, for example, a stabilizer or excipient or the like. A pharmaceutical composition is therefore a formulation which is suitable for diagnostic or therapeutic administration to a subject, such as a human patient. The pharmaceutical composition can be, for example, in a lyophilized or vacuum dried condition, a solution formed after reconstitution of the lyophilized or vacuum dried pharmaceutical composition, or as a solution or solid which does not require reconstitution.

"Treating" means to alleviate (or to eliminate) at least one symptom of a condition or disorder, such as, for example, sinusitis, nausea, nasopharyngitis, photophobia, appetite changes, cognition and concentration difficulties, cold extremities, diarrhea or other bowel changes, excitement or irritability, fatigue, frequent urination, memory changes, weakness, yawning, stretching, seeing bright spots or flashes of light, vision loss, seeing dark spots, tingling sensations, speech problems, aphasia, tinnitus, gastric stasis, pulsating or throbbing pain on one or both sides of the head, extreme sensitivity to light, sounds, or smells, worsening pain during physical activity, and vomiting, abdominal pain or heartburn, loss of appetite, lightheadedness, blurred vision or fainting or the like, either temporarily or permanently.

The invention of the present disclosure will be more clearly understood by reference to the following examples, which are included for purposes of illustration only and are not intended to be limiting.

Example 1

Study A: A phase 3, multicenter, randomized, double-blind, placebo-controlled, parallel-group study was conducted to evaluate the efficacy, safety, and tolerability of oral atogepant for the prevention of migraine in participants with episodic migraine (EM).

This study comprised a 4-week screening and baseline period, a 12-week double-blind treatment period, and a 4-week follow-up period. The total study duration was 20 weeks.

Adults 18 to 80 years of age with 4 to 14 migraine days per month in the 3 months prior to visit 1, and 4 to 14 migraine days during the 28-day baseline period per electronic Diary, were allowed to enroll. Inclusion criteria included at least a 1-year history of migraine with or without aura consistent with a diagnosis, diagnosed as specified in the International Classification of Headache Disorders, 3rd edition, version (ICHD-3), and the age of the participant at the time of migraine onset was ≤50 years. Exclusion criteria included a history of migraine accompanied by diplopia or decreased level of consciousness or retinal migraine; a current diagnosis of chronic migraine, new persistent daily headache, trigeminal autonomic cephalgia (e.g., cluster headache), or painful cranial neuropathy as defined by ICHD-3, or if they averaged 15 or more migraine days per month across the 3 months prior to Visit 1 or during the 28-day baseline period; a history of an inadequate response to >4 medications (2 of which have different mechanisms of action) prescribed for the treatment of migraine; and participants with clinically significant hematologic, endocrine, cardiovascular, pulmonary, renal, hepatic, gastrointestinal, or neurologic disease. Use of opioids or barbiturate on more than 2 days per month, triptans or ergots on 10 or more days per month, or simple analgesics (e.g., aspirin, non-steroidal anti-inflammatory drugs, acetaminophen) on 15 or more days per month in the 3 months prior to Visit 1 or during the 28-day baseline period were also excluded. Use of barbiturates was also excluded 30 days prior to screening and throughout the duration of the trial.

Randomization was stratified based on prior exposure (yes/no) to a migraine prevention medication with proven efficacy, such as antiepileptics, tricyclic antidepressants, beta-blockers, calcium channel blocker, angiotensin receptor blocker or converting enzyme inhibitor, or serotonin-norepinephrine reuptake inhibitors. Approximately 70% of randomized participants took at least one prior migraine prevention medication with proven efficacy. Participants were not on concurrent medication during the study.

The trial included 910 randomized participants (223 to placebo, 222 to atogepant 10 mg, 230 to atogepant 30 mg, and 235 to atogepant 60 mg). The safety population included 902 participants and the modified-intent-to-treat population (efficacy analysis population) included 873 participants;

>87% of participants (805/910, 88.5%) completed the double-blind treatment period across all treatment groups. Baseline demographics and clinical characteristics were similar across treatment groups in the safety population. Participants were between 18 and 73 years of age, with a mean age of 41.6 years. 89% of participants were female, and 83% white, with a baseline BMI of 30.6 kg/m². At screening, 99.3% of participants reported use of medication for the acute treatment of migraine and 70.3% reported having previously used a preventive treatment for migraine, with or without proven efficacy. The baseline demographics of the safety population (i.e., all participants who received at least one dose of study intervention) are summarized in Table 1.

cebo 30 mg/atogepant 60 mg). Participants, site personnel, and trial sponsor personnel were blinded to the treatment assignment. Tablet formulations for CGRP compounds are described, for example, in U.S. Pat. No. 10,117,936.

Participants were allowed to take acute treatments for migraine which included triptans, ergot derivatives, opioids, acetaminophen, non-steroidal anti-inflammatory drugs, and antiemetic agents. Participants were not allowed to take any preventive treatments for migraine 30 days prior to visit 1 and throughout the trial.

Efficacy assessments were recorded by the participant in an electronic diary at home or via eTablet at the trial site during clinic visits. Headache duration, headache clinical features (headache pain severity, unilateral location, aggra-

TABLE 1

Baseline Demographics (Safety Population*)

| Baseline Demographics | | Placebo (N = 222) | Atogepant 10 mg QD (N = 221) | Atogepant 30 mg QD (N = 228) | Atogepant 60 mg QD (N = 231) | Total (N = 902) |
|---|---|---|---|---|---|---|
| Age | Mean (SD) (years) | 40.3 (12.81) | 41.4 (12.05) | 42.1 (11.68) | 42.5 (12.41) | 41.6 (12.25) |
| | Min, max | 18, 69 | 18, 73 | 19, 70 | 18, 72 | 18, 73 |
| Sex | Male | 24 (10.8) | 21 (9.5) | 24 (10.5) | 32 (13.9) | 101 (11.2) |
| | Female | 198 (89.2) | 200 (90.5) | 204 (89.5) | 199 (86.1) | 801 (88.8) |
| Race, n (%) ** | White | 194 (87.4) | 191 (81.9) | 195 (81.1) | 192 (83.1) | 752 (83.4) |
| | Black or African American | 24 (10.8) | 34 (15.4) | 38 (16.7) | 28 (12.1) | 124 (13.7) |
| | Asian | 2 (0.9) | 2 (0.9) | 1 (0.4) | 7 (3.0) | 12 (1.3) |
| | American Indian or Alaska Native | 0 (0.00) | 1 (0.5) | 1 (0.4) | 1 (0.4) | 3 (0.3) |
| | Multiple*** | 2 (0.9) | 3 (1.4) | 3 (1.3) | 2 (0.9) | 10 (1.1) |
| Ethnicity | Non-Hispanic | 89.6% | 90.5% | 91.7% | 93.9% | 91.5% |
| BMI | Mean (SD) (kg/m²) | 30.83 (8.713) | 30.35 (7.597) | 31.15 (7.631) | 29.91 (7.318) | 30.56 (7.828) |
| | Min, max | 16.9, 82.0 | 16.4, 60.3 | 17.1, 66.2 | 16.3, 57.3 | 16.3, 82.0 |
| Prior Exposure to a Migraine Prevention Medication with Proven Efficacy | Yes | 71.2% | 67.0% | 70.6% | 68.0% | 69.2% |
| Number of headache days per month in the last 3 months | Mean (SD) | 9.5 (2.8) | 9.3 (2.7) | 9.2 (2.7) | 9.1 (2.7) | 9.3 (2.7) |
| | Min, Max | 4, 14 | 4, 14 | 4, 14 | 4, 14 | 4, 14 |
| Number of migraine days per month in the last 3 months | Mean (SD) | 7.7 (2.6) | 7.2 (2.5) | 7.3 (2.4) | 7.3 (2.4) | 7.4 (2.5) |
| | Min, Max | 4, 14 | 4, 14 | 4, 14 | 4, 13 | 4, 14 |

*The safety population included all randomized participants who took at least 1 dose of trial treatment.
** Excludes one participant with missing data randomized to atogepant 60 mg.
***Only includes participants who reported multiple races A total of 910 patients were randomized 1:1:1:1 to one of the four treatment groups (10 mg QD, 30 mg QD, 60 mg QD, or placebo). Efficacy analyses were based on the Modified Intent-to-Treat Population (mITT) of 873 patients. The Modified Intent-to-Treat (mITT) Population includes all randomized participants who received at least one dose of study intervention, had an evaluable baseline period of eDiary data, and had at least one evaluable post-baseline 4-week period (Weeks 1 to 4, 5 to 8, and 9 to 12) of eDiary data during the double-blind treatment period.

All participants were instructed to take trial treatment orally at approximately the same time once daily for 12 weeks. To maintain the blinding, all participants took 3 tablets of trial treatment provided in identical blister cards: placebo (placebo 10 mg/placebo 30 mg/placebo 60 mg), atogepant 10 mg (atogepant 10 mg/placebo 30 mg/placebo 60 mg), atogepant 30 mg (placebo 10 mg, atogepant 30 mg, placebo 60 mg), and atogepant 60 mg (placebo 10 mg/plavated by or causing avoidance of routine physical activity), non-headache associated symptoms (nausea and/or vomiting; photophobia, phonophobia, and aura), and acute medication use were recorded. Additional health outcomes measures were collected.

The primary efficacy endpoint was change from baseline in mean monthly migraine days across the 12-week treatment period. Secondary efficacy endpoints, tested in hierarchical order, were change from baseline in mean monthly headache days across the 12-week treatment period, change from baseline in mean monthly acute medication use days across the 12 week treatment period, ≥50% reduction in 3-month average of monthly migraine days, change from baseline in MSQ v 2.1 Role Function-Restrictive domain score at week 12, change from baseline in mean monthly Performance of Daily Activities domain score of the AIM-D across the 12-week treatment period, and change from baseline in mean monthly Physical Impairment domain score of the AIM-D across the 12-week treatment period. An exploratory analysis of the time course of efficacy for atogepant by 4-week intervals, based on the least square mean change from baseline for the number of monthly migraine days over the 12-week treatment period was also conducted.

Figure 2:
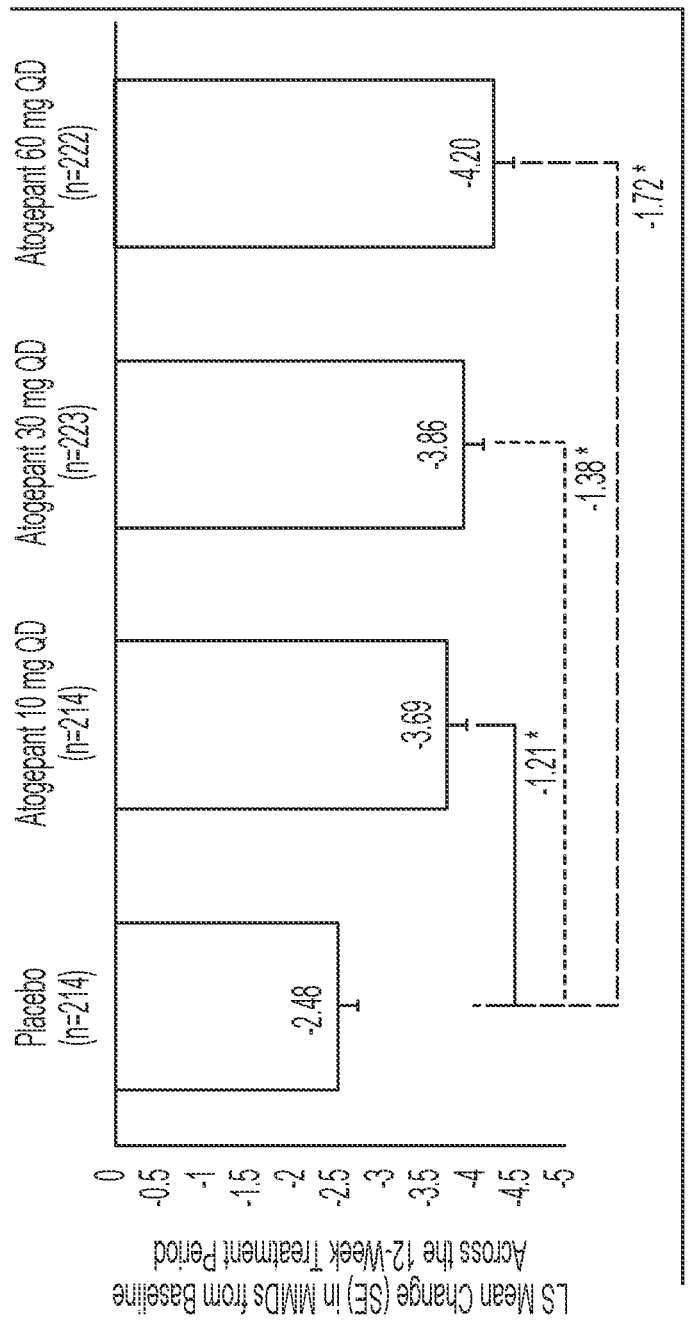
Figure 3:
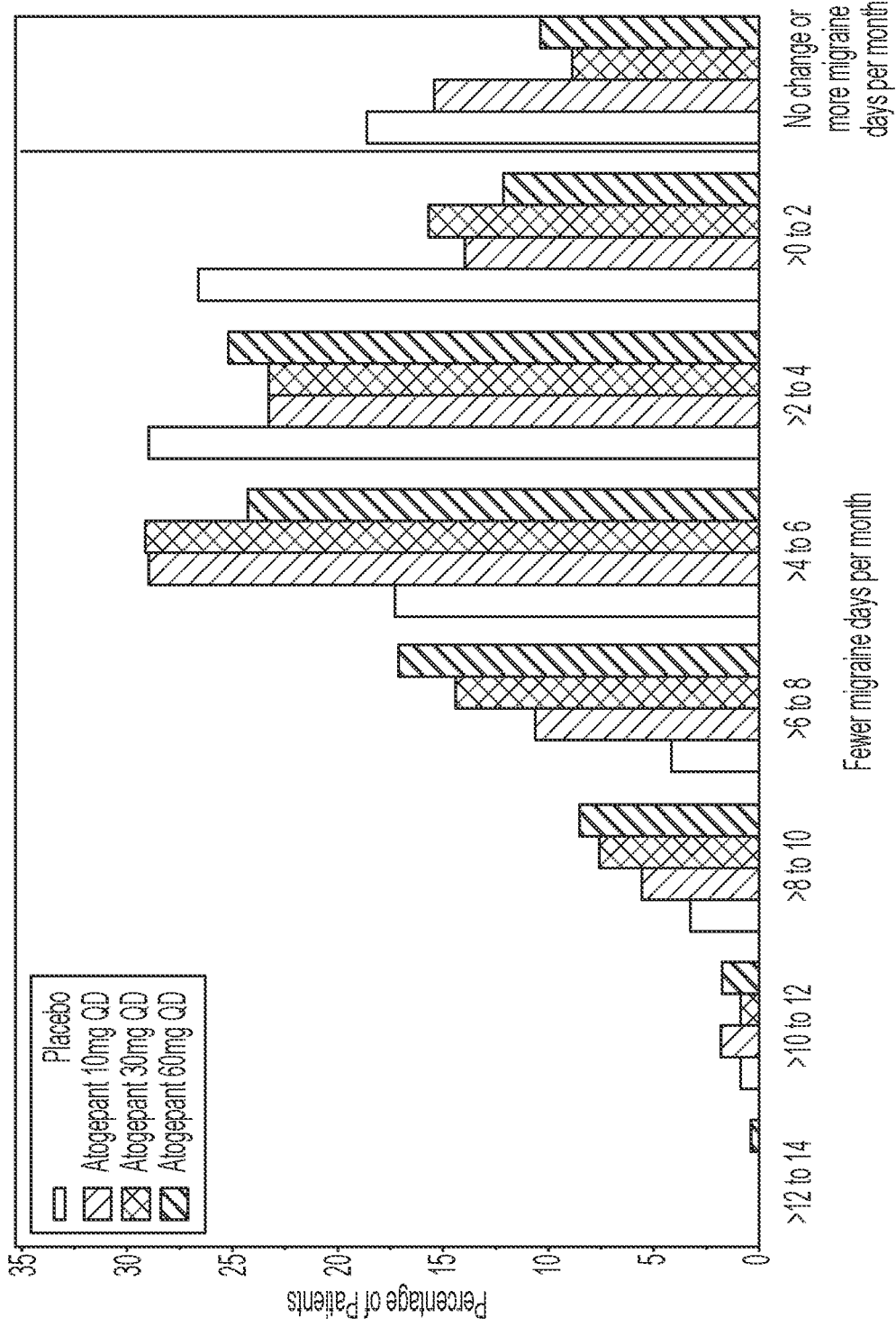
FIG. 3 shows the distribution of change from baseline in monthly migraine days across 12 weeks by treatment group. A treatment benefit over placebo for all doses of atogepant is seen across a range of changes from baseline in mean monthly migraine days.

The primary efficacy variable was the change from baseline in mean monthly migraine days across the 12-week treatment period. The results are shown in Table 2. FIGS. 1 and 2 show the least square mean (+/−standard error of the least squares (SE)) of change from baseline in monthly migraine days (MMRM—mixed effects model for repeated measures) during the double-blind treatment period for the mITT population. FIG. 3 shows the distribution of change from baseline in monthly migraine days across 12 weeks by treatment group.

During the 28-day baseline period, the mean weekly migraine days were 1.9 in the overall mITT population. Mean change from baseline in weekly migraine days during the first week of treatment was −0.77 atogepant 10 mg, −0.94 atogepant 30 mg, −1.03 atogepant 60 mg, and −0.29 placebo (P≤0.0001 all dose groups). The greater reduction in weekly migraine days compared with placebo was consistent throughout each week of the first 4-week interval of treatment (P≤0.0397 all dose groups). On the first full day after study drug administration, the proportion of participants who reported a migraine day was 14.1% for atogepant 10 mg, 10.8% for atogepant 30 mg, and 12.3% for atogepant 60 mg versus 25.2% in the placebo group (P≤0.0071 all dose groups). The proportions of participants with a migraine each day during the first week of treatment (mITT popula-

TABLE 2

Primary Endpoint - Change from Baseline in Mean Monthly Migraine Days Across the 12-Week Treatment Period (mITT Population)

|  | Placebo (N = 214) | Atogepant 10 mg QD (N = 214) | Atogepant 30 mg QD (N = 223) | Atogepant 60 mg QD (N = 222) |
| --- | --- | --- | --- | --- |
| Baseline number of monthly migraine days, mean (SD) | 7.51 (2.39) | 7.45 (2.46) | 7.86 (2.32) | 7.75 (2.31) |
| LS Mean Change (SE) | −2.48 (0.21) | −3.69 (0.21) | −3.86 (0.21) | −4.20 (0.21) |
| LSMD vs. Placebo (95% CI) | — | −1.21 (−1.78, −0.64) | −1.38 (−1.94, −0.82) | −1.72 (−2.28, −1.15) |
| Nominal p-value | — | <.0001 | <.0001 | <.0001 |
| Adjusted p-value | — | <.0001 | <.0001 | <.0001 |

SD—Standard Deviation; LS—Least Squares; SE—Standard error of the least squares; CI—Confidence Interval; LSMD—least squares mean difference.

As shown in Table 2 and FIGS. 1, 2, and 3, all atogepant dose groups met the primary endpoint and demonstrated statistically significantly greater decreases in monthly migraine days compared to placebo. Patients treated in the 10 mg, 30 mg, and 60 mg atogepant arms experienced a decrease of 3.69, 3.86, and 4.20 days, respectively, all compared to patients in the placebo arm, who experienced a decrease of 2.48 days (all dose groups vs. placebo, p=<0.0001).

Figure 4:
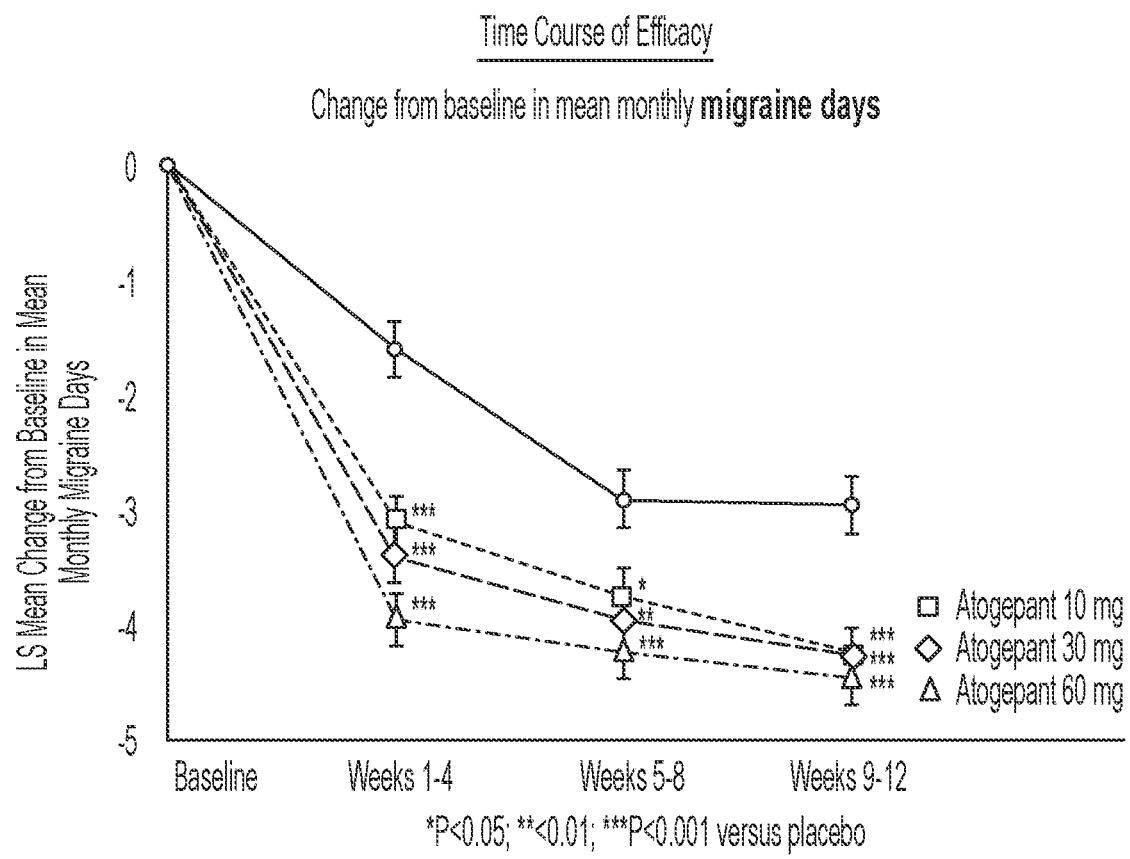
FIG. 4 shows the LS mean change from baseline in monthly migraine days across 12 weeks by treatment group.
Figure 5A:
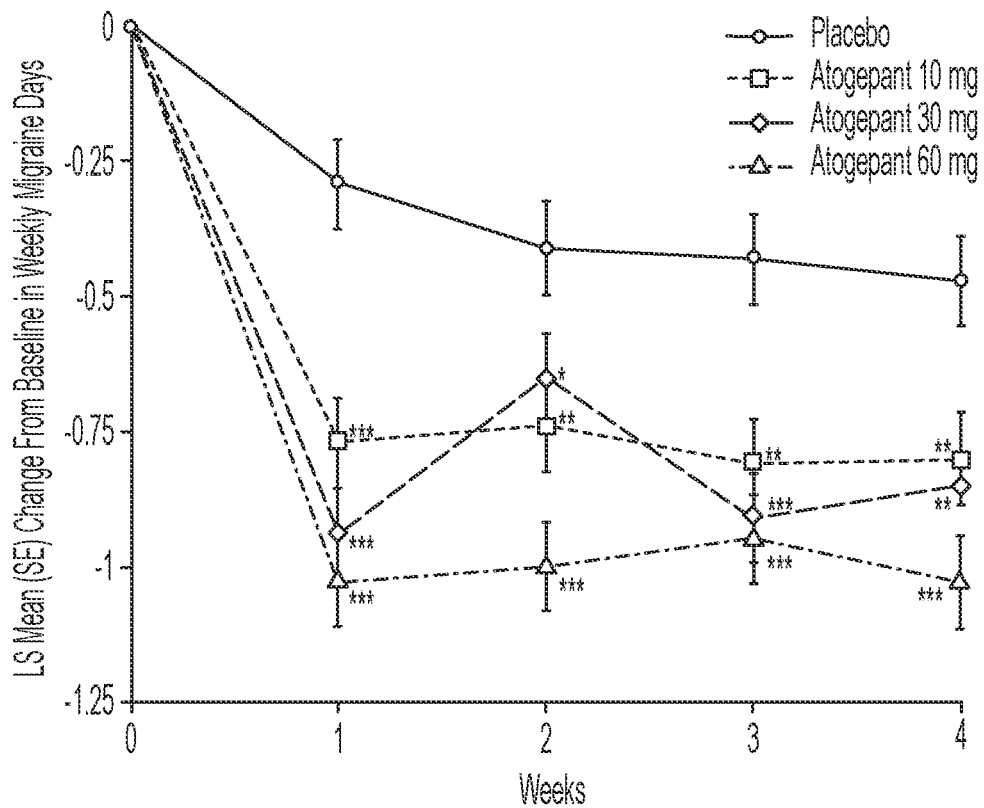
FIG. 5A shows the mean change from baseline in weekly migraine days during the first month (weeks 1-4) by treatment group.
Figure 5B:
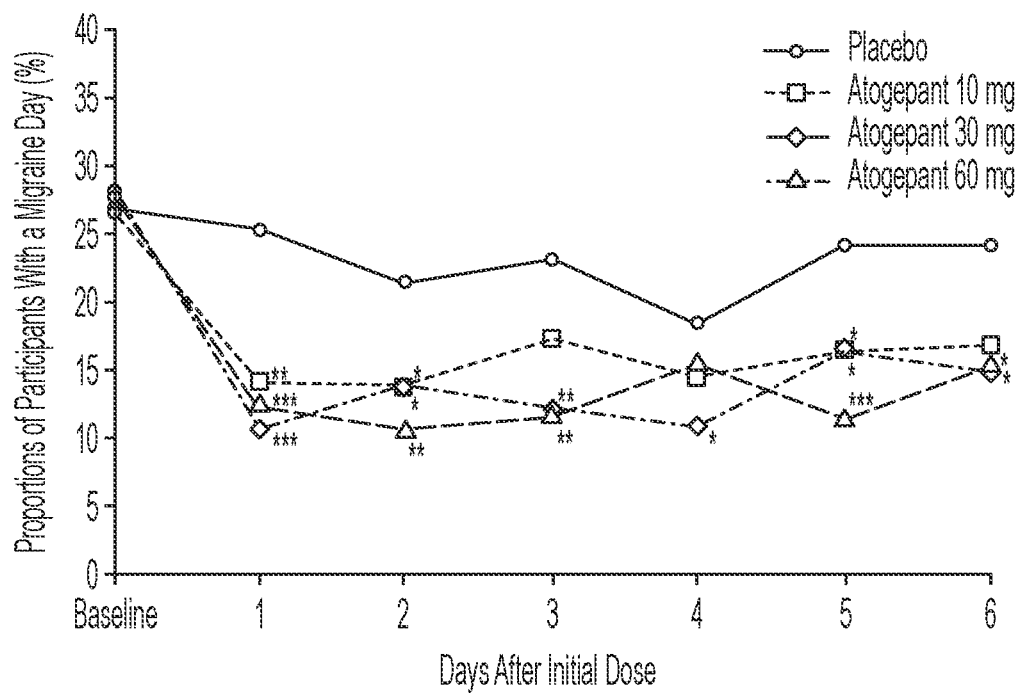
FIG. 5B shows the proportion of participants with a migraine each day during the first week of treatment (mITT population). Atogepant provided an early and sustained reduction in migraine days including statistically significant reductions in each of the three 4-week intervals, each week during the first 4-week interval, and as early as the first full day after study drug initiation.

The LS mean change from baseline in monthly migraine days across 12 weeks by treatment group is shown in FIG. 4. FIG. 5A shows the mean change from baseline in weekly migraine days during the first month (weeks 1-4) by treatment group. During weeks 1-4 of treatment, mean change from baseline in mean monthly migraine days was −3.1 for atogepant 10 mg, −3.4 for atogepant 30 mg, −3.9 for atogepant 60 mg, and −1.6 for placebo. This significantly greater decrease in monthly migraine days was maintained during the subsequent two 4-week intervals of double-blind treatment for all atogepant doses (weeks 5-8: −3.7 for atogepant 10 mg, −3.9 for atogepant 30 mg, −4.2 for atogepant 60 mg, and −2.9 for placebo, P≤0.012 for all atogepant groups; weeks 9-12: −4.2 for atogepant 10 mg, −4.3 for atogepant 30 mg, −4.4 for atogepant 60 mg, and −3.0 for placebo, P≤0.0002 for all atogepant groups).

tion) are shown in FIG. 5B. On post dose days 2-6, the proportions of participants reporting a migraine was consistently lower across the treatment groups compared with placebo, with the majority of days reaching significance vs. placebo (P≤0.05) in the atogepant 30 mg and 60 mg dose groups. The odds ratio vs placebo for reporting a migraine on post dose day 1 was 0.49 with atogepant 10 mg, 0.33 with atogepant 30 mg, and 0.39 with atogepant 60 mg. Atogepant provided an early and sustained reduction in migraine days including statistically significant reductions in each of the three 4-week intervals, each week during the first 4-week interval, and as early as the first full day after study drug initiation.

Figure 6:
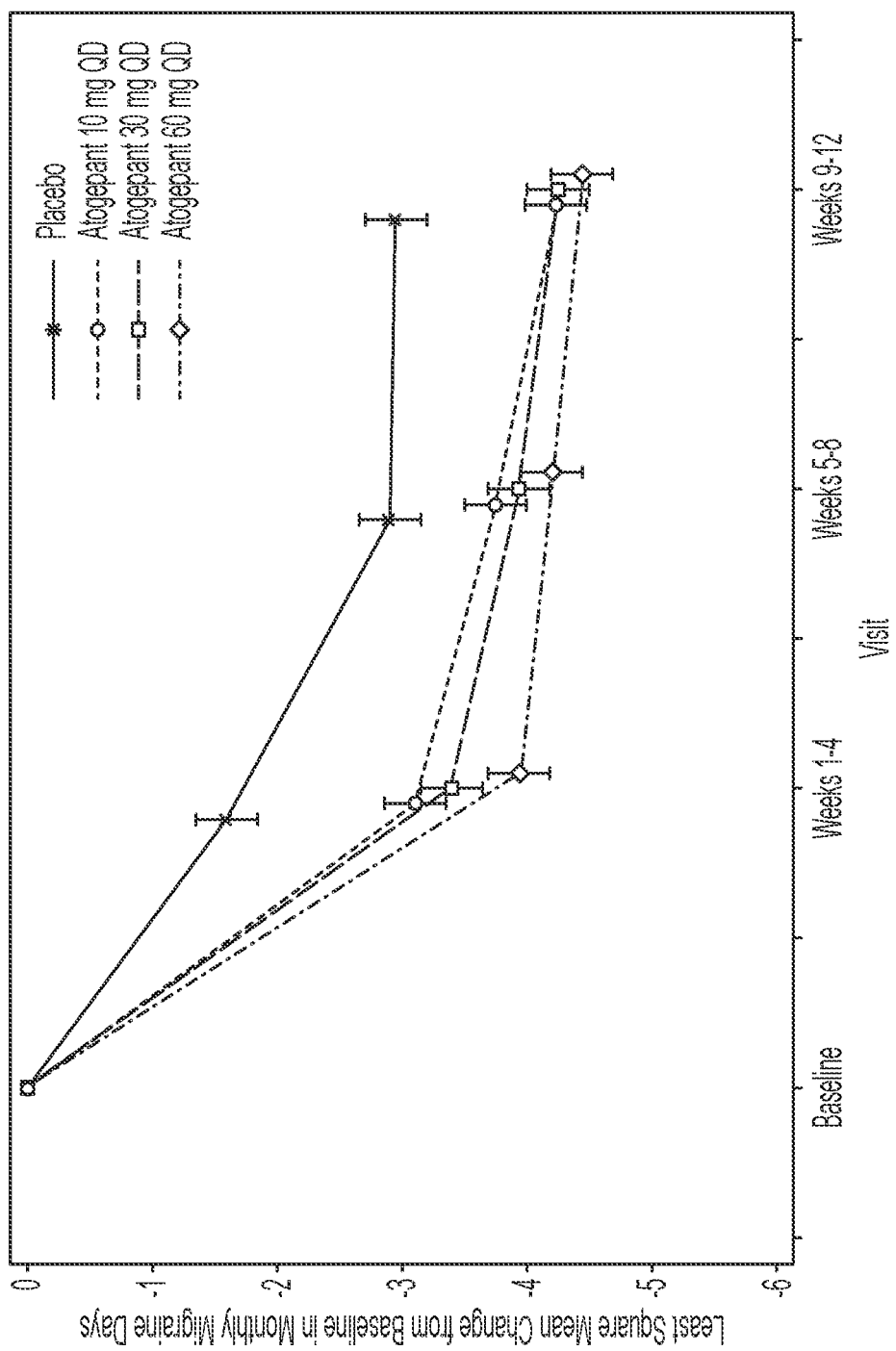
FIG. 6 shows the response profile for percent reduction from baseline in 3-month average of monthly migraine days for the mITT population.
Figure 7:
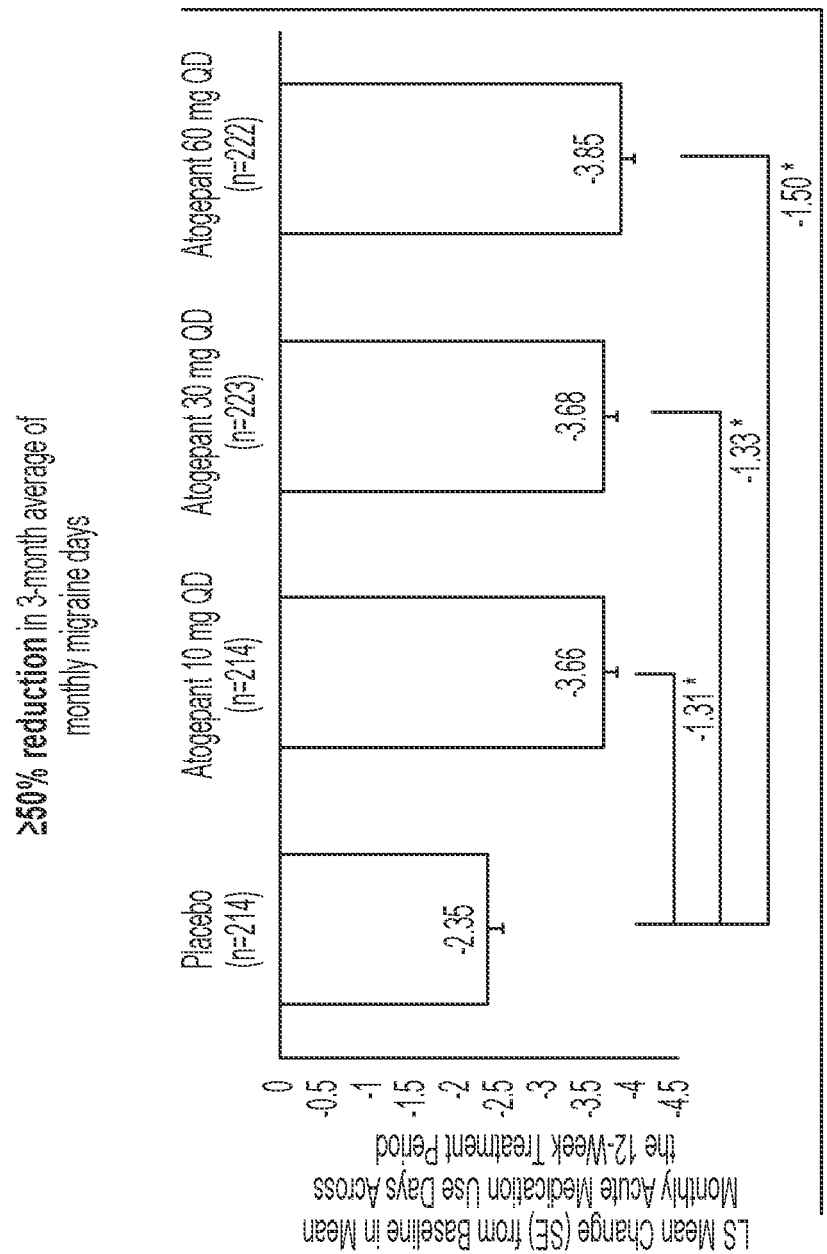
FIG. 7 shows the percent of participants with a ≥50% reduction in 3-month average monthly migraine days (MMDs) for placebo, atogepant 10 mg, atogepant 30 mg, and atogepant 60 mg. With respect to the proportion of patients who achieved a ≥50% reduction in their 3-month average of monthly migraine days, all three atogepant doses had a significantly greater 50% responder rate versus placebo, with nearly double the proportion of responders achieving at least a 50% reduction in monthly migraine days across all doses when compared to placebo.

A secondary endpoint measured the proportion of patients that achieved a 50% reduction in mean monthly migraine days across the 12-week treatment period. The results are shown in Table 3. The response profile for percent reduction from baseline in 3-month average of monthly migraine days (mITT population) is set forth in FIGS. 6 and 7. In particular, FIG. 6 shows the response profile for percent reduction from baseline in 3-month average of monthly migraine days for the mITT population. FIG. 7 shows the percent of participants with a ≥50% reduction in 3-month average monthly migraine days.

TABLE 3

≥50% Reduction in 3-Month Average of Monthly Migraine Days (mITT Population)

|  | Placebo (N = 214) | Atogepant 10 mg QD (N = 214) | Atogepant 30 mg QD (N = 223) | Atogepant 60 mg QD (N = 222) |
| --- | --- | --- | --- | --- |
| Responder, n (%) | 62 (29.0) | 119 (55.6) | 131 (58.7) | 135 (60.8) |
| Odds ratio vs. Placebo (95% CI) | — | 3.06 (2.05, 4.56) | 3.53 (2.37, 5.26) | 3.82 (2.56, 5.71) |
| Nominal p-value | — | <.0001 | <.0001 | <.0001 |
| Adjusted p-value | — | <.0001 | <.0001 | <.0001 |

CI—confidence interval

As shown in Table 3, 55.6%, 58.7%, and 60.8% of patients in the 10 mg, 30 mg, and 60 mg atogepant arms, respectively, achieved at least a 50% reduction in mean monthly migraine days across the 12-week treatment period, compared to 29% of patients in the placebo arm (all dose groups vs. placebo, p=≤0.0001).

Figure 8A:
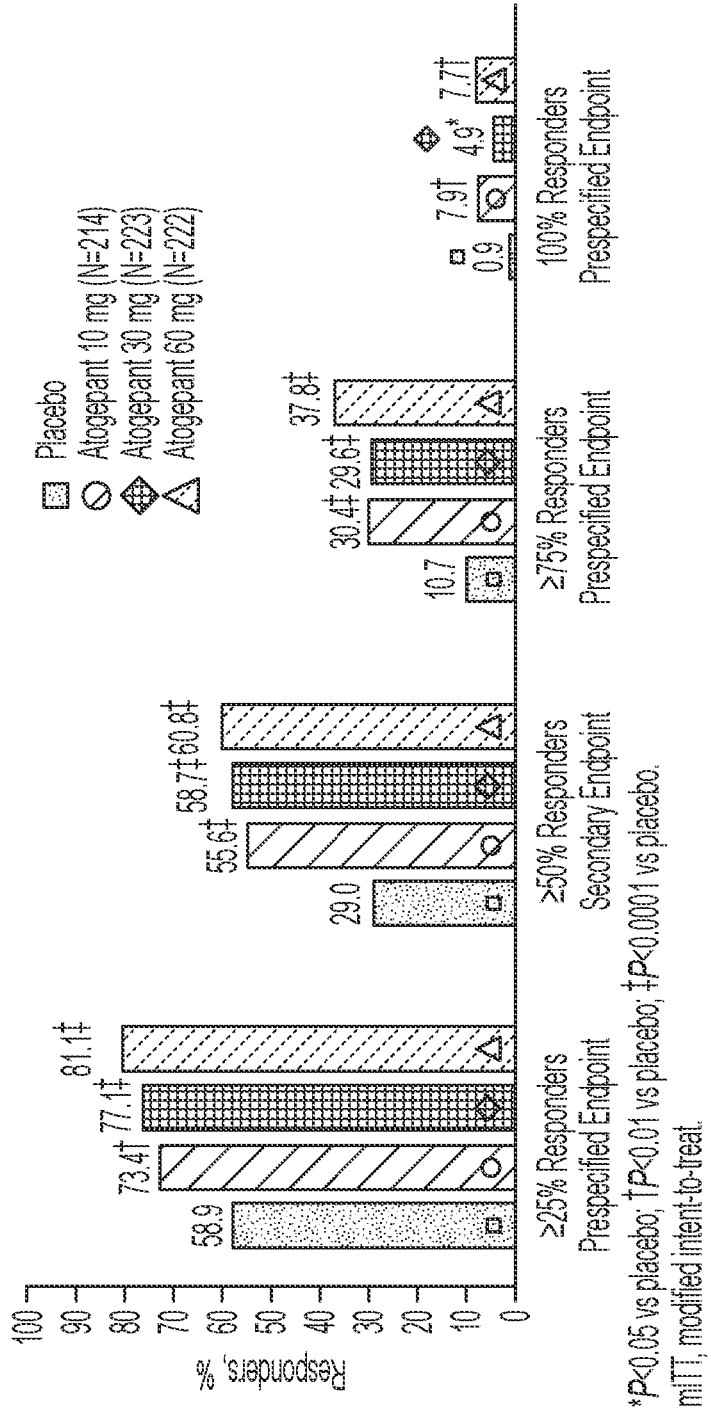
FIG. 8A shows the proportion of participants achieving ≥25%, ≥50%, ≥75%, and 100% responder rates in the 12-week average of monthly migraine days.

Prespecified additional endpoints included proportions of participants achieving ≥25%, ≥75%, and 100% reductions in the 12-week average of MMDs. A 100% reduction in MMDs represented individuals reporting no migraine days from the day the participant received the first dose of study treatment (day 1) through the end of week 12. The results are shown in Tables 4-6. FIG. 8A illustrates the proportion or participants achieving various responder rates by treatment group across the 12-week treatment period.

TABLE 4

≥25% Reduction in 3-Month Average of Monthly Migraine Days

|  | Placebo (N = 214) | Atogepant 10 mg QD (N = 214) | Atogepant 30 mg QD (N = 223) | Atogepant 60 mg QD (N = 222) |
| --- | --- | --- | --- | --- |
| Responder, n (%) | 126 (58.9) | 157 (73.4) | 172 (77.1) | 180 (81.1) |

P < .0018 for all comparisons

TABLE 5

≥75 Reduction in 3-Month Average of Monthly Migraine Days

|  | Placebo (N = 214) | Atogepant 10 mg QD (N = 214) | Atogepant 30 mg QD (N = 223) | Atogepant 60 mg QD (N = 222) |
| --- | --- | --- | --- | --- |
| Responder, n (%) | 23 (10.7) | 65 (30.4) | 66 (29.6) | 84 (37.8) |

P < .0001 for all comparisons

TABLE 6

100% Reduction in 3-Month Average of Monthly Migraine Days

|  | Placebo (N = 214) | Atogepant 10 mg QD (N = 214) | Atogepant 30 mg QD (N = 223) | Atogepant 60 mg QD (N = 222) |
| --- | --- | --- | --- | --- |
| Responder, n (%) | 2 (0.9) | 17 (7.9) | 11 (4.0) | 17 (7.7) |

P < .0207 for all comparisons

Atogepant-treated participants were significantly more likely to experience a ≥50% reduction in mean MMDs across 12 weeks (range 56%-61% vs 29% with placebo, P≤0.0001). Atogepant treated patients were also significantly more likely than placebo-treated participants to experience ≥25% (range 73%-81% vs 59% for placebo, P≤0.01), ≥75% (range 30%-38% vs 11% for placebo, P≤0.0001), and 100% (range 5%-8%, vs 1% for placebo, P≤0.05) reductions in MMDs across 12 weeks.

Figure 8B:
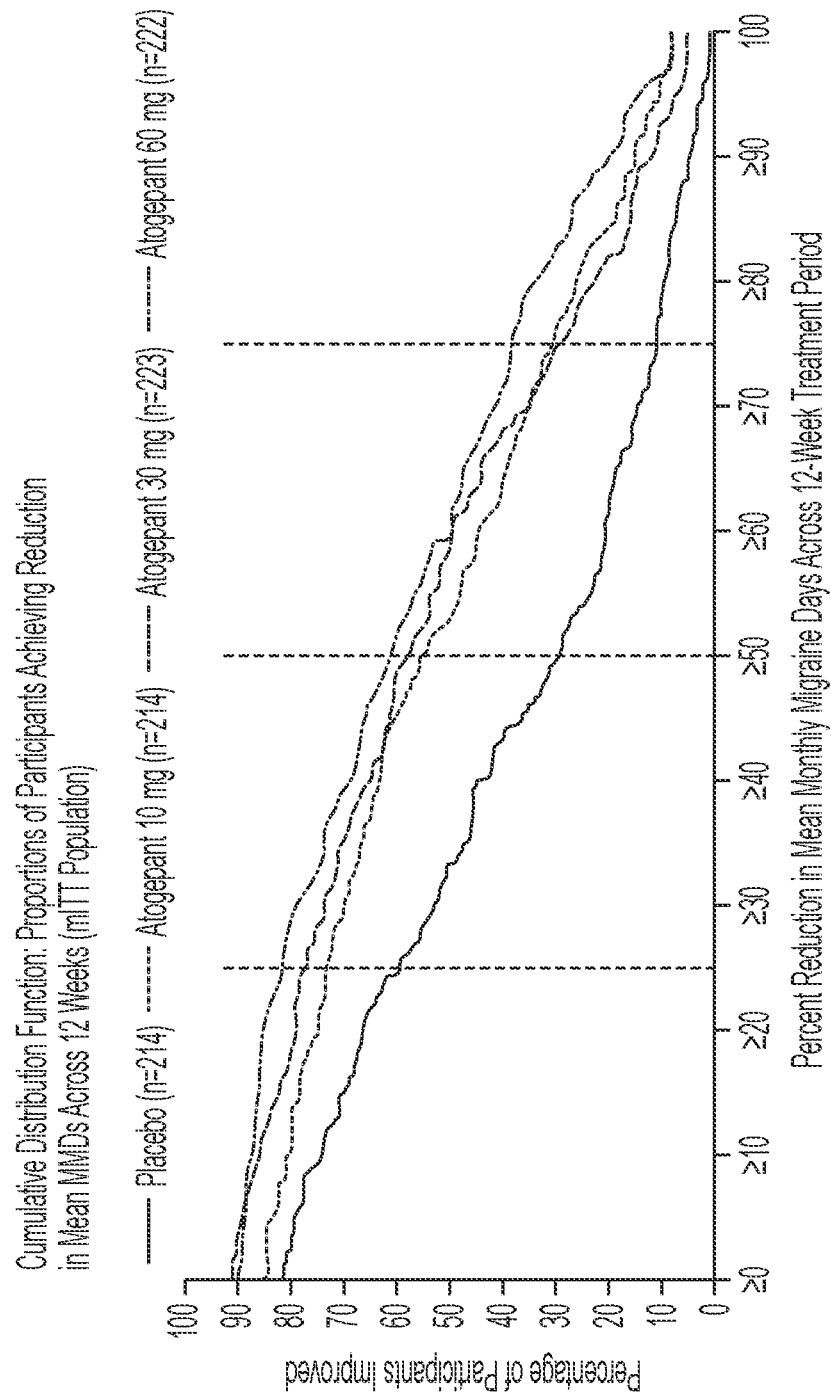
FIG. 8B shows a cumulative distribution function graph of the percent reduction from baseline in 12-week average MMDs.

FIG. 8B provides a cumulative distribution function graph of the percent reduction from baseline in 12-week average MMDs. As shown in FIG. 8B, response rates were better for each of the three atogepant groups vs. placebo. A consistently higher proportion of participants in each of the three atogepant groups showed improvement in 12-week average MMDs compared with placebo across all levels of improvement that were evaluated.

Figure 8C:
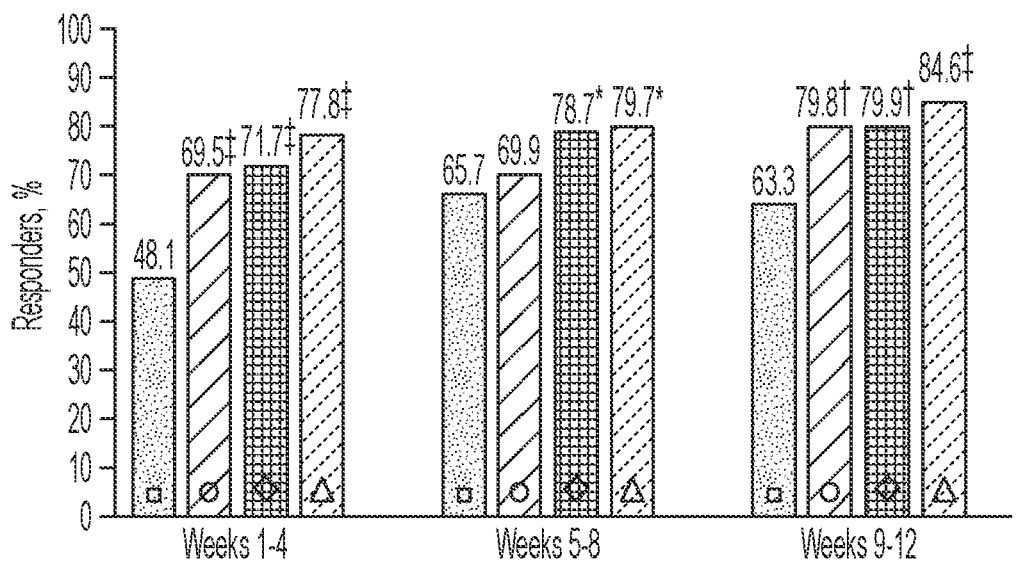
FIG. 8C shows the proportion of participants with ≥25% reduction in mean monthly migraine days.
Figure 8D:
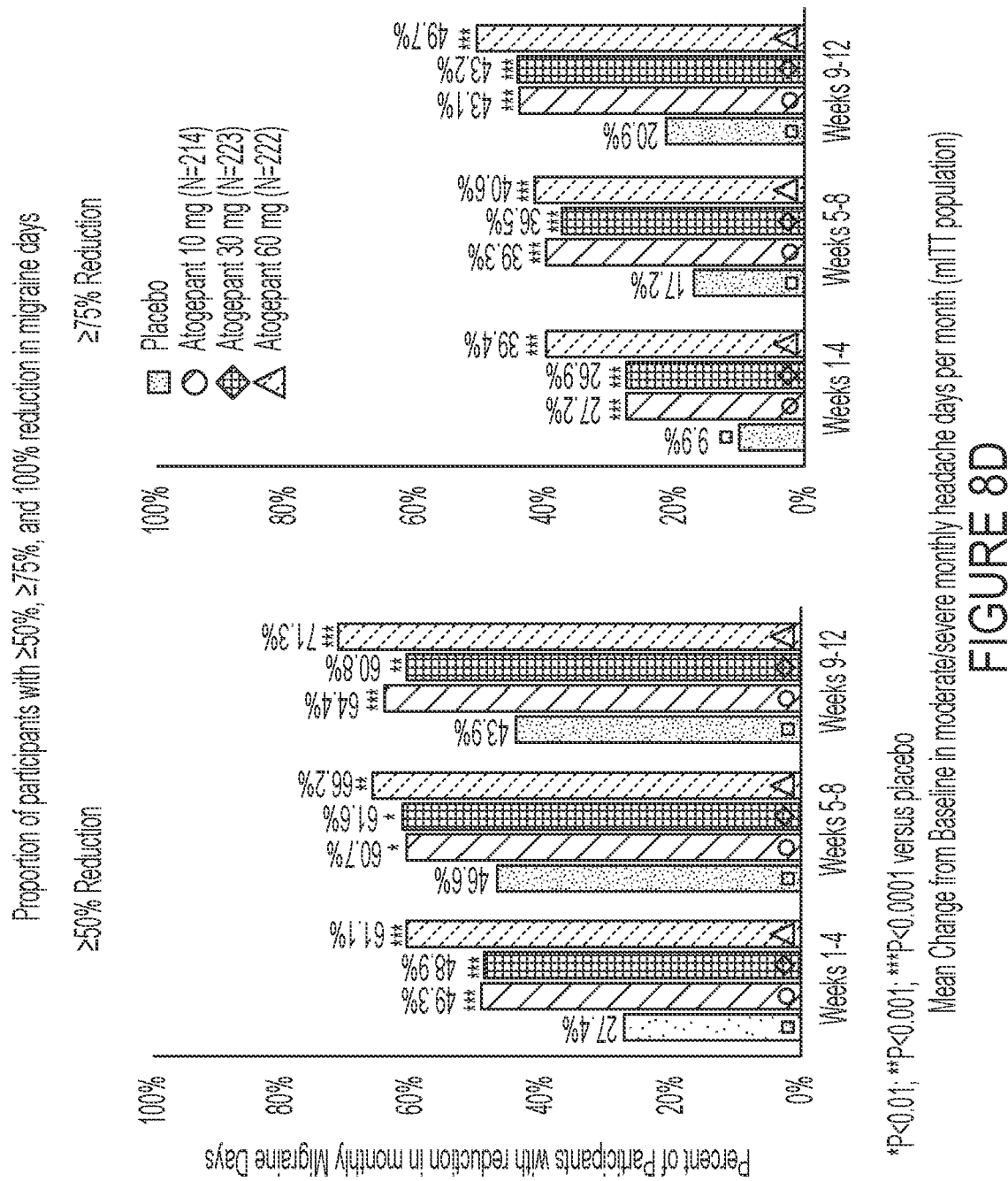
FIG. 8D shows the proportion of participants with ≥50%, ≥75%, and 100% reduction in monthly migraine days for month 1 (weeks 1-4), month 2 (weeks 5-8), and month 3 (weeks 9-12) across the 12-week treatment period.
Figure 8D:
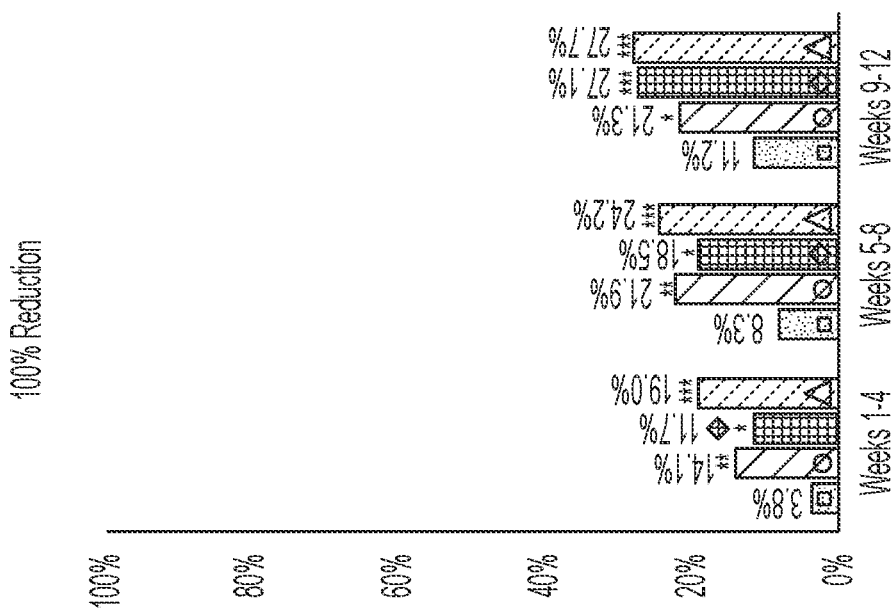

Additional prespecified exploratory endpoints included ≥25%, ≥50%, ≥75%, and 100% reductions in MMDs by 4-week intervals (weeks 1-4, 5-8, 9-12). FIG. 8C shows the proportion of participants with ≥25% reduction in mean monthly migraine days, and 8D shows the proportion of participants with ≥50%, ≥75%, and 100% reduction in monthly migraine days across the 12-week treatment period, for month 1 (weeks 1-4), month 2 (weeks 5-8) and month 3 (weeks 9-12). Response to atogepant treatment was evident as early as the first four weeks of treatment and increased over time. All differences for ≥50%, ≥75%, and 100% responder rates by 4-week intervals were statistically significant in favor of atogepant. For ≥25% responder rates, all differences were statistically significant in favor of atogepant vs placebo, except for atogepant 10 mg for weeks 5-8.

Relative to placebo, atogepant treated participants were ≥3 times more likely to achieve ≥50% reduction in the 12-week average of MMDs. At all doses, atogepant was effective in the first 4 weeks for ≥25%, ≥50%, ≥75%, and 100% responders, suggesting robust treatment effects in the first month. The proportion of participants experiencing a ≥25%, ≥50%, ≥75%, and 100% reduction in mean MMDs significantly increased with duration of treatment for all atogepant doses and efficacy was sustained for three months, noting that placebo response rates also increased throughout the study period. The responder rates were higher with increasing doses among the atogepant treatment groups.

A secondary endpoint measured the change from baseline in mean monthly headache days across the 12-week treatment period. The results are shown in Table 7.

TABLE 7

Change from Baseline in Mean Monthly Headache Days across the 12-Week Treatment Period (mITT Population)

|  | Placebo (N = 214) | Atogepant 10 mg QD (N = 214) | Atogepant 30 mg QD (N = 223) | Atogepant 60 mg QD (N = 222) |
|---|---|---|---|---|
| Baseline number of mean monthly headache days, mean (SD) | 8.43 (2.55) | 8.41 (2.75) | 8.78 (2.62) | 9.00 (2.56) |
| LS Mean Change (SE) | −2.52 (0.23) | −3.94 (0.22) | −4.04 (0.22) | −4.23 (0.22) |
| LSMD vs. Placebo (95% CI) | — | −1.42 (−2.03, −0.81) | −1.53 (−2.13, −0.92) | −1.71 (−2.32, −1.10) |
| Nominal p-value | — | <.0001 | <.0001 | <.0001 |
| Adjusted p-value | — | <.0001 | <.0001 | <.0001 |

SD—Standard Deviation; LS—Least Squares; SE—Standard error of the least squares; CI—Confidence Interval; LSMD—least squares mean difference.

As shown in Table 7, patients in the 10 mg, 30 mg, and 60 mg atogepant arms experienced a decrease of 3.94, 4.04, and 4.23 days, respectively, all compared to patients in the placebo arm, who experienced a decrease of 2.52 days (all dose groups vs. placebo, p=≤0.0001).

Figure 9A:
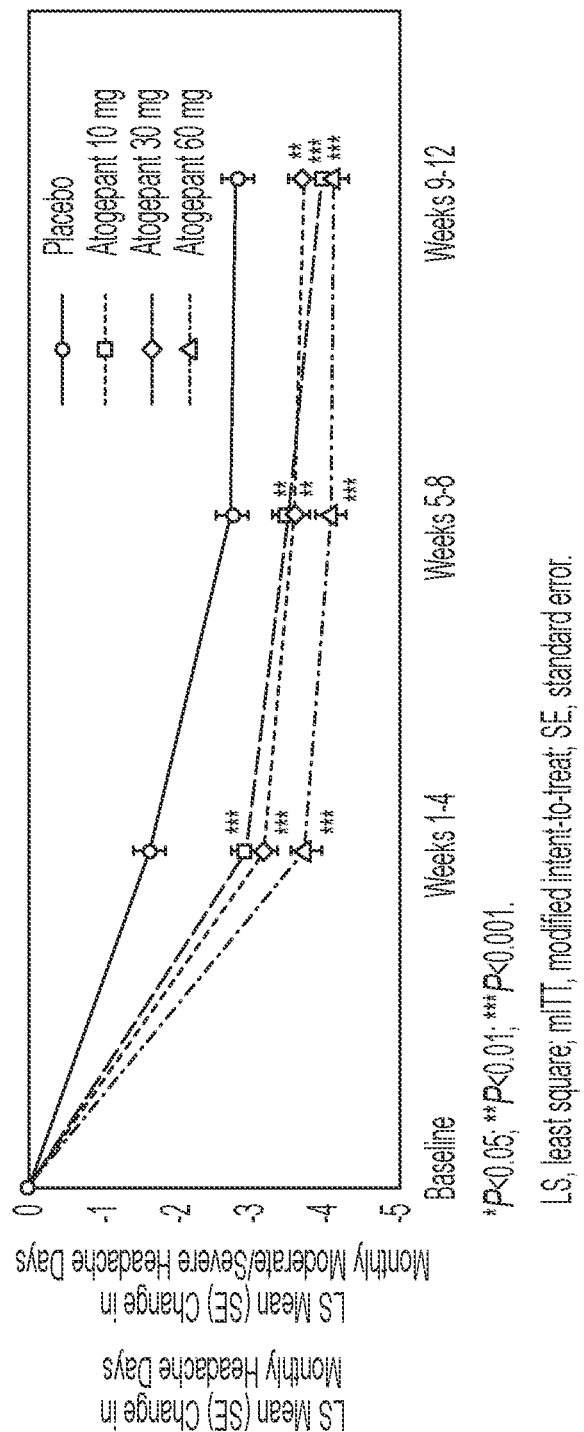
FIG. 9A shows the mean change from baseline in moderate/severe headache days per month (mITT population).
Figure 9B:
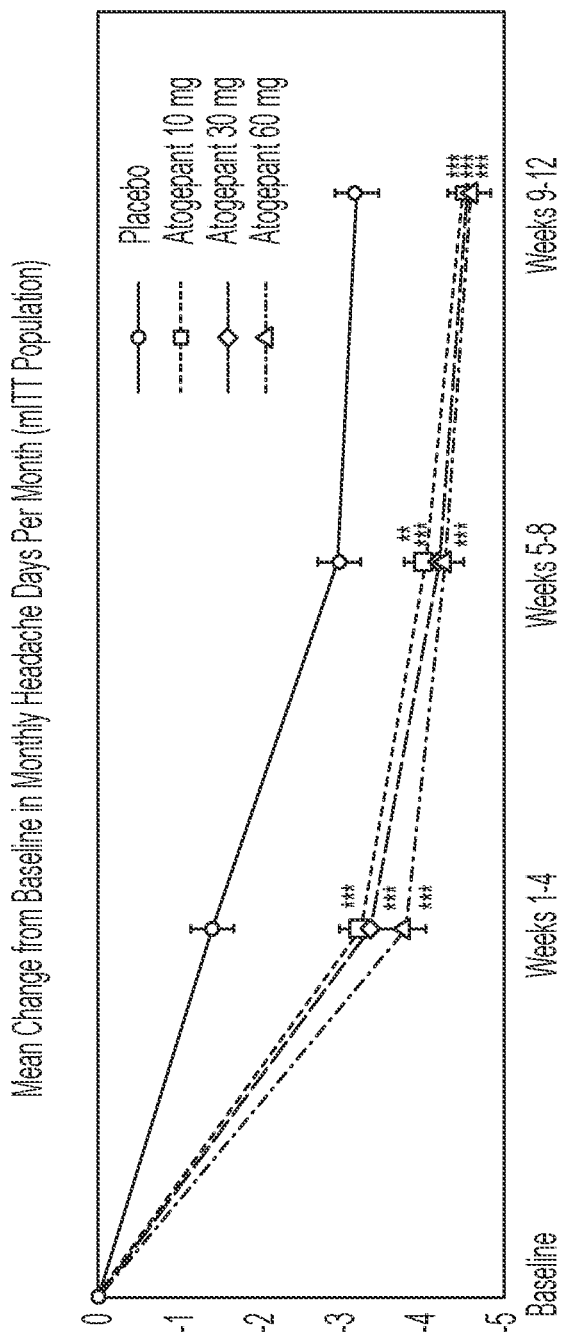
FIG. 9B shows the mean change from baseline in monthly headache days per month.

The mean change from baseline in moderate/severe headache days per month (mITT population) is shown in FIG. 9A, and the mean change from baseline in monthly headache days per month (mITT population) is shown in FIG. 9B. The LS mean change from baseline in moderate/severe headache days in the first treatment period (weeks 1-4) was −3.0 for atogepant 10 mg, −3.2 for atogepant 30 mg, −3.8 for atogepant 60 mg, and −1.7 for placebo (P≤0.0001 for all atogepant groups). The LS mean change from baseline in mean headache days in the first treatment period was −3.2 for atogepant 10 mg, −3.4 for atogepant 30 mg, −3.8 for atogepant 60 mg, and −1.4 for placebo (P≤0.0001 for all atogepant groups).

A secondary endpoint measured change from baseline in mean monthly acute medication use days across the 12-week treatment period. The results are shown in Table 8 and FIG. 10A.

Figure 10A:
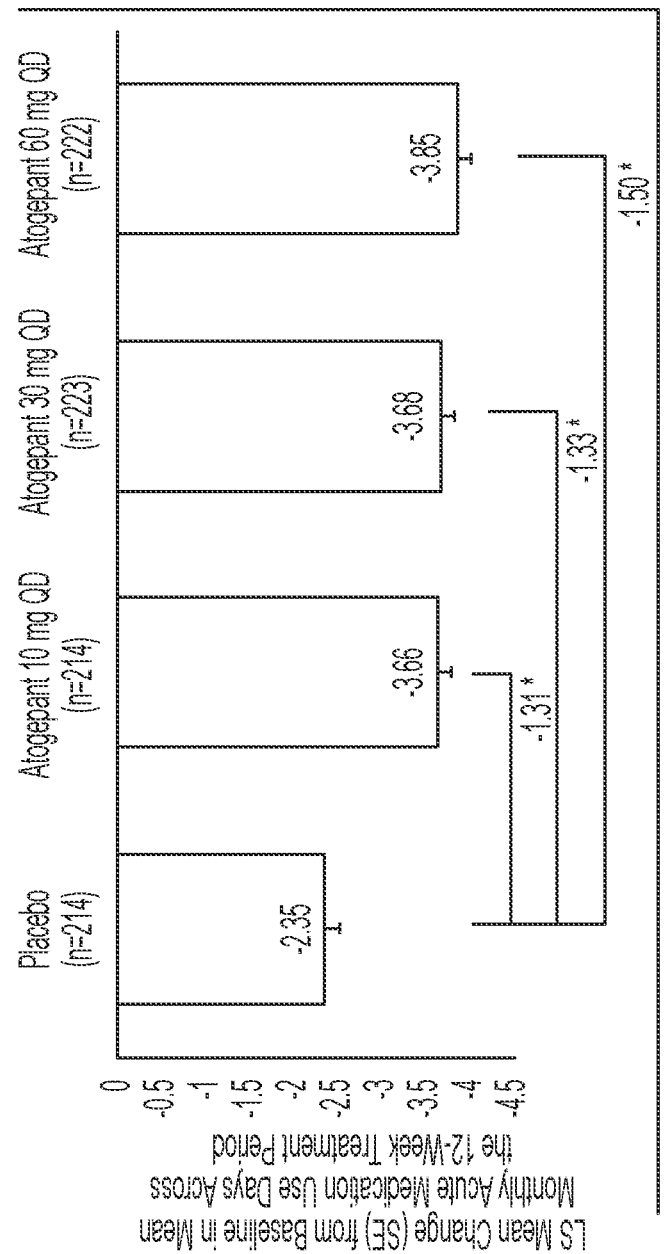
FIG. 10A shows the LS mean change (SE) from baseline in mean monthly acute medication use days across the 12-week treatment period for atogepant 10 mg, atogepant 30 mg, atogepant 60 mg, and placebo.

As shown in Table 8 and FIG. 10A, patients in the 10 mg, 30 mg, and 60 mg atogepant arms experienced a decrease of 3.66, 3.68, and 3.85 days, respectively, across the 12-week treatment period compared to patients in the placebo arm, who experienced a decrease of 2.35 days (all dose groups vs. placebo, p=≤0.0001).

Figure 10B:
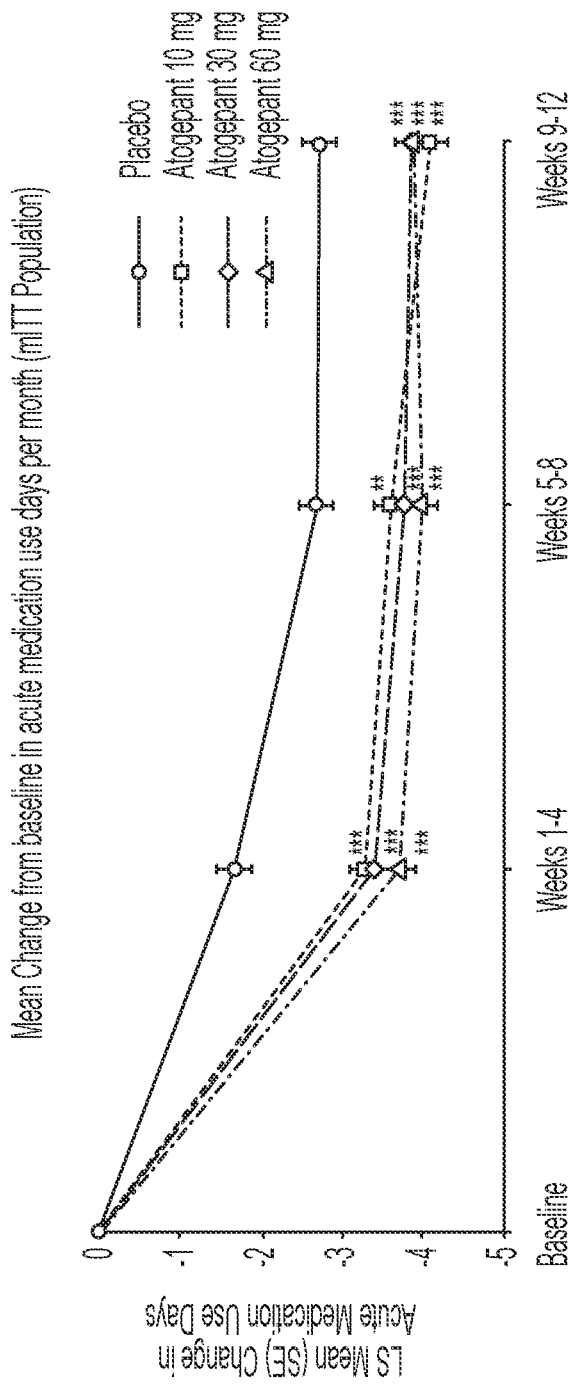
FIG. 10B shows the LS mean change from baseline in acute medication use days during the first treatment period (weeks 1-4), second treatment period (weeks 5-8) and third treatment period (weeks 9-12) for atogepant 10 mg, atogepant 30 mg, atogepant 60 mg, and placebo.
Figure 10C:
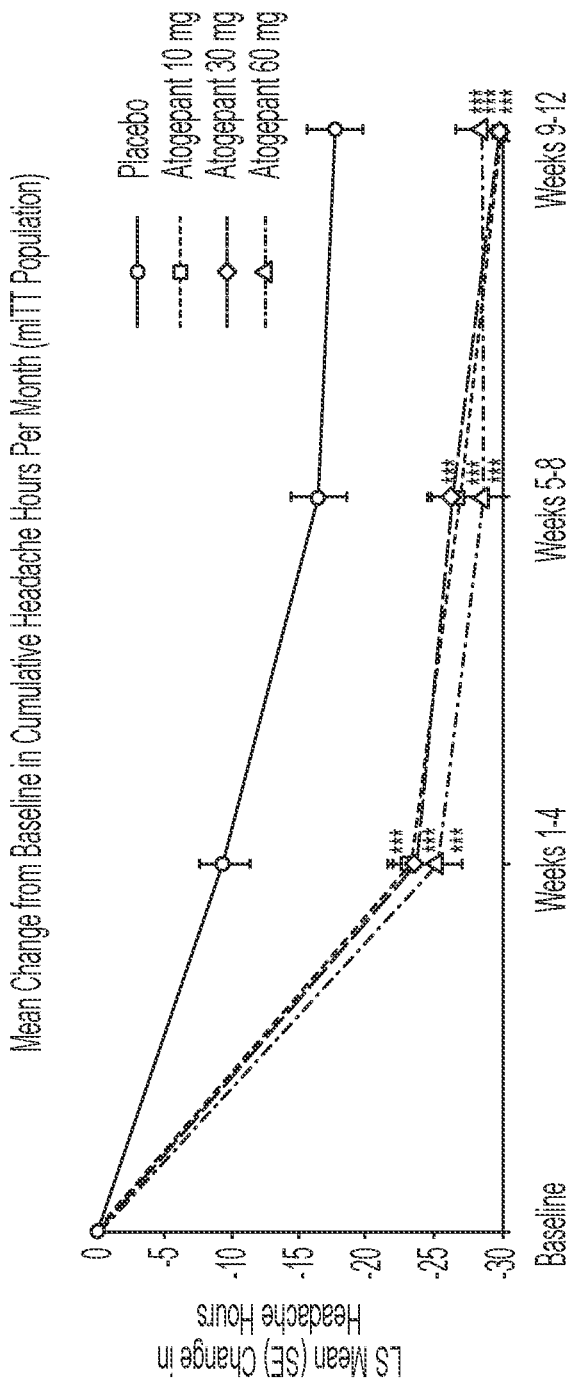
FIG. 10C shows the LS mean reduction from baseline in mean cumulative headache hours during the first treatment period (weeks 1-4), second treatment period (weeks 5-8) and third treatment period (weeks 9-12) for atogepant 10 mg, atogepant 30 mg, atogepant 60 mg, and placebo.

The LS mean change from baseline in acute medication use days during the first treatment period (weeks 1-4) was −3.3 for atogepant 10 mg, −3.4 for atogepant 30 mg, −3.7 for atogepant 60 mg, and −1.7 for placebo (P≤0.0001 for all atogepant groups). The LS mean change in acute medication use days showed a nominally significant difference from placebo starting in the first treatment period and persisting into the second and third treatment periods, as shown in FIG. 10B. Baseline mean cumulative headache hours ranged from 47.4-51.1 in the mITT population. The LS mean reduction from baseline in mean cumulative headache hours during the first treatment period was −23.3 for atogepant 10 mg, −23.6 for atogepant 30 mg, −25.1 for atogepant 60 mg, and −9.5 for placebo (P≤0.0001 for all atogepant groups). LS mean reduction from baseline in mean cumulative headache hours is illustrated in FIG. 10C.

TABLE 8

Change from Baseline in Mean Monthly Acute Medication Use Days Across the 12-Week Treatment Period (mITT Population)

|  | Placebo (N = 214) | Atogepant 10 mg QD (N = 214) | Atogepant 30 mg QD (N = 223) | Atogepant 60 mg QD (N = 222) |
|---|---|---|---|---|
| Baseline number of monthly acute medication use days, mean (SD) | 6.48 (3.15) | 6.57 (2.99) | 6.69 (3.02) | 6.89 (3.17) |
| LS Mean Change (SE) | −2.35 (0.18) | −3.66 (0.18) | −3.68 (0.18) | −3.85 (0.18) |
| LSMD vs. Placebo (95% CI) | — | −1.31 (−1.81, −0.82) | −1.33 (−1.82, −0.83) | −1.50 (−2.00, −1.01) |
| Nominal p-value | — | <.0001 | <.0001 | <.0001 |
| Adjusted p-value | — | <.0001 | <.0001 | <.0001 |

SD—Standard Deviation; LS—Least Squares; SE—Standard error of the least squares; CI—Confidence Interval; LSMD—least squares mean difference.

TABLE 9

Baseline Parameters on Efficacy Measures (mITT Population)

| Baseline Parameters, mean (SD) | Placebo (N = 214) | Atogepant 10 mg QD (N = 214) | Atogepant 30 mg QD (N = 223) | Atogepant 60 mg QD (N = 222) |
|---|---|---|---|---|
| Monthly Cumulative Headache Hours | 51.1 (34.5) | 47.4 (27.3) | 49.5 (26.7) | 50.4 (27.4) |
| Monthly Moderate/Severe Headache days | 6.5 (2.6) | 6.4 (2.6) | 6.9 (2.5) | 6.9 (2.6) |
| Weekly migraine days* | 1.9 (0.6) | 1.9 (0.6) | 2.0 (0.6) | 1.9 (0.6) |

*For weekly data, baseline was defined as monthly migraine days divided by 4, and change from baseline in weekly migraine days was calculated for consecutive 7-day periods beginning with day 1.

A secondary endpoint measured the change from baseline in MSQ v2.1 Role Function Restrictive Domain Score at Week 12. The Migraine-Specific Quality of Life Questionnaire Version 2.1 is one of the most frequently utilized disease-specific tools assessing the impact of migraine on HRQL. The MSQ measures the impact of migraine on the patient's HRQL over the past 4 weeks across three dimensions: Role Function-Restrictive (RR), Role Function-Preventive (RP), and Emotional Function (EF). The results from this secondary endpoint analysis are shown in Table 10.

TABLE 10

Change from Baseline in MSQ v2.1 Role Function Restrictive Domain* Score at Week 12 (mITT Population)

| | Placebo (N = 214) | Atogepant 10 mg QD (N = 214) | Atogepant 30 mg QD (N = 223) | Atogepant 60 mg QD (N = 222) |
|---|---|---|---|---|
| Baseline MSQ v2.1 role function restrictive domain score, mean (SD) | 46.8 (19.67) | 44.9 (21.37) | 44.0 (19.61) | 46.8 (20.36) |
| Week 12, mean (SD) | 66.3 (23.9) | 75.6 (23.5) | 75.4 (24.2) | 78.0 (25.0) |
| Change from baseline, mean (SD) | 19.5 (24.3) | 30.8 (27.6) | 31.1 (24.9) | 30.5 (25.1) |
| MMRM**, LS Mean Change (SE) | 20.45 (1.62) | 30.35 (1.64) | 30.53 (1.59) | 31.25 (1.59) |
| LSMD vs. Placebo (95% CI) | — | 9.90 (5.45, 14.36) | 10.08 (5.71, 14.46) | 10.80 (6.42, 15.18) |
| Nominal p-value | — | <.0001 | <.0001 | <.0001 |
| Adjusted p-value | — | <.0001 | <.0001 | <.0001 |

SD—Standard Deviation; LS—Least Squares; SE—Standard error of the least squares; CI—Confidence Interval; LSMD—least squares mean difference.
*Role Function-Restrictive domain assesses how migraines limit one's daily social and work-related activities. Participants respond to items using a 6-point scale ranging from "none of the time" to "all of the time." Raw domain scores are rescaled to a 0 to 100 scale, where higher scores indicate better quality of life. Items included leisure time activities; work or daily activities; getting done as much at work or home; concentrate on work or daily activities; left you too tired; dealt with family, friends, and others; felt energetic.
**The MMRM model includes baseline as a covariate, prior exposure to migraine prevention medications (y/n), treatment group, and visit (month) as fixed factors, and treatment group by visit and baseline-by-visit as interaction terms, with an unstructured covariance matrix. P values are from the test between the atogepant dose group and placebo.

As shown in Table 10, at week 12, statistically significant and clinically meaningful improvements for all dose groups vs placebo were observed in the RFR domain (10 mg, 9.9 [5.5-14.4]; 30 mg, 10.1 [5.7-14.5]; 60 mg, 10.8 [6.4-15.2]), in the RFP domain (10 mg, 5.8 [1.9-5.6]; 30 mg, 6.9 [3.1-10.7], 60 mg, 7.1 [3.3-10.9]), and in the EF domain (10 mg, 8.3 [3.4-13.1]; 30 mg, 9.7 (4.9-14.4]; 60 mg, 10.5 [5.8-15.3]). FIG. 11 illustrates the Migraine-Specific Quality of Life Questionnaire Role Function-Restrictive Domain Score at Weeks 4, 8, and 12. As shown in FIG. 11, for the RFR domain, significant differences vs. placebo were observed at the earliest time point assessed (week 4) and seen throughout the treatment period.

In people with 4-14 migraine days per month, oral atogepant produced significant and clinically meaningful between- and within-group reductions in emotional impact, improvements in functioning in daily social and work-related activities, the ability to undertake daily activities that had previously been prevented by migraine, and reduction in the emotional effect of migraine, as measured by the MSQ v 2.1. These results indicate that preventive treatment with atogepant is associated with statistically significant and clinically meaningful improvements in all domains of migraine-specific quality of life.

A secondary endpoint evaluated the change from baseline in mean monthly performance of daily activities domain score of the AIM-D across the 12-week treatment period.

Another secondary endpoint evaluated the change from baseline in mean monthly physical impairment domain score of the AIM-D across the 12-week treatment period. The Activity Impairment in Migraine-Diary (AIM-D) is an 11-item daily diary that is comprised of two domains that evaluate Performance of Daily Activities (PDA; 7 items) and Physical Impairment (PI; 4 items). See Cala et al., "The Activity Impairment in Migraine Diary (AIM-D): A novel migraine-specific patient-reported outcome measure to assess functioning based on activity impairment in episodic and chronic migraine patients", Cephalalgia 2018; 38:1-115, which is incorporated by reference herein in its entirety. In particular, the AIM-D assesses the impact of migraine on the performance of daily activities and physical impairment using a 6-point rating scale ranging from "Not difficult at all," "A little difficult," "Somewhat difficult," "Very Difficult," "Extremely Difficult", and "I could not do it at all." Items assessed for the AIM-D PDA domain included household chores, errands, leisure activities at home, social or leisure activities outside the home, strenuous physical activiacross the 12-week treatment period. The results with respect to daily activity are shown in Table 11. The results with respect to change from baseline in mean monthly physical impairment domain score are shown in Table 12.

TABLE 11

Change from Baseline in Mean Monthly Performance of Daily Activities Domain** Score of the AIM-D across the 12-week treatment period

| mITT Population | Placebo (n = 214) | Atogepant 10 mg QD (n = 214) | Atogepant 30 mg QD (n = 223) | Atogepant 60 mg QD (n = 222) |
|---|---|---|---|---|
| Change from baseline to week 12 | n = 178 | n = 182 | n = 181 | n = 178 |
| Baseline monthly performance of daily activities domain score, mean (SD) | 15.2 (8.25) | 15.5 (8.85) | 16.9 (8.02) | 15.9 (8.34) |
| Month 1-3$^a$, mean (SD) | 9.6 (7.2) | 8.6 (9.5) | 8.0 (8.1) | 6.6 (7.1) |
| Change from baseline, mean (SD) | −5.5 (7.6) | −7.0 (8.1) | −8.9 (7.5) | −9.2 (7.4) |
| MMRM$^b$, LS mean change (SE) | −6.1 (0.5) | −7.3 (0.5) | −8.6 (0.5) | −9.4 (0.5) |
| MMRM$^b$, LS Mean Change (SE) | −6.09 (0.50) | −7.28 (0.50) | −8.63 (0.50) | −9.41 (0.50) |
| LSMD vs. Placebo (95% CI) | — | −1.19 (−2.56, 0.17) | −2.54 (−3.91, −1.18) | −3.32 (−4.68, −1.96) |
| Nominal p-value | — | 0.0856 | 0.0003 | <.0001 |
| Adjusted p-value | — | 0.0856 | 0.0005 | <.0001 |

AIM-D, Activity Impairment in Migraine-Diary; SD—Standard Deviation; LS—Least Squares; SE—Standard error of the least squares; CI—Confidence Interval; LSMD—least squares mean difference; mITT, modified intent to treat; MMRM, mixed-effects model for repeated measures for change from baseline; QD, once daily.
$^a$Month 1-3 = average of monthly Performance of Daily Activity domain scores across the 12-week treatment period
$^b$The MMRM model includes baseline as a covariate, prior exposure to migraine prevention medications (y/n), treatment group, and visit (month) as fixed factors, and treatment group by visit and baseline-by-visit as interaction terms, with an unstructured covariance matrix. P values are from the test between the atogepant dose group and placebo.
**Items included household chores, errands, leisure activities at home, social or leisure activities outside the home, strenuous physical activities, concentration, and thinking clearly.

TABLE 12

Change from Baseline in Mean Monthly Physical Impairment Domain*** Score of the AIM-D Across the 12-Week Treatment Period (mITT population)

| | Placebo (N = 214) | Atogepant 10 mg QD (N = 214) | Atogepant 30 mg QD (N = 223) | Atogepant 60 mg QD (N = 222) |
|---|---|---|---|---|
| Baseline monthly physical impairment domain score, mean (SD) | 11.2 (8.11) | 11.7 (8.46) | 13.0 (8.00) | 11.6 (7.85) |
| LS Mean Change (SE) | −4.03 (0.44) | −5.11 (0.44) | −6.02 (0.44) | −6.49 (0.44) |
| LMSD vs. Placebo (95% CI) | — | −1.08 (−2.27, 0.11) | −1.99 (−3.18, −0.80) | −2.46 (−3.65, −1.28) |
| Nominal p-value | — | 0.0743 | 0.0011 | <.0001 |
| Adjusted p-value | — | 0.0856 | 0.0021 | 0.0002 |

SD—Standard Deviation; LS—Least Squares; SE—Standard error of the least squares; CI—Confidence Interval; LSMD—least squares mean difference.
***Items included walking, moving body, bending forward, and moving head.

ties, concentration, and thinking clearly. Items assessed for the AIM-D PI Domain included walking, moving body, bending forward, and moving head. Raw domain scores are recalled to a 0 to 100 scale, where higher scores indicate greater impact of migraine, and reductions from baseline in scores indicate improvement. The AIM-D was collected daily via an electronic diary with the same set of questions administered in headache (HA) and non-headache (NHA) versions. Monthly domain scores are calculated by summing the non-missing daily domain scores (HA and NHA days combined) and dividing the number of non-missing daily scores. The secondary endpoints for AIM-D PDA and PI domain scores were evaluated as change from baseline in mean monthly PDA or PI domain scores of the AIM-D As shown in Tables 11 and 12, compared with placebo, all atogepant groups demonstrated improvement of function in PDA and PI domain scores across the 12-week treatment period. For both AIM-D domains, differences were statistically significant for participants in the atogepant 60 mg and 30 mg groups (least squares mean difference [LSMD] vs placebo: PDA, −3.32 for 60 mg, −2.54 for 30 mg; PI, −2.46 for 60 mg, −1.99 for 30 mg). The improvement in PDA and PI domain scores for the atogepant 10 mg group did not reach statistical significance vs. placebo (LSMD: −1.19 and −1.08, respectively).

As shown above, with respect to the secondary endpoints, treatment with 30 mg and 60 mg atogepant doses resulted in statistically significant improvements in all secondary endpoints, and treatment with 10 mg atogepant resulted in statistically significant improvements in four out of the six secondary endpoints. Atogepant demonstrated significant improvements in patients' functioning in daily activities, and reductions in physical impairment and the impact of headaches, confirming its role as a promising treatment among people with migraine.

The Headache Impact Test (HIT-6, completed monthly) represented an additional exploratory measure. The HIT-6 test is a well-known tool for assessing migraine intensity that uses six questions to capture the impact of headache and its treatment on an individual's functional health and well-being. HIT-6 was completed monthly and was evaluated as the change from baseline in HIT-6 total score at weeks 4, 8, and 12. HIT-6 results are shown in Table 13.

TABLE 13

HIT-6: Change from Baseline to Week 12

| mITT Population | Placebo (n = 214) | Atogepant 10 mg QD (n = 214) | Atogepant 30 mg QD (n = 223) | Atogepant 60 mg QD (n = 222) |
|---|---|---|---|---|
| Change from baseline to week 12 | n = 178 | n = 182 | n = 181 | n = 178 |
| Baseline, mean (SD) | 64.5 (4.5) | 64.1 (5.4) | 64.3 (4.9) | 63.6 (5.6) |
| Week 12, mean (SD) | 59.2 (6.5) | 55.8 (8.3) | 56.1 (8.6) | 54.5 (9.0) |
| Change from baseline, mean (SD) | −5.3 (6.8) | −8.3 (7.8) | −8.1 (7.9) | −9.9 (8.7) |
| MMRM[b], LS mean change (SE) | −5.2 (0.5) | −8.4 (0.5) | −8.1 (0.5) | −9.2 (0.5) |
| LSMD vs placebo (95% CI) | | −3.2 (−4.7, −1.7) | −2.9 (−4.3, −1.4) | −4.0 (−5.4, −2.5) |
| P value | | <0.0001 | 0.0001 | <0.0001 |
| Responders[c], n/N (%) | | | | |
| Week 4 | 127/206 (38.3) | 101/208 (48.6) | 102/219 (46.8) | 122/217 (56.2) |
| Odds ratio vs. Placebo (95% CI) | | 1.53 (1.03, 2.27) | 1.43 (0.97, 2.12) | 2.18 (1.47, 3.25) |
| P value | | 0.0386 | 0.738 | 0.0001 |
| Week 8 | 96/203 (47.3) | 113/187 (60.4) | 130/209 (62.2) | 134/207 (64.7) |
| Odds ratio vs. Placebo (95% CI) | | 1.79 (1.19, 2.68) | 1.95 (1.31, 2.90) | 2.25 (1.50, 3.37) |
| P value | | 0.0053 | 0.0011 | <0.0001 |
| Week 12 | 103/198 (52.0) | 120/186 (64.5) | 128/204 (62.7) | 131/201 (65.2) |
| Odds ratio vs. Placebo (95% CI) | | 1.74 (1.15, 2.62) | 1.54 (1.03, 2.30) | 1.77 (1.18, 2.66) |
| P value | | 0.0086 | 0.0334 | 0.0055 |

HIT-6, 6-item headache impact test; LSMD, least squares mean difference; mITT, modified intent to treat; MMRM, mixed-effects model for repeated measures change from baseline; QD, once daily; SD, standard deviation; SE, standard error of the least squares.
[b]The MMRM model includes baseline as a covariate, prior exposure to migraine prevention medications (y/n), treatment group, and visit (month) as fixed factors, and treatment group by visit and baseline-by-visit as interaction terms, with an unstructured covariance matrix. P values are from the test between the atogepant dose group and placebo.
[c]Responders defined as patients experiencing a ≥5 point reduction in the HIT-6 score.

All atogepant groups demonstrated significant improvement in HIT-6 scores vs. placebo at weeks 4, 8, and 12. Significantly greater proportions of atogepant vs. placebo-treated participants were HIT-6 responders (≥5 point decrease) with all atogepant doses (except 30 mg at week 4).

The AIM-D and HIT-6 results demonstrate that atogepant significantly improved patient functioning in daily activities, and reduced physical impairment and impact of headaches.

Additional prespecified responder analyses included the Patient Global Impression of Change (PGI-C), defined as "much better" or "very much better" at week 12, and satisfaction with study medication, defined as "satisfied" or "extremely satisfied" at weeks 4, 8, and 12. The results are shown in Table 14.

TABLE 14

PGI-C and Treatment Satisfaction After 12 Weeks of Treatment (mITT Population)

| Responder Criteria, Week 12 | Placebo (n = 214) | Atogepant 10 mg (n = 214) | Atogepant 30 mg (n = 223) | Atogepant 60 mg (n = 222) |
|---|---|---|---|---|
| PGI-C,[a] n/N | 95/206 | 145/201 | 153/209 | 162/213 |
| Percentage | 46.1% | 72.1% | 73.2% | 76.1% |
| OR (95% CI) | — | 3.05 (2.01, 4.61) | 3.33 (2.20, 5.05) | 3.83 (2.52, 5.84) |
| P value | | <0.0001 | <0.0001 | <0.0001 |

TABLE 14-continued

PGI-C and Treatment Satisfaction After
12 Weeks of Treatment (mITT Population)

| Responder Criteria, Week 12 | Placebo (n = 214) | Atogepant 10 mg (n = 214) | Atogepant 30 mg (n = 223) | Atogepant 60 mg (n = 222) |
|---|---|---|---|---|
| Satisfaction with Study Medication[b] | 109/199 | 146/188 | 162/203 | 166/201 |
| Percentage | 54.8% | 77.7% | 80.3% | 82.6% |
| OR (95% CI) | — | 2.77 (1.81, 4.24) | 3.44 (2.23, 5.30) | 3.58 (2.31, 5.54) |
| P value | | <0.0001 | <0.0001 | <0.0001 |

[a]Response defined as "much better" or "very much better"
[b]Response defined as "satisfied" or "extremely satisfied."
OR, odds ratio; PGI-C, Patient Global Impression of Change.

Significantly higher proportions of patients receiving atogepant were responders at week 12 for PGI-C (72%-76%) and were satisfied with treatment (78%-83%) vs placebo (46% and 55%, P≤0.0001), as shown in Table 14. The odds of achieving PGI-C response in each atogepant group was ≥3 times that of placebo. A greater proportion of participants in each of the three atogepant arms met treatment satisfaction responder criteria at weeks 4, 8, and 12, compared with placebo, as shown in Table 14. The odds for being treatment satisfaction responders at week 12 for atogepant were approximately 2-4 times greater than placebo.

Participants treated with atogepant were more satisfied with treatment and reported greater improvement in their migraine attacks compared with placebo. Even if a participant did not achieve the thresholds for being considered a treatment responder, a high proportion of participants (70-80%) reported feeling "much better" or "very much better", demonstrating that some individuals experience a treatment benefit without exceeding specified responder definitions.

The study further showed that atogepant was safe and well-tolerated. Adverse events were reported by participants throughout the trial, and at a 4-week follow-up visit. Adverse event information was collected and documented during each clinic visit. Participants could also report adverse events via telephone call between visits. Causality of each adverse event was determined by the investigator who was blinded to the treatment. In addition, clinical laboratory tests, vital signs, electrocardiograms (ECG), and Columbia-Suicide Severity Rating Scale were evaluated. Based on the potential hepatotoxicity of prior gepants, treatment-emergent elevations in ALT or AST ≥3 times the upper limit of normal, as well as potential Hy's law cases, were evaluated as prespecified adverse events of special interest and were reviewed by an independent panel of liver experts blinded to treatment (see, e.g., Negro A et al., CGRP Receptor Antagonists: an expanding drug class for acute migraine? Expert Opin Investig Drugs 2012; 21:807-18; Messina R et al., CGRP—a target for acute therapy in migraine: Clinical Data. Cephalalgia 2019; 39:420-7).

Rates of adverse events (AEs) were similar across all treatment groups. Treatment-emergent adverse events were reported in 53.9% of participants (486 of 902 participants); the frequency of events was similar between placebo and atogepant treatment groups and no dose relationship was observed. Serious adverse events occurred in 0.9% of patients treated in the atogepant 10 mg arm compared to 0.9% of patients in the placebo arm (2 participants in both the placebo and atogepant 10 mg groups). In particular, serious adverse events were reported in 2 participants treated with placebo (gastric ulcer hemorrhage; post-surgical laryngospasm with hypoxic brain injury) and 2 participants treated with atogepant 10 mg (asthma attack; optic neuritis). The asthma attack was considered unrelated to trial treatment and clinical evidence did not support the diagnosis of optic neuritis.

No patients in the atogepant 30 mg or 60 mg treatment arms experienced a serious adverse event. The most common adverse events reported with a frequency of ≥5% in at least one atogepant treatment arm, and greater than placebo, were constipation (6.9-7.7% across all doses vs. 0.5% for placebo), nausea (4.4-6.1% across all doses vs. 1.8% for placebo), and upper respiratory tract infection (3.9-5.7% across all doses vs. 4.5% for placebo). The majority of cases of constipation, nausea and upper respiratory tract infection were mild or moderate in severity and did not lead to discontinuation. Cases of constipation were primarily mild (71.4%) or moderate (26.5%) in severity. One case of constipation was considered severe in the atogepant 10 mg group. This was reported as a worsening of pre-existing constipation and the participant was treated with over-the-counter medication, completed the trial, and entered an open-label extension study. All reported cases of nausea were mild (77.1%) or moderate (22.9%) in severity.

Rates of discontinuation due to AEs were low across all treatment groups and not dose-dependent. Rates of discontinuation for the highest doses were the same or lower than placebo. The rates of adverse events are summarized in Table 15:

TABLE 15

Adverse Events

| | Placebo (N = 222) n(%) | Atogepant 10 mg QD (N = 221) n(%) | Atogepant 30 mg QD (N = 228) n(%) | Atogepant 60 mg QD (N = 231) n(%) |
|---|---|---|---|---|
| Adverse Event | 126 (56.8) | 117 (52.9) | 119 (52.2) | 124 (53.7) |
| Serious AE | 2 (0.9) | 2 (0.9) | 0 | 0 |

TABLE 15-continued

| Adverse Events | Placebo (N = 222) n(%) | Atogepant 10 mg QD (N = 221) n(%) | Atogepant 30 mg QD (N = 228) n(%) | Atogepant 60 mg QD (N = 231) n(%) |
|---|---|---|---|---|
| AE leading to Discontinuation | 6 (2.7) | 9 (4.1) | 4 (1.8) | 6 (2.6) |
| Treatment Emergent Adverse Event | 126 (56.8) | 117 (52.9) | 119 (52.2) | 124 (53.7) |
| TEAEs reported in >=2% of participants in any treatment group | | | | |
| Constipation | 1 (0.5) | 17 (7.7) | 16 (7.0) | 16 (6.9) |
| Upper Respiratory Tract Infection | 10 (4.5) | 9 (4.1) | 13 (5.7) | 9 (3.9) |
| Nausea | 4 (1.8) | 11 (5.0) | 10 (4.4) | 14 (6.1) |
| Urinary Tract Infection | 8 (3.6) | 3 (1.4) | 9 (3.9) | 9 (3.9) |
| Nasopharyngitis | 8 (3.6) | 4 (1.8) | 8 (3.5) | 8 (3.5) |
| Fatigue | 4 (1.8) | 3 (1.4) | 7 (3.1) | 9 (3.9) |
| Somnolence | 2 (0.9) | 7 (3.2) | 4 (1.8) | 4 (1.7) |
| Blood creatine phosphokinase increased | 2 (0.9) | 5 (2.3) | 2 (0.9) | 7 (3.0) |
| Sinusitis | 3 (1.4) | 4 (1.8) | 3 (1.3) | 5 (2.2) |
| Gastroenteritis | 4 (1.8) | 2 (0.9) | 5 (2.2) | 3 (1.3) |
| Alanine aminotransferase increased | 6 (2.7) | 3 (1.4) | 2 (0.9) | 2 (0.9) |
| Influenza | 2 (0.9) | 3 (1.4) | 2 (0.9) | 5 (2.2) |
| Sinus Congestion | 5 (2.3) | 1 (0.5) | 2 (0.9) | 4 (1.7) |
| Aspartate aminotransferase increased | 6 (2.7) | 2 (0.9) | 2 (0.9) | 1 (0.4) |
| Anxiety | 2 (0.9) | 2 (0.9) | 1 (0.4) | 5 (2.2) |
| Treatment-related TEAE | 20 (9.0) | 51 (23.1) | 34 (14.9) | 45 (19.5) |
| Treatment-emergent serious adverse event | 2 (0.9) | 2 (0.9) | 0 (0.0) | 0 (0.0) |
| Treatment related TESAE | 0 (0.0) | 1 (0.5) | 0 (0.0) | 0 (0.0) |
| Deaths | 0 (0.0) | 0 (0.0) | 0 (0.0) | 0 (0.0) |
| TEAE leading to treatment discontinuation | 6 (2.7) | 9 (4.1) | 4 (1.8) | 6 (2.6) |

Safety population included all randomized participants who took at least 1 dose of trial treatment. Participants are only counted once within each category. Percentages are calculated at 100×(n/N), where n is the number of participants within a specific category and N is the number of participants in the safety population for the treatment group. Adverse events are listed in decreasing order based on frequency reported in the overall population.

There were no hepatic safety issues identified in this trial. ALT and/or AST increases were low across all atogepant doses and occurred at a lower rate than placebo. Cases of ALT or AST elevations that were ≥3× upper limit of normal (ULN) occurred at a lower rate compared to placebo (where 4 cases were reported), and did not increase with an increase in dose. No cases of liver disease were reported, and no case met the criteria for potential Hy's Law following daily dosing for 12 weeks. Tables 16 and 17 summarize postbaseline hepatic laboratory parameter values.

TABLE 16

Postbaseline Hepatic Laboratory Parameter Values of Clinical Interest - Safety Population

| Parameter Criterion | Placebo (N = 222) n/N1 | Atogepant 10 mg QD (N = 221) n/N1 | Atogepant 30 mg QD (N = 228) n/N1 | Atogepant 60 mg QD (N = 231) n/N1 |
|---|---|---|---|---|
| ALT or AST (U/L) | | | | |
| >=1 * ULN | 35/220 (15.9) | 19/220 (8.6) | 18/225 (8.0) | 28/228 (12.3) |
| >=1.5 * ULN | 14/220 (6.4) | 3/220 (1.4) | 7/225 (3.1) | 7/228 (3.1) |
| >=2 * ULN | 6/220 (2.7) | 2/220 (0.9) | 2/225 (0.9) | 4/228 (1.8) |
| >=3 * ULN | 4/220 (1.8) | 2/220 (0.9) | 2/225 (0.9) | 1/228 (0.4) |
| >=5 * ULN | 1/220 (0.5) | 1/220 (0.5) | 1/225 (0.4) | 1/228 (0.4) |
| >=10 * ULN | 0 | 1/220 (0.5) | 0 | 0 |
| >=20 * ULN | 0 | 0 | 0 | 0 |

TABLE 16-continued

Postbaseline Hepatic Laboratory Parameter Values
of Clinical Interest - Safety Population

| Parameter Criterion | Placebo (N = 222) n/N1 | Atogepant 10 mg QD (N = 221) n/N1 | Atogepant 30 mg QD (N = 228) n/N1 | Atogepant 60 mg QD (N = 231) n/N1 |
|---|---|---|---|---|
| Potential Hy's Law | | | | |
| ALT or AST >=3 * ULN AND Bilirubin Total >=2 * ULN AND ALP <2 * ULN | 0 | 0 | 0 | 0 |

N1 = Number of participants with at least one non-missing postbaseline value.
n = Number of participants within a specific category.
ULN = Upper limit of normal value

TABLE 17

Hepatic Safety Summary

| | Placebo (N = 222) | Atogepant 10 mg QD (N = 221) | Atogepant 30 mg QD (N = 228) | Atogepant 60 mg QD (N = 231) |
|---|---|---|---|---|
| ALT or AST (U/L), n/N1 (%) ≥3x upper limit of normal (ULN) | 4/220 (1.8) | 2/220 (0.9) | 2/225 (0.9) | 1/228 (0.4) |
| Potential Hy's Law ALT or AST ≥3x ULN AND Bilirubin Total ≥2x ULN AND ALP <2x ULN | 0 | 0 | 0 | 0 |

N1 = number of participants with at least one non-missing postbaseline value
n = number of participants within a specific category.

In summary, as shown above, atogepant 10 mg, 30 mg, and 60 mg groups demonstrated statistically significant and clinically meaningful improvements over the placebo group for the primary efficacy endpoint (reduction in mean monthly migraine days). There was a clinically relevant dose response relationship. Significant improvements were also observed for all secondary endpoints, with atogepant 30 mg and 60 mg meeting all six secondary endpoints, and atogepant 10 mg meeting four secondary endpoints. Atogepant 10 mg, 30 mg, and 60 mg groups demonstrated statistically significant and clinically meaningful improvements over the placebo group in the proportion of patients with 50% reduction in mean monthly migraine days (56-61% reduction in monthly migraine days vs. 29% for placebo).

Atogepant was safe and well-tolerated. The most common TEAEs were constipation (~7%) and nausea (~5%). No hepatic safety issues were identified.

Example 2

Study B: A phase 3, multicenter, randomized, open label study was conducted to evaluate the long-term safety and tolerability of oral atogepant for the prevention of migraine in participants with episodic migraine (Study B). The study objective was to evaluate the safety and tolerability of daily treatment with atogepant 60 mg QD when administered over 52 weeks for the prevention of migraine in participants with episodic migraine.

Figure 12:
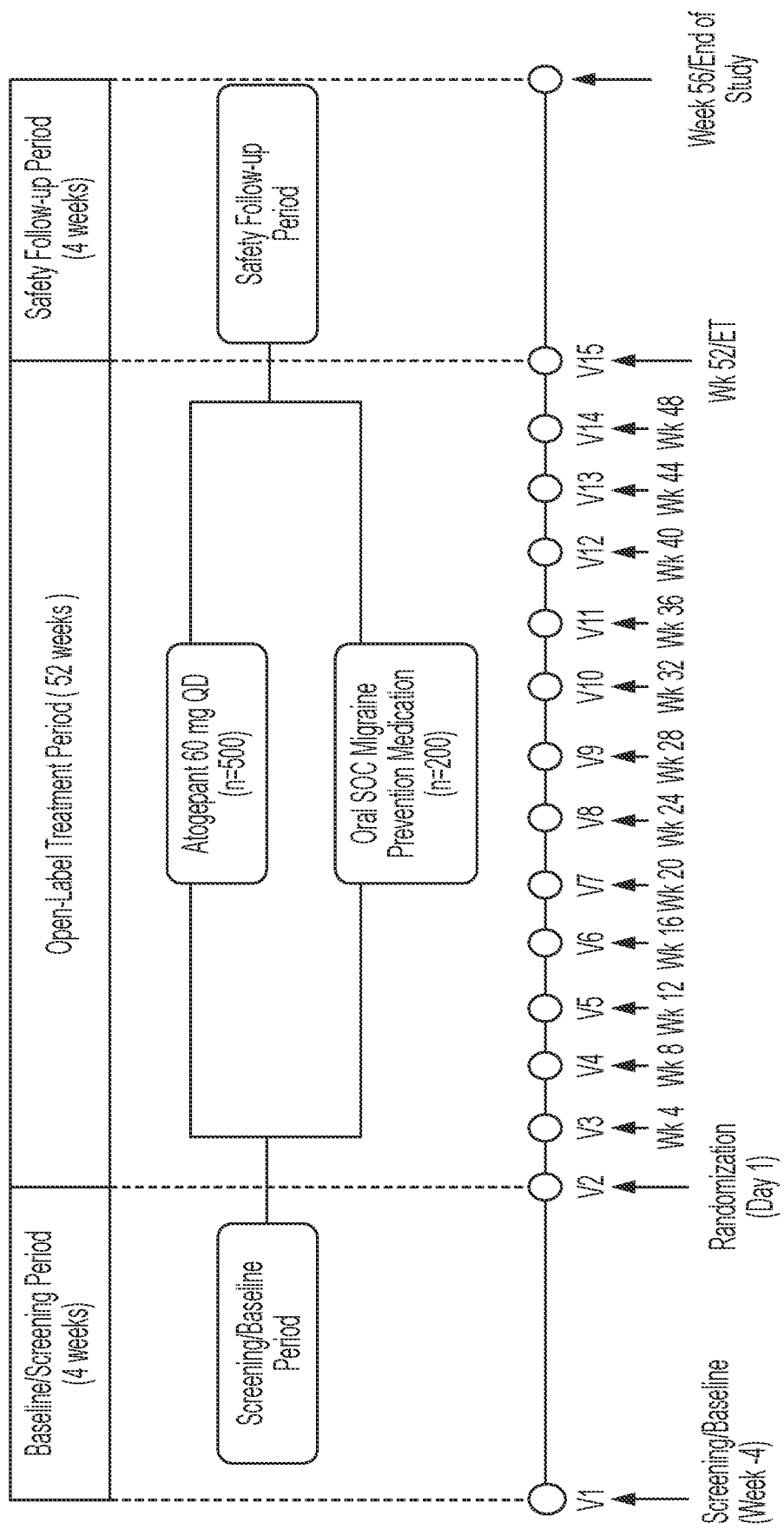
FIG. 12 provides a schematic for the design of the study evaluating the safety and tolerability of long-term atogepant treatment (Study B).

FIG. 12 provides a schematic for the long-term safety study design. The study comprised a 4-week baseline/screening period, followed by a 52-week open-label treatment period, and a 4-week safety follow-up period.

A total of 744 participants from 106 sites were randomized in a ratio of 5:2 to the following treatment groups: atogepant 60 mg QD or oral standard of care (SOC) migraine prevention medication. The latter arm was included to contextualize safety data from the atogepant-treated participants, and efficacy measures were collected from the atogepant arm only. Efficacy measures were evaluated using the modified intent-to-treat (mITT) population and a mixed-effects model for repeated measures and included changes from baseline in monthly migraine days (MDDs), moderate/severe headache days, and acute medication use days, as well as the proportion of responders based on reductions in MMDs.

A total of 739 patients (n=546 atogepant) were included in the safety population. Participants included: (1) eligible participants who completed study NCT02848326 (visit 8) without significant protocol deviations (e.g., non-compliance with protocol-required procedures) and who did not experience an AE that, in the investigator's opinion, may indicate an unacceptable safety risk; and (2) de novo participants—adults (18-80 years) with a history (≥1 year) of migraine and 4-14 migraine days per month.

For participants in the SOC group, participants who did not tolerate the initially prescribed migraine preventive medication, or for whom the medication was not sufficiently effective (per investigator judgment), the investigator was allowed to prescribe an alternative medication or not prescribe any migraine preventive mediation. Regardless of which of these options was chosen, the participant was allowed to continue in the study. In addition, the investigator had the option to select alternative preventive medication, or discontinue migraine prevention medication, for a participant in the SOC migraine preventive medication arm as often as needed throughout the study.

Table 18 provides a summary of the subject population.

TABLE 18

Subject Population

| Population | Standard of Care | Atogepant 60 mg QD | Overall |
|---|---|---|---|
| Screened, N | — | — | 1727 |
| Intent-to-Treat, N | 198 | 546 | 744 |
| De Novo, N | 170 | 467 | 637 |
| CGP-MD-01 Completers, N | 28 | 79 | 107 |
| Safety, N | 196 | 543 | 739 |
| Modified Intent-to-Treat, N | — | 521 | 521 |

All Screened Participants include those screened participants that signed informed consent forms. The Intent-to-Treat Population (ITT) includes all of the randomized participants. The safety population includes all participants who received at least one dose of study intervention (atogepant or SOC medication). The modified intent-to-treat population (mITT) includes all randomized participants who received at least one dose of atogepant, had an evaluable baseline period of eDiary data, and had at least one evaluable post-baseline 4-week period of eDiary data.

Table 19 provides a summary of patient disposition during the open-label treatment period for all randomized participants.

TABLE 19

Participant Disposition During Open-Label Treatment Period - All Randomized Participants

| | Standard of Care (N = 198) n (%) | Atogepant 60 mg QD (N = 546) n (%) | Overall (N = 744) n (%) |
|---|---|---|---|
| Disposition | | | |
| Number of Participants Entered | 198 (100.0) | 546 (100.0) | 744 (100.0) |
| Number of Participants Completed | 136 (68.7) | 373 (68.3) | 509 (68.4) |
| Number of Participants Discontinued | 62 (31.3) | 173 (31.7) | 235 (31.5) |
| Reason for Discontinuation | | | |
| Adverse events | 5 (2.5) | 31 (5.7) | 36 (4.8) |
| Lack of Efficacy | 2 (1.0) | 5 (0.9) | 7 (0.9) |
| Withdrawal by Subject | 29 (14.6) | 75 (13.7) | 104 (14.0) |
| Lost to Follow-Up | 16 (8.1) | 23 (4.2) | 39 (5.2) |
| Pregnancy | 2 (1.0) | 4 (0.7) | 6 (0.8) |
| Protocol Deviation | 7 (3.5) | 31 (5.7) | 38 (5.1) |
| Non-compliance with study drug | 1 (0.5) | 3 (0.5) | 4 (0.5) |
| Other | 0 (0.0) | 1 (0.2) | 1 (0.1) |

Table 20 provides a summary of the baseline demographics of the safety population. Table 21 provides the migraine history of the safety population.

TABLE 20

Baseline Demographics (Safety Population)

| Baseline Demographics | | Standard of Care (N = 196) | Atogepant 60 mg QD (N = 543) | Total (N = 739) |
|---|---|---|---|---|
| Age | Mean (SD) years | 41.1 (12.09) | 42.5 (12.03) | 42.2 (12.05) |
| Sex | Female | 87.8% | 88.2% | 88.1% |
| Race | White | 74.0% | 76.6% | 75.9% |
| Ethnicity | Hispanic | 14.8% | 15.3% | 15.2% |
| BMI | Mean (SD) (kg/m$^2$) | 30.60 (8.028) | 30.54 (7.440) | 30.55 (7.595) |
| Prior Exposure to a Migraine Prevention Medication with Proven Efficacy | Yes | 23.5% | 27.6% | 26.5% |

TABLE 21

Migraine History (Safety Population)

| Parameter | | Standard of Care (N = 196) | Atogepant 60 mg QD (N = 543) | Total (N = 739) |
|---|---|---|---|---|
| Migraine Diagnosis | With aura/ without aura/both | 24.0%/42.3%/33.7% | 21.4%/41.1%/37.6% | 21.1%/41.4%/36.5% |
| Migraine Disorder Duration in Years | Mean (SD) | 19.6 (12.41) | 20.9 (12.38) | 20.6 (12.39) |
| Migraine Prevention Medication in the Past | Yes | 28.1% | 33.0% | 31.7% |

TABLE 21-continued

Migraine History (Safety Population)

| Parameter | | Standard of Care (N = 196) | Atogepant 60 mg QD (N = 543) | Total (N = 739) |
|---|---|---|---|---|
| Average number of migraine days per month in the last 3 months | Mean (SD) | 7.2 (2.56) | 7.3 (2.59) | 7.3 (2.58) |
| Average number of headache days per month in the last 3 months | Mean (SD) | 9.4 (2.72) | 9.2 (2.74) | 9.3 (2.74) |
| Acute Medication Treatment | Yes | 97.4% | 99.3% | 98.8% |
| Advice on Lifestyle Alterations | Yes | 49.5% | 51.2% | 50.7% |

Treatment duration in summarized in Table 22.

TABLE 22

Treatment Duration (Study Population)

| | Standard of care (N = 196) | Atogepant 60 mg QD (N = 543) |
|---|---|---|
| | Algorithm | |
| Treatment Duration (days) | Treatment Duration = Last treatment date − first treatment date + 1 | Treatment duration = last study treatment date − first study treatment date + 1 |
| Mean (SD) | 278.9 (143.08) | 291.6 (123.40) |
| ≥30 days | 180 (91.8) | 508 (93.6) |
| ≥90 days | 160 (81.6) | 459 (84.5) |
| ≥180 days | 140 (71.4) | 428 (78.8) |
| ≥270 days | 123 (62.8) | 397 (73.1) |
| ≥360 days | 115 (58.7) | 362 (66.7) |

Adverse events were reported by 67.0% of participants treated with atogepant; 18.0% of participants reported AEs that were considered related to atogepant by the investigator. Most commonly reported AEs (≥5% of participants) were upper respiratory tract infection (10.3%), constipation (7.2%), nausea (6.3%), and urinary tract infection (5.2%) following treatment with atogepant. Serious AEs were reported by 4.4% of participants treated with atogepant, which included a broad variety of common medical conditions; no event was seen in more than one participant and no event was considered related to atogepant. Two deaths were reported in participants treated with atogepant (victim of homicide and a group A beta-hemolytic streptococcal sepsis [toxic shock syndrome]); both were considered not related to atogepant. Discontinuation due to AEs was 5.7% following treatment with atogepant. Table 23 summarizes the adverse events in the safety population.

TABLE 23

Summary of Adverse Events (Safety Population)

| | Standard of care (N = 196) n (%) | Atogepant 60 mg QD (N = 543) n (%) |
|---|---|---|
| Treatment-emergent adverse event (TEAE) | 154 (78.6) | 364 (67.0) |
| Treatment-related TEAE | 71 (36.2) | 98 (18.0) |
| Death | 0 (0.0) | 2 (0.4) |
| Treatment-emergent serious adverse events (TESAE) | 7 (3.6) | 24 (4.4) |
| TEAE leading to study discontinuation | 5 (2.6) | 31 (5.7) |

Cases of alanine aminotransferase/aspartate aminotransferase (ALT/AST) levels ≥3 times the upper limit of normal were reported for 2.4% of participants (n=13/531) treated with atogepant and 3.2% for standard-of-care (n=6/190). No cases of potential Hy's Law were reported. Table 24 provides postbaseline hepatic laboratory parameter values of clinical interest for the safety population.

TABLE 24

Postbaseline Hepatic Laboratory Parameter Values of Clinical Interest (Safety Population)

| Parameter (unit) Criteria | Standard of care (N = 196) n/N1 | Atogepant 60 mg QD (N = 543) n/N1 |
|---|---|---|
| ALT or AST (U/L) | | |
| ≥1 × ULN | 55/190 (28.9) | 112/531 (21.1) |
| ≥1.5 × ULN | 16/190 (8.4) | 46/531 (8.7) |
| ≥2 × ULN | 11/190 (5.8) | 26/531 (4.9) |
| ≥3 × ULN | 6/190 (3.2) | 13/531 (2.4) |
| ≥5 × ULN | 1/190 (0.5) | 7/531 (1.3) |
| ≥10 × ULN | 0/190 (0.0) | 3/531 (0.6) |
| ≥20 × ULN | 0/190 (0.0) | 0/531 (0.0) |
| Potential Hy's Law (ALT or AST ≥3 × ULN and Bilirubin Total ≥2 × ULN and ALP <2 × ULN | 0/190 (0.0) | 0/531 (0.0) |

N1 = number of participants with at least one non-missing baseline value.
n = number of participants within a specific category Efficacy endpoints for this study included change from baseline in monthly migraine days at each monthly period; change from baseline in monthly headache days at each monthly period; change from baseline in monthly acute medication use days at each monthly period; and ≥50% improvement (reduction) in monthly migraine days at each monthly period.

Figure 13:
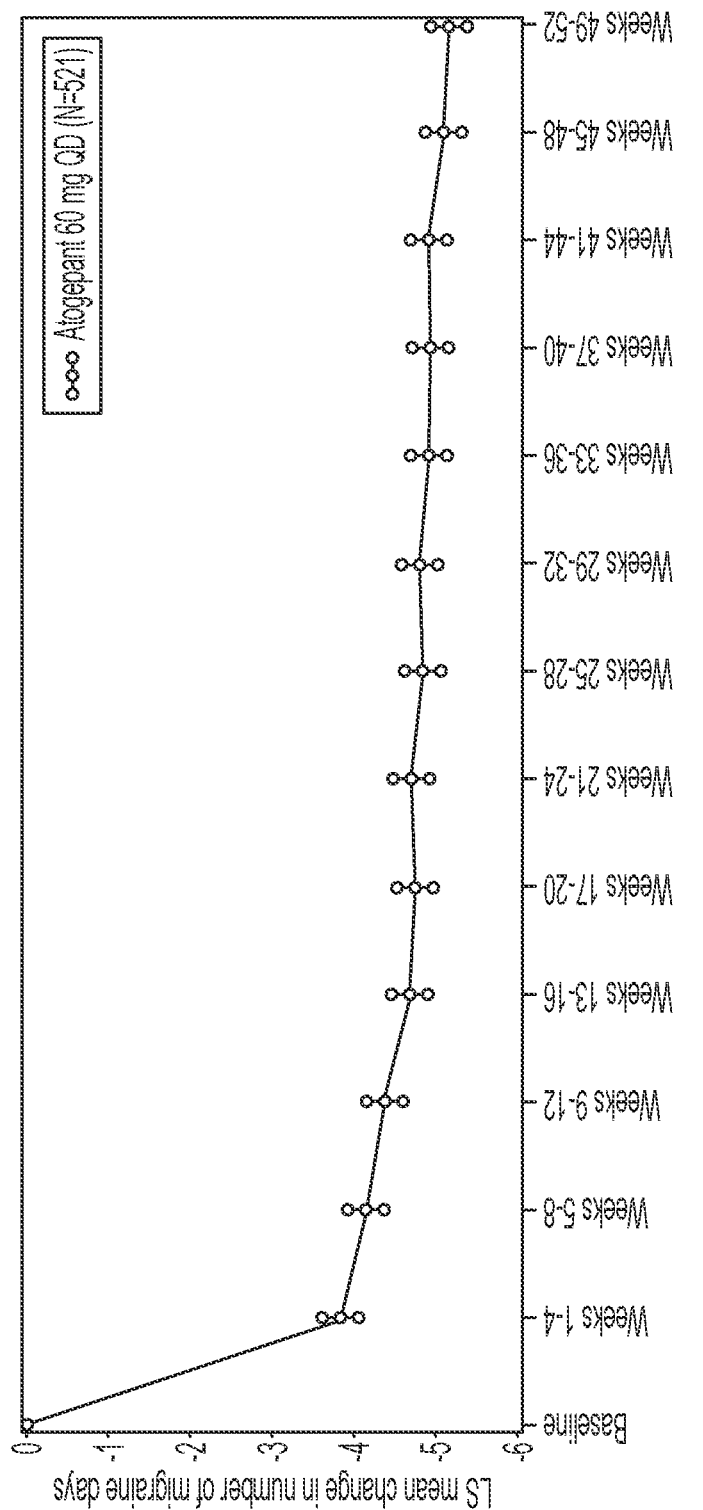
FIG. 13 shows the LS mean change from baseline in number of migraine days over time (mITT population) in the 52-week long term safety study of atogepant. Administration of 60 mg atogepant led to a rapid reduction in monthly migraine days in month 1, with additional gradual improvement over time through week 52.

LS mean change from baseline in monthly migraine days over time (mITT population) is shown in FIG. 13. As shown in FIG. 13, atogepant 60 mg led to a reduction from baseline in monthly migraine days of approximately 4 days in month 1, followed by additional improvement over time for the remaining months. That is, a rapid reduction in monthly migraine days was observed in month 1, with additional gradual improvement over time through week 52. The change from baseline in monthly migraine days over time (mITT population) is shown in Table 25.

TABLE 25

Change from Baseline in Monthly Migraine Days Over Time (mITT Population)

| | | Atogepant 60 mg QD (N = 521) | |
|---|---|---|---|
| Derived Visit | N | Observed Mean (SD) | Change from Baseline LS means (95% CI) - MMRM |
| Baseline | 521 | 7.31 (2.61) | — |
| Weeks 1-4 | 513 | 3.47 (3.35) | −3.84 (−4.10, −3.57) |
| Weeks 5-8 | 490 | 3.13 (3.47) | −4.15 (−4.44, −3.87) |
| Weeks 9-12 | 466 | 2.85 (3.25) | −4.38 (−4.65, −4.11) |
| Weeks 13-16 | 440 | 2.52 (3.14) | −4.69 (−4.95, −4.43) |
| Weeks 17-20 | 419 | 2.33 (3.01) | −4.76 (−5.02, −4.50) |
| Weeks 21-24 | 417 | 2.37 (3.20) | −4.72 (−5.00, −4.43) |
| Weeks 25-28 | 398 | 2.20 (3.21) | −4.85 (−5.14, −4.56) |
| Weeks 29-32 | 390 | 2.12 (3.06) | −4.82 (−5.11, −4.53) |
| Weeks 33-36 | 379 | 2.06 (3.03) | −4.95 (−5.23, −4.67) |
| Weeks 37-40 | 375 | 2.08 (3.08) | −4.97 (−5.26, −4.68) |
| Weeks 41-44 | 363 | 2.09 (3.21) | −4.95 (−5.25, −4.65) |
| Weeks 45-48 | 352 | 1.91 (3.22) | −5.13 (−5.44, −4.83) |
| Weeks 49-52 | 335 | 1.84 (3.28) | −5.19 (−5.50, −4.87) |

MMRM = Mixed-effects model for repeated measures

Table 26 provides the change from baseline in monthly headache days over time (mITT population).

TABLE 26

Change from Baseline in Monthly Headache Days Over Time (mITT Population)

| | | Atogepant 60 mg QD (N = 521) | |
|---|---|---|---|
| Derived Visit | N | Observed Mean (SD) | Change from Baseline LS means (95% CI) - MMRM |
| Baseline | 521 | 8.42 (2.95) | — |
| Weeks 1-4 | 513 | 4.40 (3.75) | −4.00 (−4.30, −3.71) |
| Weeks 5-8 | 490 | 3.97 (3.75) | −4.40 (−4.71, −4.10) |
| Weeks 9-12 | 466 | 3.51 (3.52) | −4.80 (−5.09, −4.51) |
| Weeks 13-16 | 440 | 3.19 (3.40) | −5.12 (−5.40, −4.84) |
| Weeks 17-20 | 419 | 2.84 (3.32) | −5.35 (−5.64, −5.06) |
| Weeks 21-24 | 417 | 2.87 (3.47) | −5.30 (−5.61, −4.99) |
| Weeks 25-28 | 398 | 2/74 (3.59) | −5.42 (−5.74, −5.09) |
| Weeks 29-32 | 390 | 2.52 (3.41) | −5.41 (−5.72, −5.09) |
| Weeks 33-36 | 379 | 2.47 (3.31) | −5.62 (−5.92, −5.32) |
| Weeks 37-40 | 375 | 2.45 (3.28) | −5.69 (−6.00, −5.38) |
| Weeks 41-44 | 363 | 2.45 (3.45) | −5.66 (−5.99, −5.34) |
| Weeks 45-48 | 352 | 2.23 (3.43) | −5.90 (−6.22, −5.58) |
| Weeks 49-52 | 335 | 2.13 (3.54) | −5.99 (−6.33, −5.66) |

MMRM = Mixed-effects model for repeated measures

Figure 14:
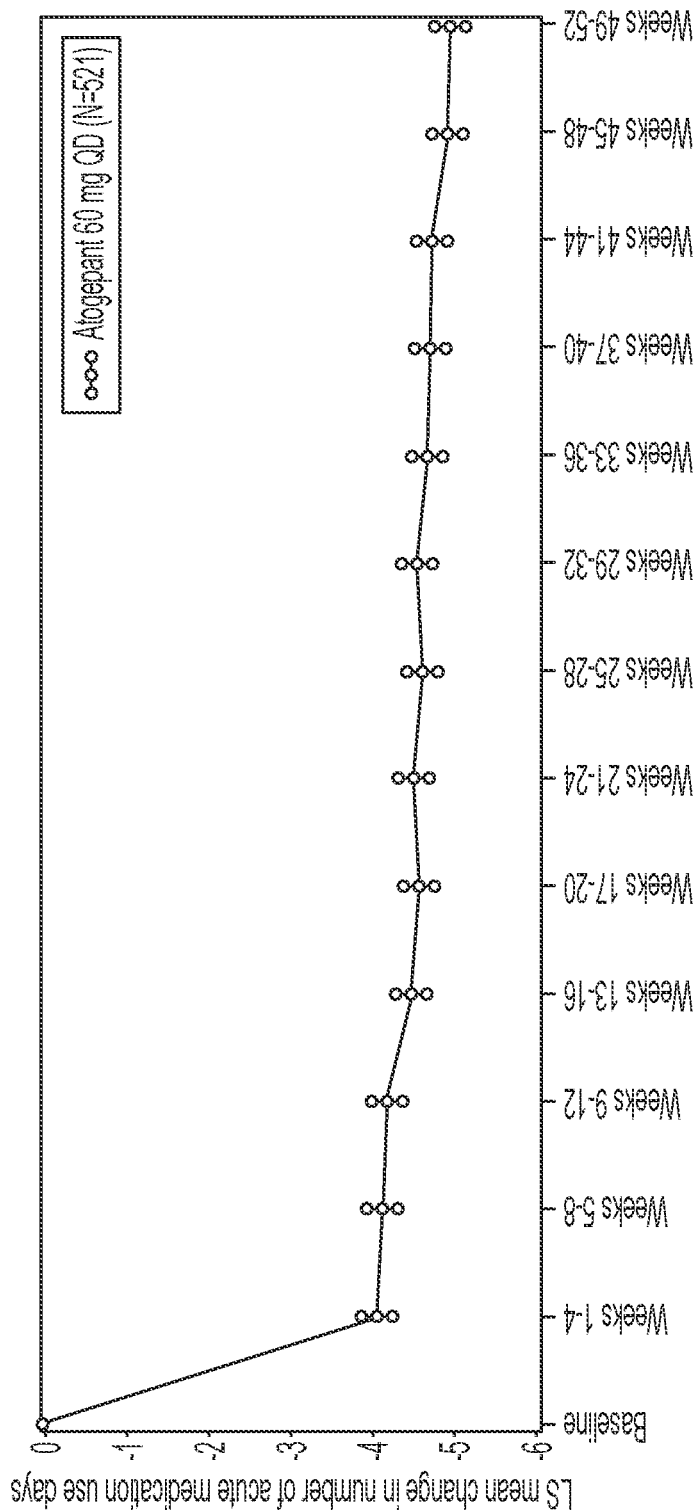
FIG. 14 shows the LS mean change from baseline in monthly acute medication use days at each monthly period (mITT population) in the 52-week long-term safety study of atogepant. Administration of 60 mg atogepant led to a rapid reduction in monthly acute medication use days in month 1, with additional gradual improvement over time through week 52.

FIG. 14 shows the LS mean change from baseline in monthly acute medication use days at each monthly period (mITT population), which is also summarized in Table 27.

TABLE 27

Change from Baseline in Monthly Acute Medication Use Days At Each Monthly Period (mITT Population)

| | | Atogepant 60 mg QD (N = 521) | |
|---|---|---|---|
| Derived Visit | N | Observed Value Mean (SD) | Change from Baseline LS means (95% CI) - MMRM |
| Baseline | 521 | 6.59 (3.27) | — |
| Weeks 1-4 | 513 | 2.60 (3.00) | −4.04 (−4.28, −3.81) |
| Weeks 5-8 | 490 | 2.49 (3.06) | −4.11 (−4.37, −3.86) |
| Weeks 9-12 | 466 | 2.39 (2.90) | −4.18 (−4.42, −3.94) |
| Weeks 13-16 | 440 | 2.09 (2.58) | −4.46 (−4.68, −4.23) |
| Weeks 17-20 | 419 | 1.92 (2.68) | −4.56 (−4.80, −4.33) |
| Weeks 21-24 | 417 | 2.01 (2.65) | −4.49 (−4.72, −4.25) |
| Weeks 25-28 | 398 | 1.90 (2.78) | −4.59 (−4.84, −4.34) |
| Weeks 29-32 | 390 | 1.84 (2.64) | −4.54 (−4.79, −4.28) |
| Weeks 33-36 | 379 | 1.75 (2.54) | −4.66 (−4.90, −4.41) |
| Weeks 37-40 | 375 | 1.75 (2.52) | −4.68 (−4.93, −4.44) |
| Weeks 41-44 | 363 | 1.69 (2.62) | −4.71 (−4.97, −4.46) |
| Weeks 45-48 | 352 | 1.51 (2.46) | −4.90 (−5.15, −4.66) |
| Weeks 49-52 | 335 | 1.50 (2.73) | −4.93 (−5.20, −4.66) |

Figure 15A:
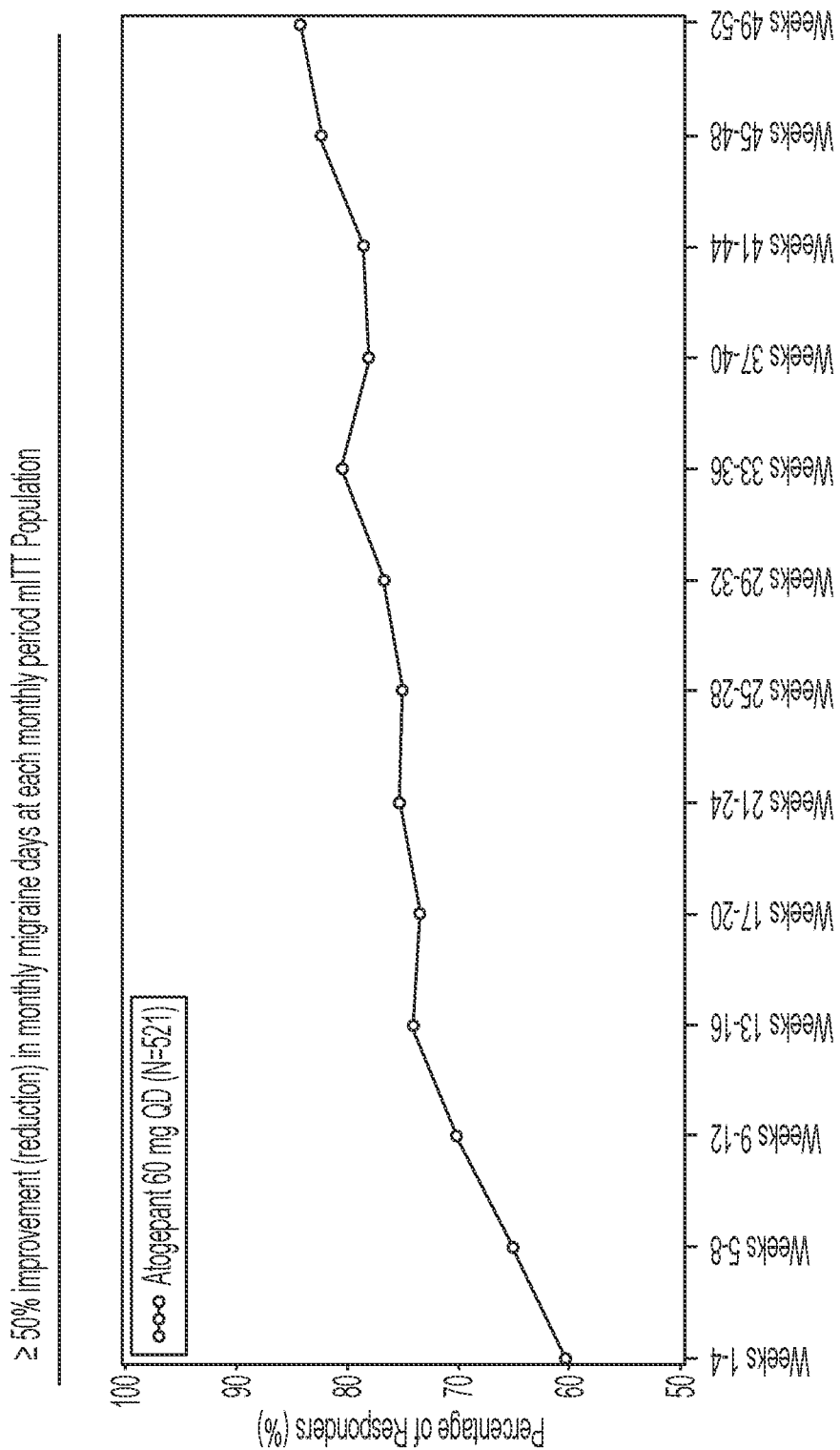
FIG. 15A shows the results for ≥50% improvement (reduction) in monthly migraine days at each monthly period (mITT population).

FIG. 15A shows the results for ≥50% improvement (reduction) in monthly migraine days at each monthly period (mITT population) which is also summarized in Table 28.

TABLE 28

≥50% Improvement (reduction) in monthly migraine days at each monthly period (mITT population)

| Derived Visit | Atogepant 60 mg QD (N = 521) Responder n/N1 (%) |
|---|---|
| Weeks 1-4 | 310/513 (60.4) |
| Weeks 5-8 | 319/490 (65.1) |
| Weeks 9-12 | 327/466 (70.2) |
| Weeks 13-16 | 326/440 (74.1) |
| Weeks 17-20 | 308/419 (73.5) |
| Weeks 21-24 | 314/417 (75.3) |
| Weeks 25-28 | 299/398 (75.1) |
| Weeks 29-32 | 299/390 (76.7) |
| Weeks 33-36 | 305/379 (80.5) |
| Weeks 37-40 | 293/375 (78.1) |
| Weeks 41-44 | 285/363 (78.5) |
| Weeks 45-48 | 290/352 (82.4) |
| Weeks 49-52 | 282/335 (84.2) |

Figure 15B:
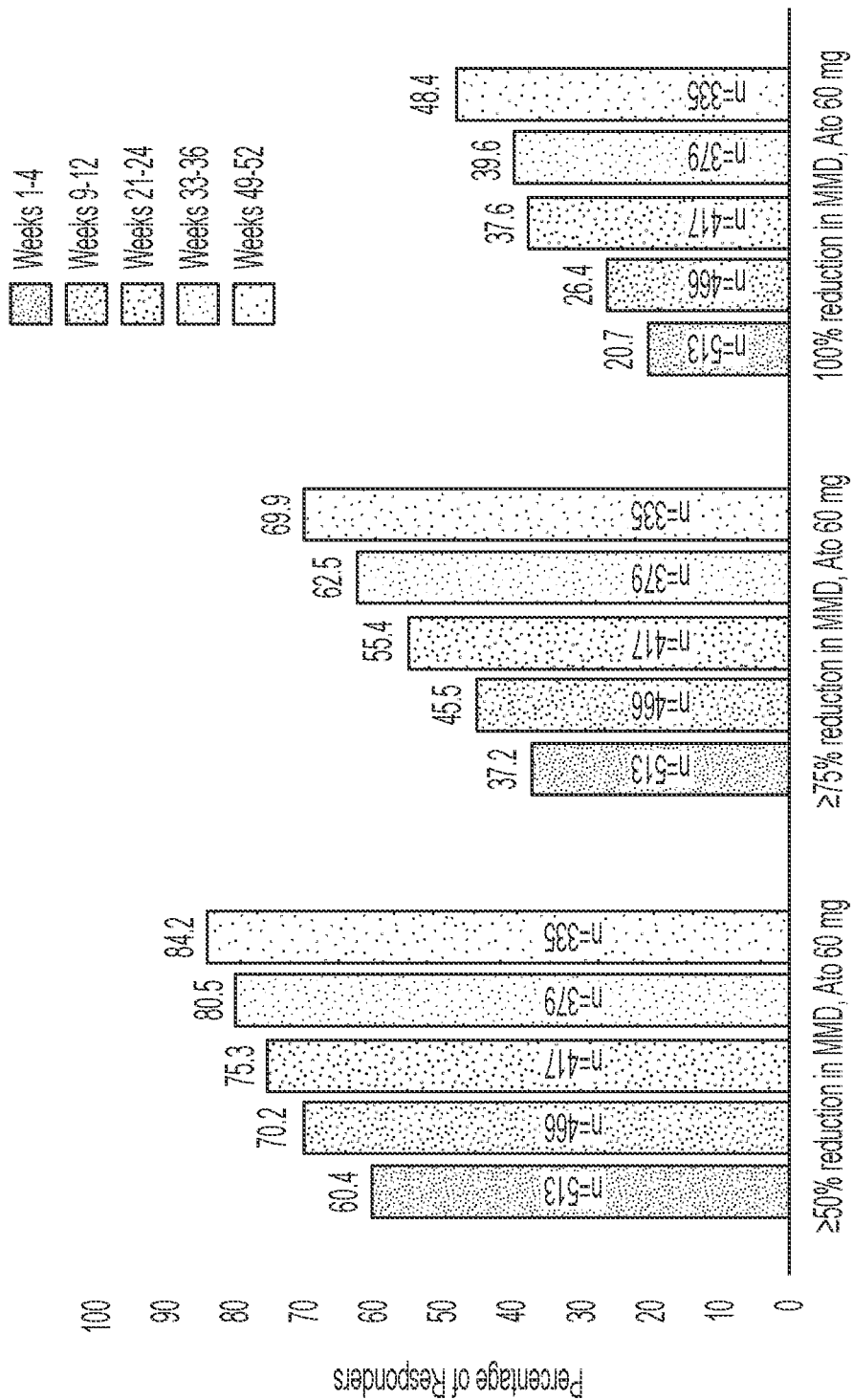
FIG. 15B shows the proportion of responders with ≥50%, ≥75%, and ≥100% reduction in monthly migraine days (MMDs) (mITT population, observed cases) in the 52-week, multicenter, open-label trial (Study B) of atogepant in adult patients with episodic migraine with or without aura.

The proportion of responders with ≥50%, ≥75%, and 100% reduction in MMDs (mITT population, observed cases), are shown in FIG. 15B. Of participants who remained in the trial at weeks 49-52, 84.2% (282/335) experienced ≥50% reduction in MMDs, 69.9% (234/335) experienced ≥75% reduction in MMDs, and 48.4% (162/335) experienced a 100% reduction in MMDs. Proportions of responders in each category increased over the course of the trial.

As shown above, results demonstrate that atogepant is well-tolerated in this 52-week open label study. ICH E1 exposure requirements for 6-month exposure (≥300 patients) and one-year exposure (≥100 patients) are met. The efficacy of atogepant treatment in terms of reduction in monthly migraine days, reduction in monthly headache days, reduction in acute medication use days, and ≥50% responder rate are well-maintained for the one-year atogepant 60 mg QD treatment. A slight improvement over time was observed for the four endpoints.

The change from baseline in AIM-D PDA and PI domains for the first and last timepoints assessed are shown in Table 29. The negative change scores with confidence intervals that exclude 0 indicate a significant reduction in impairment due to migraine in PDA and PI.

TABLE 29

LS mean changes from baseline in AIM-D Performance of Daily Activities (PDA)
and Physical Impairment (PI) Domain scores (mITT population, MMRM analysis)

| Weeks | N | AIM-D PDA Domain Baseline LS mean (SE) = 15.0 (8.80); n = 445 | | AIM-D PI Domain Baseline LS Mean (SE) = 11.4 (8.85); n = 445 | |
|---|---|---|---|---|---|
| | | LS Mean (SE) change from baseline | 95% CI | LS Mean (SE) Change from baseline | 95% CI |
| 1-4 | 397 | −7.61 (0.329) | (−8.86, −6.96) | −5.56 (0.290) | (−6.13, −4.99) |
| 49-52 | 247 | −10.17 (0.370) | (−10.90, −9.44) | −7.20 (0.357) | (−7.91, −6.50) |

Figure 16A:
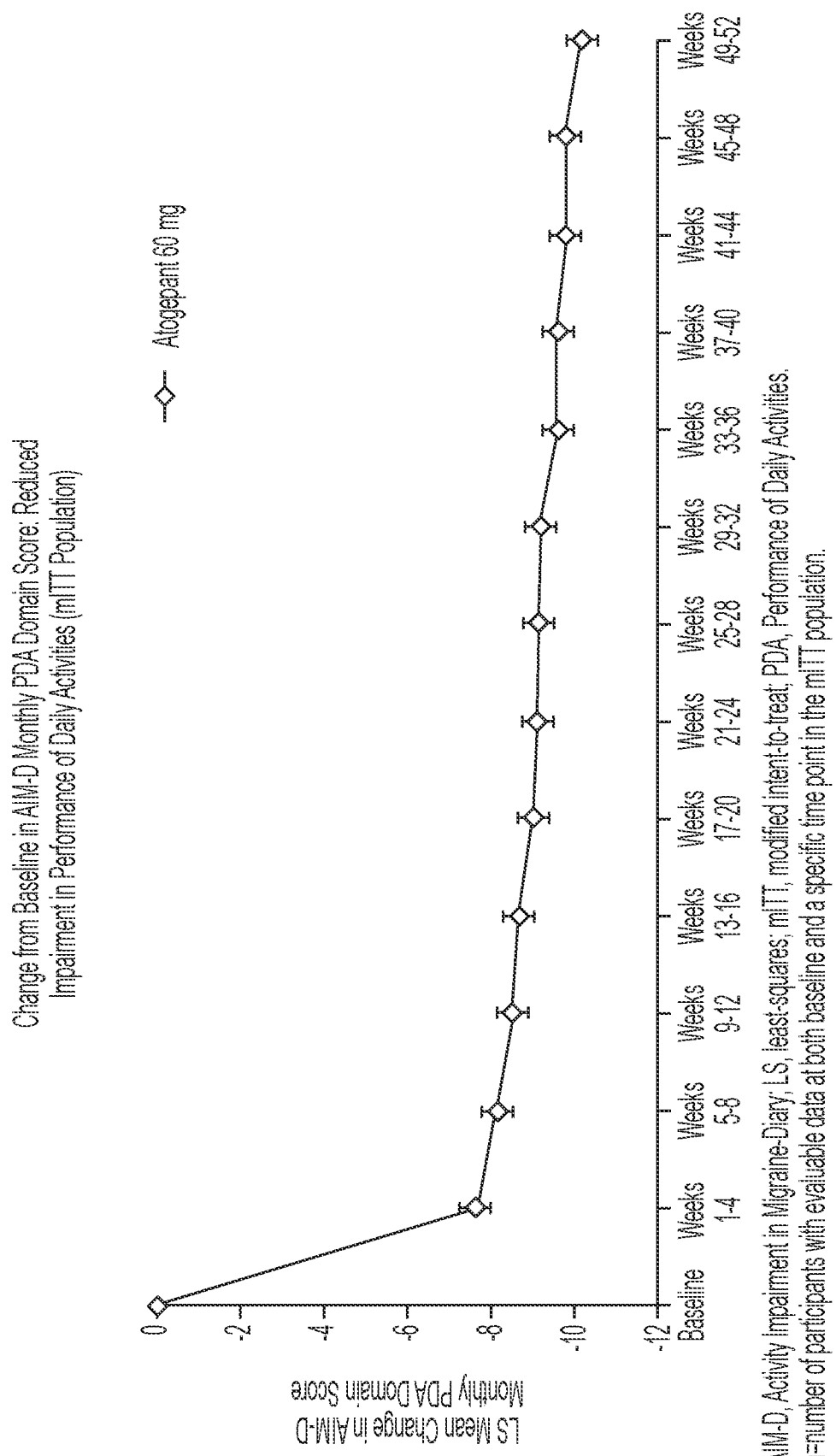
FIG. 16A shows the change from baseline in AIM-D monthly PDA domain score: reduced impairment in performance of daily activities (mITT population).
Figure 16B:
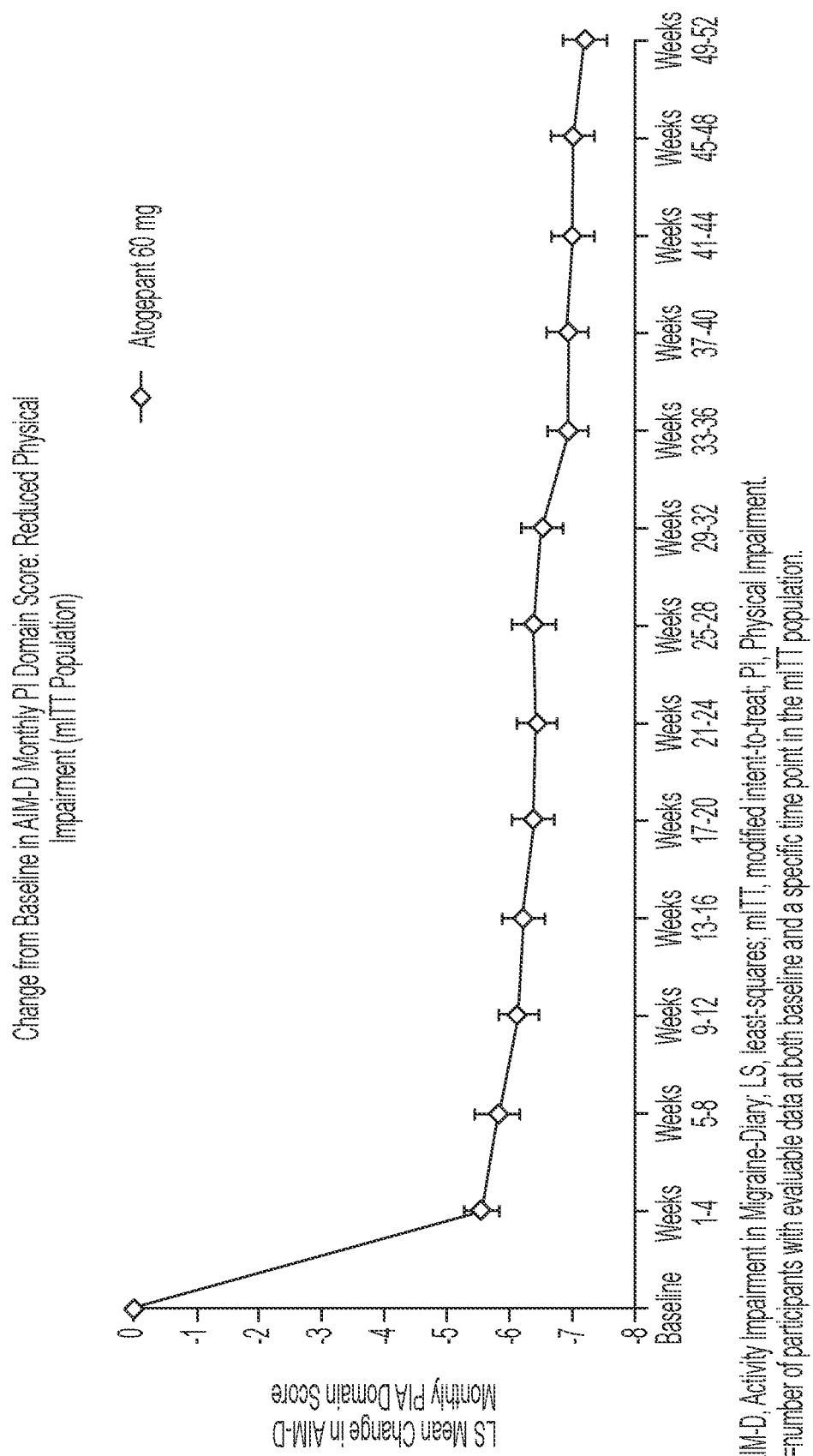
FIG. 16B shows the change from baseline in AIM-D monthly PI domain score: reduced physical impairment (mITT population) over the 52-week, multicenter, open-label, 52-week, long-term safety trial (Study B) of atogepant in adult patients with episodic migraine with or without aura.

The change from baseline in AIM-D monthly PDA domain score (mITT population) is shown in FIG. 16A and Table 30. The change from baseline in AIM-D monthly PI domain score (mITT population) is shown in FIG. 16B and Table 31. The LS mean change from baseline in the AIM-D PDA and PI scores demonstrated an early and consistent reduction in impairment due to migraine over the 52 week trial. Change scores with confidence intervals excluding zero were present at each time point assessed, indicating significant reduction in impairment due to migraine during the 52-week trial.

TABLE 30

Change from Baseline in AIM-D Monthly PDA
Domain Score: Reduced Impairment in Performance
of Daily Activities (mITT Population)

| Weeks | n | LS Mean Δ from baseline | 95% CI |
|---|---|---|---|
| 1-4 | 397 | −7.61 | −8.26, −6.96 |
| 5-8 | 360 | −8.16 | −8.89, −7.42 |
| 9-12 | 346 | −8.53 | −9.22, −7.84 |
| 13-16 | 334 | −8.66 | −9.37, −7.94 |
| 17-20 | 323 | −9.02 | −9.72, −8.32 |
| 21-24 | 313 | −9.11 | −9.80, −8.43 |
| 25-28 | 301 | −9.16 | −9.88, −8.44 |
| 29-32 | 288 | −9.22 | −9.93, −8.51 |
| 33-36 | 288 | −9.61 | −10.28, −8.94 |
| 37-40 | 283 | −9.61 | −10.27, −8.95 |
| 41-44 | 273 | −9.77 | −10.48, −9.06 |
| 45-48 | 262 | −9.79 | −10.48, −9.10 |
| 49-52 | 247 | −10.17 | −10.90, −9.44 |

TABLE 31

Change from Baseline in AIM-D Monthly PI Domain Score:
Reduced Physical Impairment (mITT Population)

| Weeks | n | LS Mean Δ from baseline | 95% CI |
|---|---|---|---|
| 1-4 | 397 | −5.56 | −6.13, −4.99 |
| 5-8 | 360 | −5.82 | −6.50, −5.13 |
| 9-12 | 346 | −6.13 | −6.75, −5.51 |
| 13-16 | 334 | −6.22 | −6.87, −5.56 |
| 17-20 | 323 | −6.38 | −7.04, −5.73 |
| 21-24 | 313 | −6.43 | −7.08, −5.77 |
| 25-28 | 301 | −6.40 | −7.09, −5.72 |
| 29-32 | 288 | −6.51 | −7.18, −5.84 |
| 33-36 | 288 | −6.94 | −7.57, −6.31 |
| 37-40 | 283 | −6.93 | −7.56, −6.30 |
| 41-44 | 273 | −7.01 | −7.68, −6.34 |
| 45-48 | 262 | −7.02 | −7.68, −6.36 |
| 49-52 | 247 | −7.20 | −7.91, −6.50 |

Figure 17:
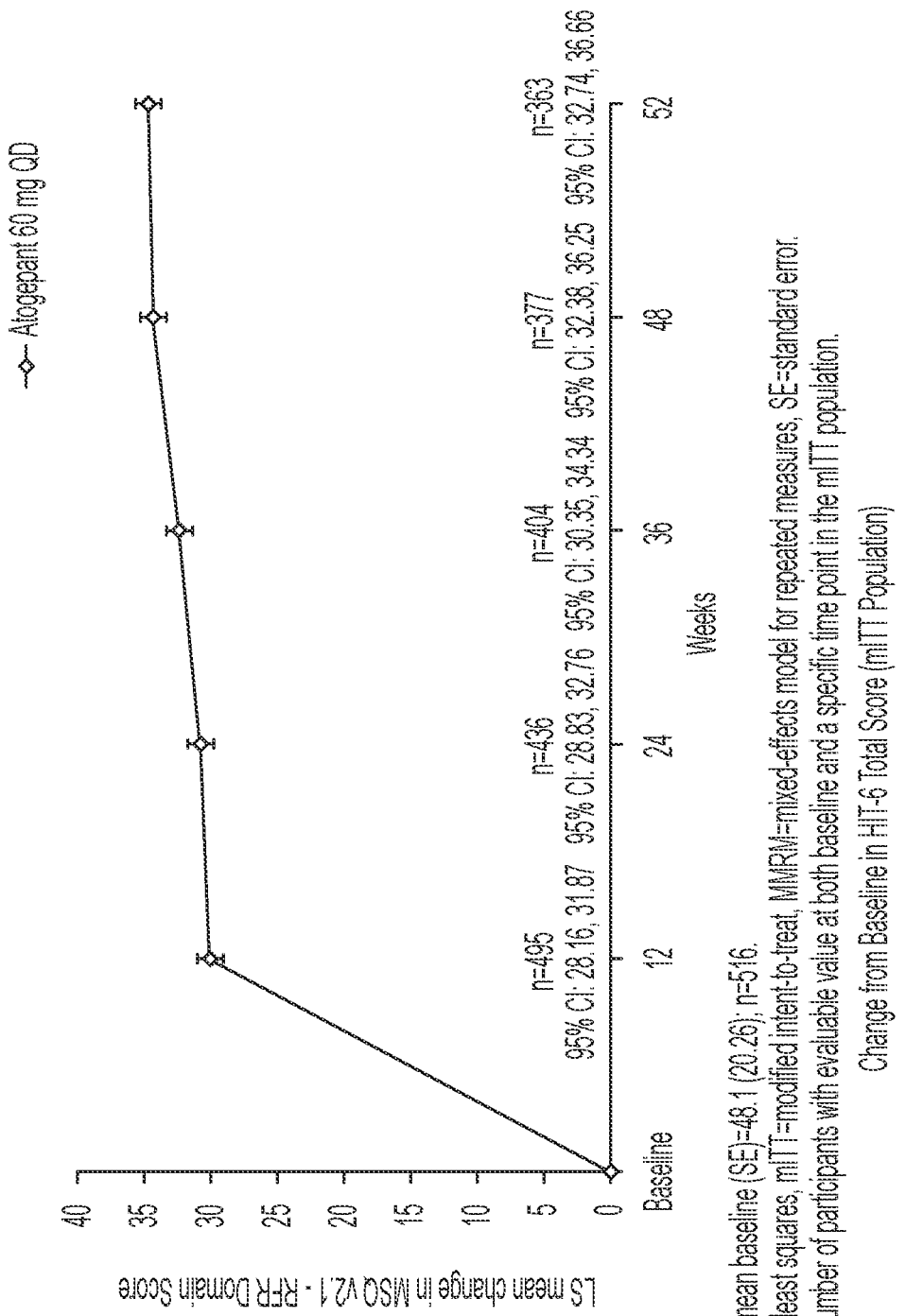
FIG. 17 shows the LS mean change from baseline in MSQ v 2.1-RFR Domain Score (mITT population, MMRM analysis) over the 52-week, multicenter, open-label trial (Study B) of atogepant in adult patients with episodic migraine with or without aura. Findings indicated rapid improvement over the first 12 weeks, and sustained improvement from 12 to 52 weeks. Non-zero confidence intervals throughout indicate significant improvement at each time point assessed.

The Migraine-Specific Quality of Life Questionnaire version 2.1 (MSQv2.1) Role Function-Restrictive (RFR) domain least squares (LS) mean (standard error [SE]) at baseline was 48.1 (20.26) and LS mean changes from baseline throughout the trial are shown in FIG. 17 and in Table 32. Findings indicated rapid improvement over the first 12 weeks and sustained improvement from 12 to 52 weeks, and non-zero confidence intervals throughout indicate significant improvement at each timepoint assessed.

TABLE 32

Change from Baseline in MSQ v2.1
Domain Score (mITT Population)

| Weeks | n | LS Mean Δ from baseline | 95% CI |
|---|---|---|---|
| 12 | 495 | 30.02 | 28.16, 31.87 |
| 24 | 436 | 30.79 | 28.83, 32.76 |
| 36 | 404 | 32.34 | 30.35, 34.34 |
| 48 | 377 | 34.32 | 32.38, 36.25 |
| 52 | 363 | 34.70 | 32.74, 36.66 |

Figure 18:
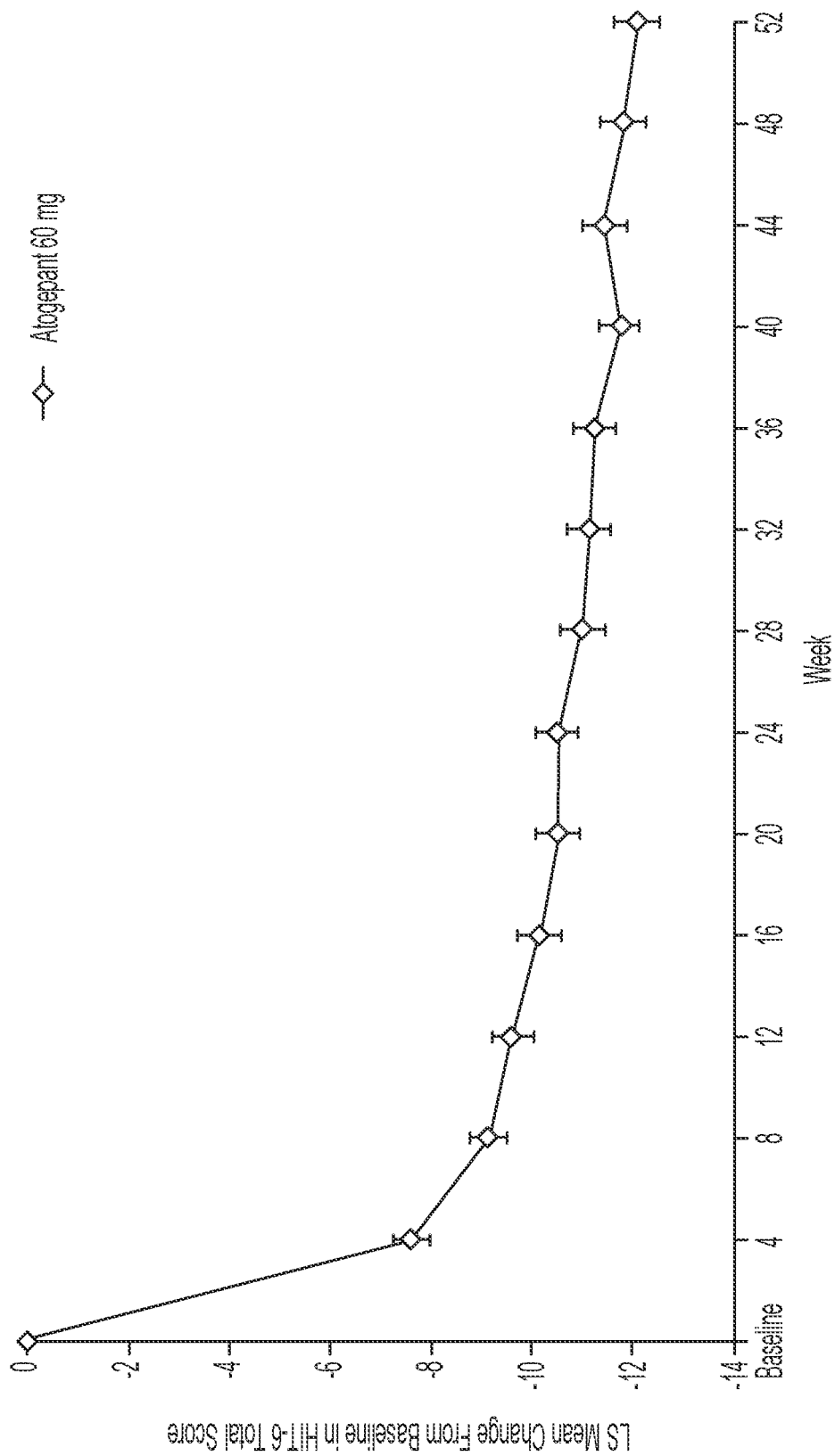
FIG. 18 shows the change from baseline in HIT-6 Total Score (mITT population).

The mean (SE) HIT-6 total score at baseline was 64.07 (4.89) and the LS mean change (95% confidence interval) at Week 4 was −7.63 (−8.31, −6.95) and at Week 52 was −12.10 (−12.98, −11.22), demonstrating reductions in headache impact. The proportion of HIT-6 responders (≥5 points from baseline) were 59.92% and 80.77% of participants in the first (week 4) and last (week 52) timepoints assessed, respectively. Change from baseline in HIT-6 Total Score (mITT Population) is shown in FIG. 18 and Table 33. HIT-6 total score responder rates (mITT) population are shown in Table 33. A responder on the HIT-6 was defined as a participant with a ≥5 point improvement from baseline.

TABLE 33

Change from Baseline in HIT-6 Total Score (mITT Population)

| Week | n | LS Mean Δ from baseline | 95% CI |
|---|---|---|---|
| 4 | 514 | −7.63 | −8.31, −6.95 |
| 8 | 491 | −9.14 | −9.87, −8.42 |
| 12 | 471 | −6.60 | −10.33, −8.87 |
| 16 | 448 | −10.15 | −10.93, −9.37 |
| 20 | 442 | −10.56 | −11.35, −9.76 |
| 24 | 423 | −10.55 | −11.39, −9.71 |
| 28 | 418 | −10.99 | −11.83, −10.15 |
| 32 | 407 | −11.15 | −11.98, −10.32 |
| 36 | 402 | −11.29 | −12.14, −10.43 |
| 40 | 394 | −11.76 | −12.60, −10.91 |
| 44 | 384 | −11.46 | −12.32, −10.60 |
| 48 | 377 | −11.86 | −12.72, −10.99 |
| 52 | 364 | −12.10 | −12.98, −11.22 |

TABLE 34

HIT-6 Total Score Responder Rates

| Week | Responders | Nonresponders | Total (N) | % Responder |
|---|---|---|---|---|
| 4 | 308 | 206 | 514 | 59.92 |
| 8 | 327 | 164 | 491 | 66.60 |
| 12 | 326 | 145 | 471 | 69.21 |
| 16 | 321 | 127 | 448 | 71.65 |
| 20 | 327 | 115 | 442 | 73.98 |
| 24 | 313 | 110 | 423 | 74.00 |
| 28 | 320 | 98 | 418 | 76.56 |
| 32 | 317 | 90 | 407 | 77.89 |
| 36 | 304 | 98 | 402 | 75.62 |
| 40 | 318 | 76 | 394 | 80.71 |
| 44 | 301 | 83 | 384 | 78.39 |
| 48 | 302 | 75 | 377 | 80.11 |
| 52 | 294 | 70 | 364 | 80.77 |

Total (N) = Number of participants with non-missing values at the post-baseline analysis visit.

Long-term daily use of atogepant 60 mg for the preventive treatment of migraine was associated with reductions in the impact of migraine on the AIM-D in performance of daily activities and physical impairment, improvements in migraine-specific quality of life on the RFR domain, and reductions in the impact of headaches as assessed by changes from baseline, which were significant as indicated by non-zero confidence intervals. Improvements were observed at the earliest time point assessed and increased over the 52-week trial.

Example 3

As discussed in Example 1, a phase 3 trial (Study A) demonstrated that atogepant dosed once daily results in a clinically meaningful reduction in mean monthly migraine days. An open-label extension study for trial completers evaluated the long-term safety and tolerability of oral atogepant 60 mg daily for the prevention of migraine in participants with episodic migraine.

Participants in this trial (Study C) rolled over from the lead in trial (Study A) and were treated with atogepant 60 mg once daily for 40-weeks, with a 4-week safety follow-up period. Only safety data were collected.

Of 695 participants screened, a total of 685 participants took at least one dose of study medication and were included in the safety population. Overall, the mean age was 41.8 years. Female participants accounted for 88.2% of the Safety Population. White and Black or African American patients accounted for 84.4% and 12.6%, respectively. Mean BMI was 30.58 kg/m$^2$. Demographics data for the Safety Population are summarized in Table 35.

TABLE 35

Demographics and Baseline Characteristics (Safety Population)

| Parameter | Atogepant 60 mg QD<br>N = 685 |
|---|---|
| Age (years) | |
| Mean (SD) | 41.8 years (12.30) |
| Sex, n (%) | |
| Male | 81 (11.8%) |
| Female | 604 (88.2) |
| Race Group, n (%) | |
| White | 578 (84.4) |
| Black or African American | 86 (12.6) |

TABLE 35-continued

Demographics and Baseline Characteristics (Safety Population)

| Parameter | Atogepant 60 mg QD<br>N = 685 |
|---|---|
| Asian | 9 (1.3) |
| American Indian or Alaska Native | 3 (0.4) |
| Native Hawaiian or Other Pacific Islander | 0 |
| Multiple [1] | 8 (1.2) |
| Missing | 1 (0.1) |
| Race Group, n (%) | |
| White | 578 (84.4) |
| All other races | 106 (15.5) |
| Missing | 1 (0.1) |
| Ethnicity, n (%) | |
| Hispanic or Latino | 54 (7.9) |
| Not Hispanic or Latino | 631 (92.1) |
| Weight (kg) | |
| Mean (SD) | 84.21 (23.267) |
| N | 685 |
| BMI (kg/m$^2$) | |
| Mean (SD) | 30.58 (7.820) |
| n | 685 |

[1] Participants who reported multiple races are only included in the "Multiple" category.
N = number of patients in the safety population
n = Number of participants within a specific category
Percentages are calculated as 100 × (n/N)

The majority of participants (74.6%) completed the open label treatment period. Overall, 62.5% of participants experienced a treatment-emergent adverse event (TEAE), with 8.8% considered treatment-related by the investigator; serious adverse events occurred in 3.4% of participants, none of which were treatment related. Table 36 reports the most frequent AEs leading to discontinuation; Table 37 reports the most frequent TEAEs observed. No deaths and no hepatic safety issues were observed.

TABLE 36

Overall Summary of Adverse Events - Safety Population

| Category | Total<br>(N = 685) n/N (%) |
|---|---|
| Treatment-emergent adverse event (TEAE) | 428 (62.5) |
| Deaths | 0 (0.0) |
| Treatment-emergent serious adverse events (SAE) | 23 (3.4) |
| Treatment-related TEAE | 60 (8.8) |
| TEAE Leading to Study Discontinuation [1, 2] | 22 (3.2) |
| Nausea | 3 (0.4) |
| Abdominal pain | 2 (0.3) |
| Vomiting | 2 (0.3) |
| Weight Decreased | 2 (0.3) |
| Dizziness | 2 (0.3) |
| Migraine | 2 (0.3) |

Participants are counted only once within each category.
N = number of participants in the Safety Population
n = number of participants within a specific category
Percentages are calculated as 100 × (n/N)

[1] The inset AEs represent the most frequent AEs leading to discontinuation in the extension study.

[2] Three patients with AE onset date in the lead-in trial rolled over to the extension study and discontinued in the extension study.

TABLE 37

Most Frequent (≥2%) Treatment Emergent Adverse
Events (TEAEs) by Preferred Term - Safety Population

| TEAEs by Preferred Term | Atogepant 60 mg QD (N = 685) n (%) |
|---|---|
| Upper respiratory tract infection | 38 (5.5) |
| Urinary tract infection | 36 (5.3) |
| Nasopharyngitis | 33 (4.8) |
| Sinusitis | 25 (3.6) |
| Constipation | 23 (3.4) |
| Nausea | 23 (3.4) |
| Weight decreased | 18 (2.6) |
| Back pain | 17 (2.5) |
| Dizziness | 17 (2.5) |
| Influenza | 17 (2.5) |
| Arthralgia | 15 (2.2) |
| Corona virus infection | 15 (2.2) |
| Gastroenteritis | 15 (2.2) |
| Anxiety | 14 (2.0) |
| Bronchitis | 14 (2.0) |
| Vomiting | 14 (2.0) |

Participants are counted only once within each preferred term.
N = number of participants in the Safety Population
n = number of participants within a specific category
Percentages are calculated as 100 × (n/N).

The study supported that atogepant 60 mg once daily is safe and well tolerated. The study results contributed 538 participants exposed to atogepant for 6 months and 509 participants exposed to atogepant for 9 months.

Example 4

The populations of Study A (described in Example 1) and Study B (described in Example 2) were analyzed for weight-related changes over the course of treatment.

Data was also evaluated from Study C (described in Example 3) and Study D, a Phase 2b/3 clinical trial evaluating the efficacy, safety, and tolerability of orally administered atogepant. In Study D, after a 28 day baseline period, a total of 652 patients were randomized 1:2:2:2 to receive either atogepant 10 mg (n=94), atogepant 30 mg (n=185), atogepant 60 mg (n=187) or placebo (n=186).

In the atogepant Study A population, 44.8% of patients had a BMI of ≥30 kg/m$^2$, and 58.6% of patients had a BMI≥27 kg/m$^2$ with obesity-related comorbidities (e.g., Type 2 diabetes, hypertension, dyslipidemia, sleep apnea, cardiovascular disease). In the atogepant Study B population, 45.3% of patients had BMI≥30 kg/m$^2$, and 54.9% of patients had BMI≥27 kg/m$^2$ and obesity-related comorbidities.

Figure 19:
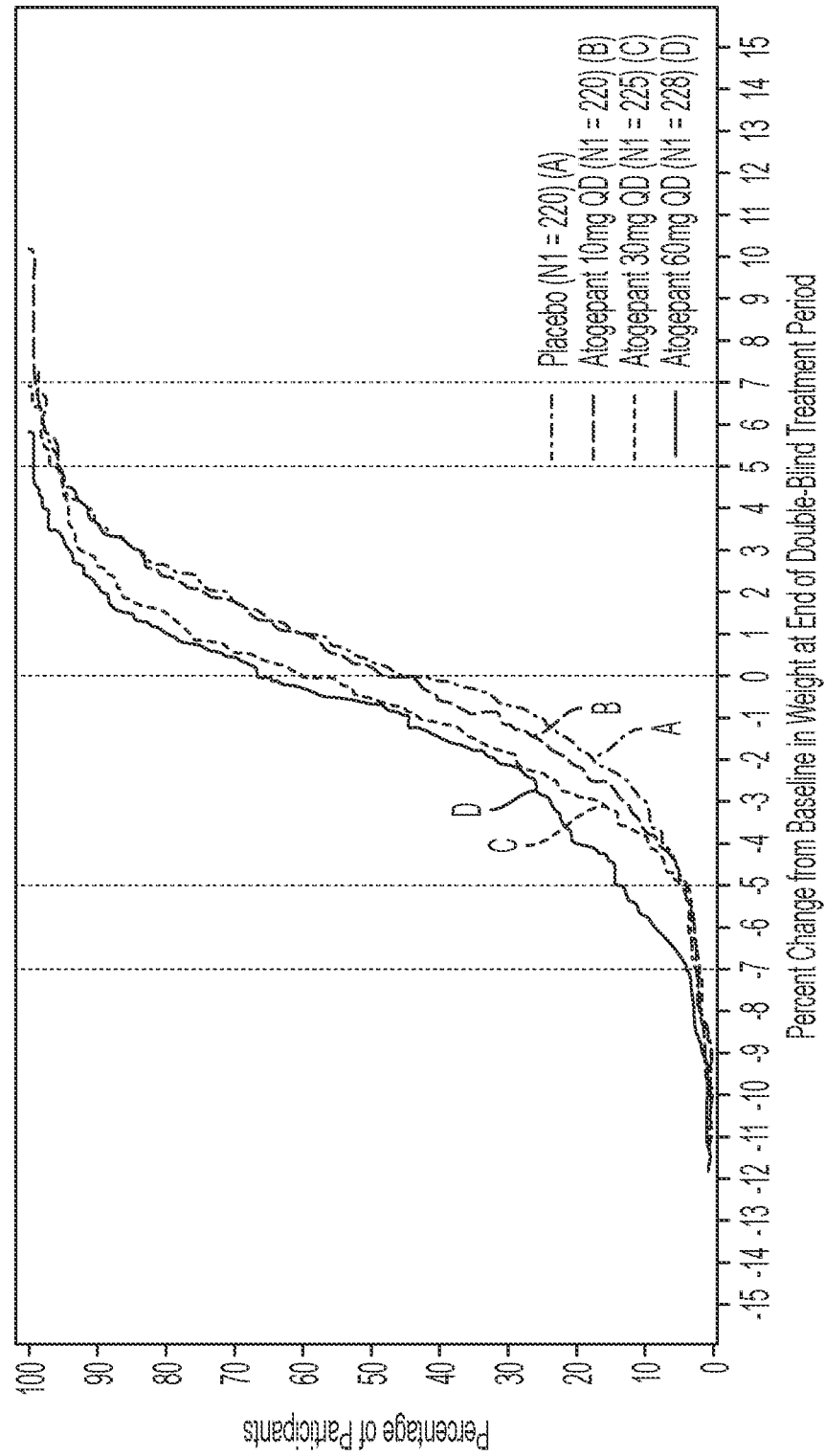
FIG. 19 shows CDF plots for percentage change from baseline in body weight (kg) at the end of the double-blind treatment period for Study A (safety population). Statistically significant weight loss was observed in the atogepant 30 mg once daily and 60 mg once daily groups compared with placebo.

Statistically significant weight loss was observed in the atogepant 30 mg once daily and 60 mg once daily groups compared with placebo in Study A. The LS mean difference for percentage change from baseline in body weight at the end of the treatment period was 0.98% (p=0.0005) in the atogepant 30 mg once daily group and 1.64% (p<0.0001) in the atogepant 60 mg once daily group. CDF plots for percentage change from baseline in body weight (kg) at the end of the double-blind treatment period (week 12) for Study A (safety population) are shown in FIG. 19.

Figure 20:
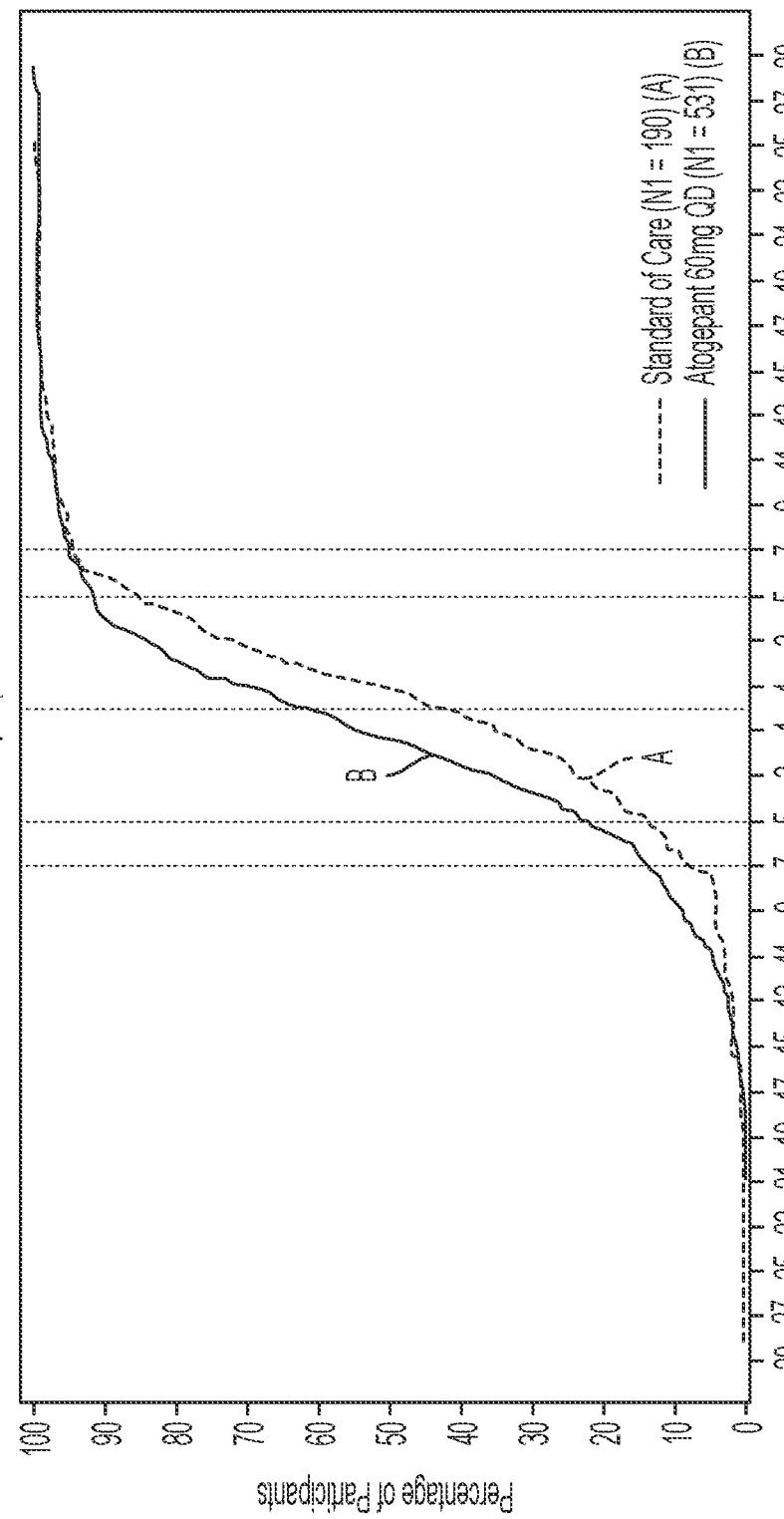
FIG. 20 shows CDF plots for percentage change from baseline in body weight (kg) at the end of the open-label treatment period for Study B (safety population).
Figure 21:
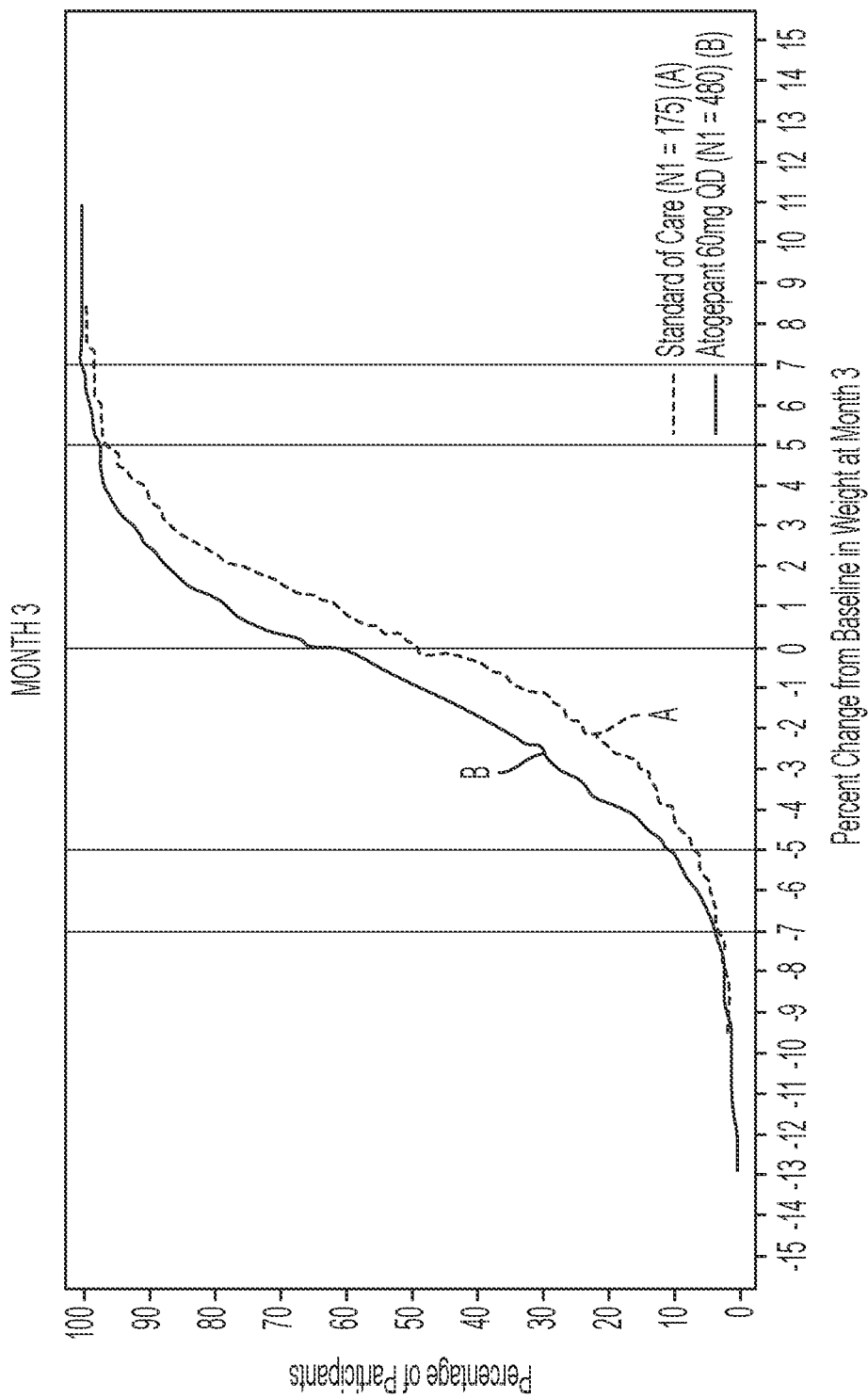
FIGS. 21-24 show CDF plots of weight loss for the safety population in the Study B long-term safety study. In particular.
Figure 22:
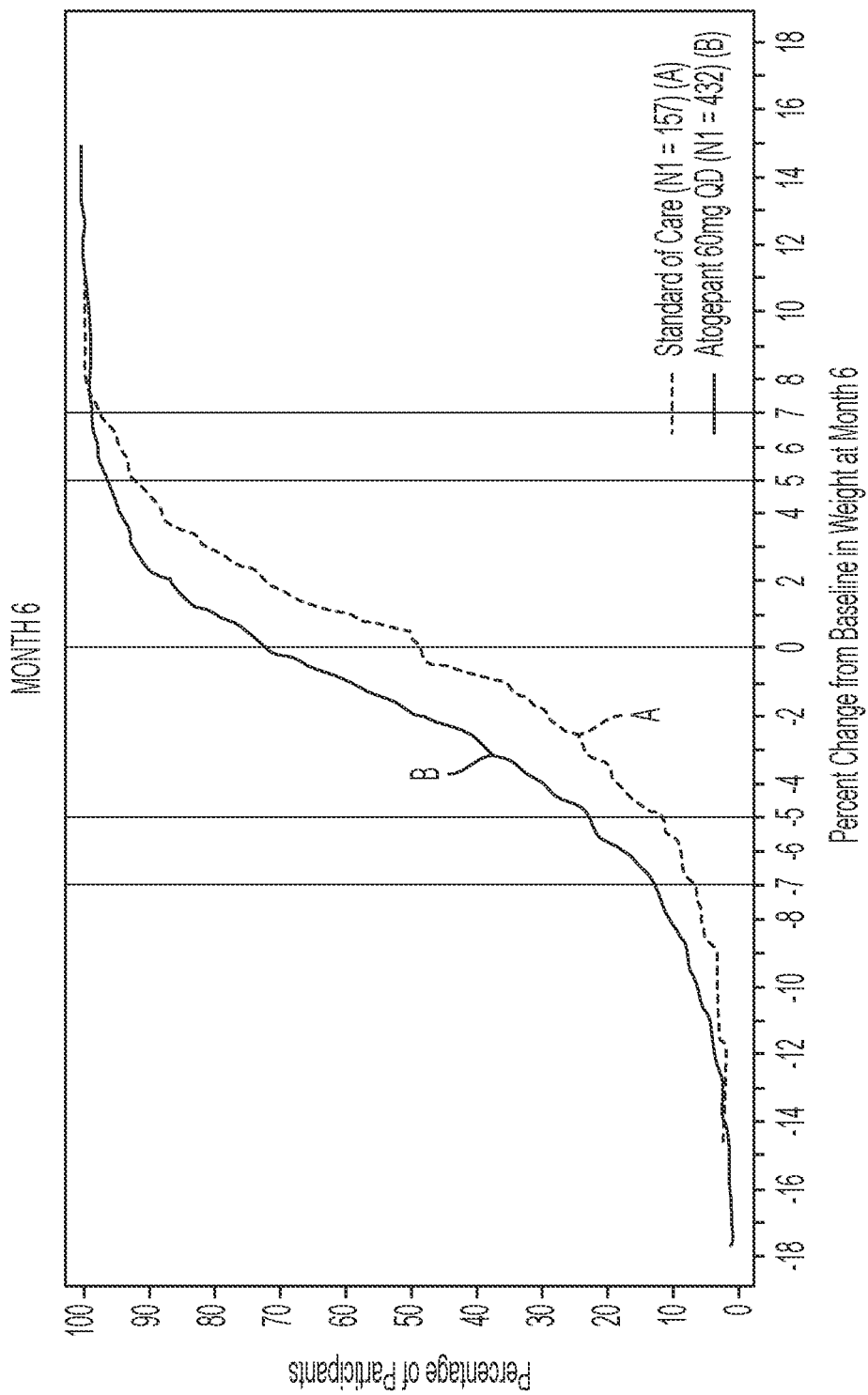
Figure 23:
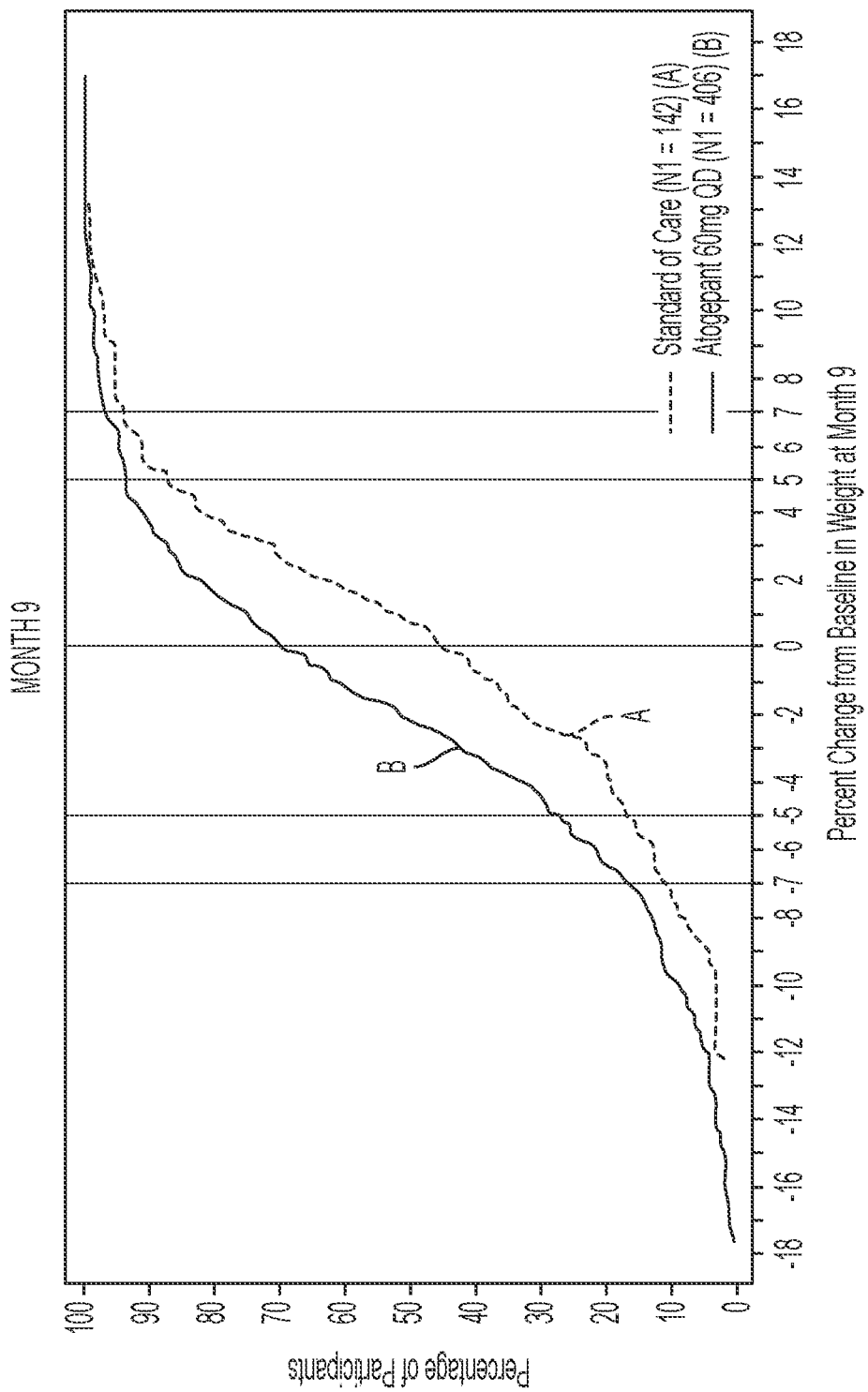
Figure 24:
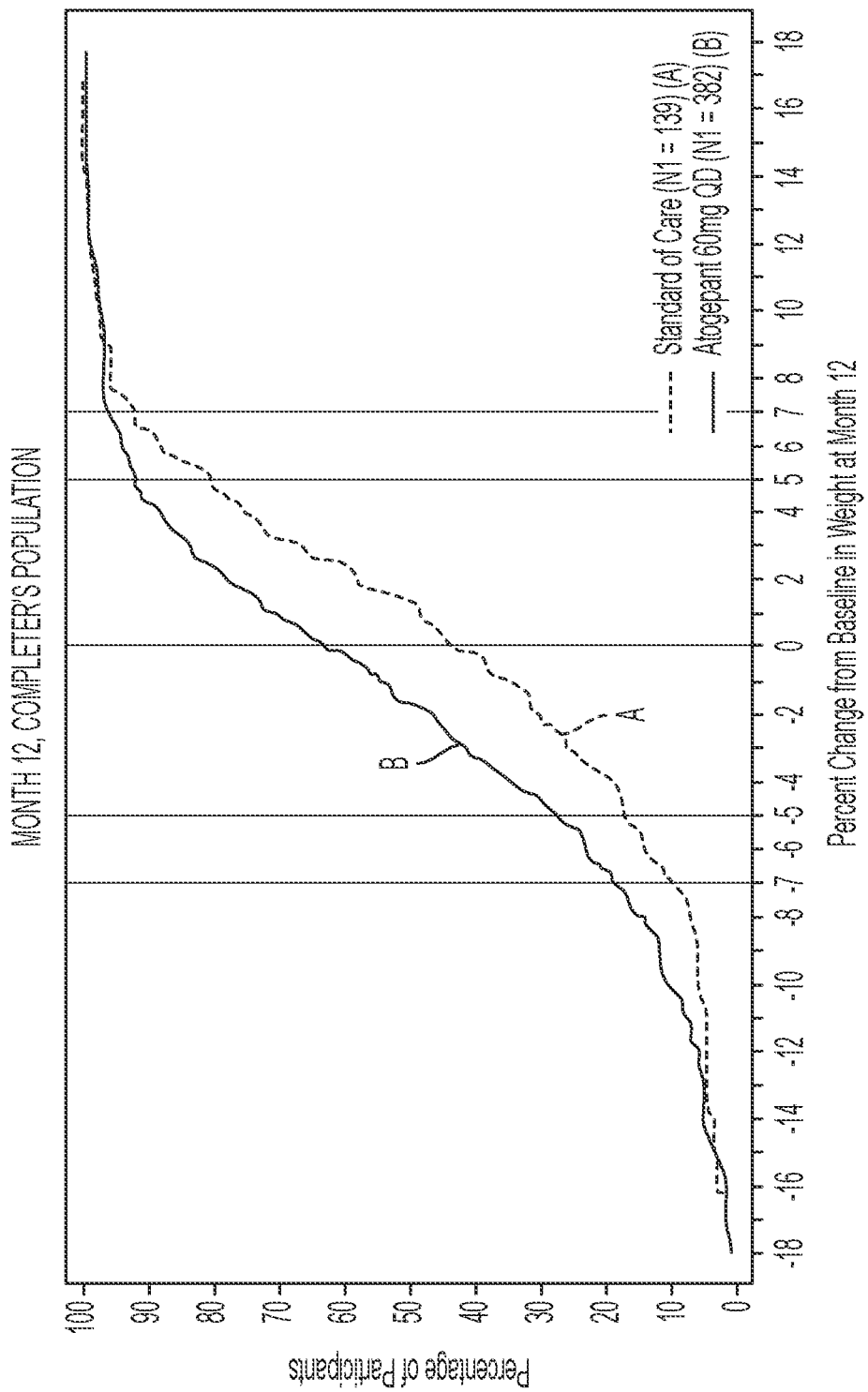

Treatment with atogepant over the 52-week treatment period was associated with modest weight loss in Study B. Statistically significant weight loss was observed in the atogepant 60 mg once daily group compared with SOC. The LS mean difference for percentage change from baseline in body weight at the end of the treatment period versus SOC was −1.76% (p=0.0003). In addition, treatment with atogepant was associated with weight loss as measured by the percentage of participants who lost at least 5% of baseline body weight at the end of the treatment period. In Study B, the percentage of participants in the atogepant 60 mg once daily group who met this weight loss threshold was 22.4% compared with 14.2% in the SOC group. CDF plots for percentage change from baseline in body weight (kg) at the end of the open-label treatment period (week 52) for Study B (safety population) are shown in FIG. 20.

When evaluated with both study A and study CGP-MD-01 (NCT02848326), patients had a mean body weight of 83.6 kg and a mean BMI of 30.34 kg/m$^2$. In these studies, a dose-dependent mean change in body weight was observed at the end of the double-blind treatment period as follows: +0.32 kg for placebo, +0.07 kg for atogepant 10 mg, −0.40 kg for atogepant 30 mg, and −0.81 kg for atogepant 60 mg. The proportion of patients with weight decrease ≥7% at any point was 2.8% for placebo, 3.8% for atogepant 10 mg, 3.2% for atogepant 30 mg, and 4.9% for atogepant 60 mg. No patients in either study discontinued atogepant due to decreased weight.

TABLE 38

Weight Loss (Study A and Study D)

| | Placebo N = 408 | Atogepant 10 mg N = 314 | Atogepant 30 mg N = 411 | Atogepant 60 mg (N = 417) |
|---|---|---|---|---|
| Mean Change in weight by end of study (kg) | +0.40 | +0.07 | −0.40 | −0.81 |
| PCS Weight Loss >7% baseline | 11/399 (2.8%) | 12/312 (3.8%) | 13/404 (3.2%) | 20/409 (4.9%) |

TABLE 39

Weight Loss Adverse Events (CGP-MD-01 and Study A)

| TEAE | Placebo N = 408 | Atogepant 10 mg N = 314 | Atogepant 30 mg N = 411 | Atogepant 60 mg (N = 417) | All Atogepant (N = 1142) |
|---|---|---|---|---|---|
| Weight decreased | 3 (0.7%) | 1 (0.3%) | 0 | 4 (1.0%) | 5 (0.4%) |

In the 52-week open label long-term safety Study B, patients had a mean weight of 83.9 kg and a mean BMI of 30.55 kg/m$^2$. In this study, a mean change in body weight was also observed at the end of treatment period as follows: +0.20 kg for oral preventive standard of care group and −1.42 kg for the atogepant 60 mg group. The proportion of patients with weight decrease ≥7% at any point was 14.7% for the oral migraine preventive standard of care group and 24.1% for the atogepant 60 mg group. One patient (0.1%) in the long-term safety study discontinued atogepant 60 mg due to decreased weight.

TABLE 40

Weight Loss Adverse Events (Study B)

| TEAE | SOC N = 196 | Atogepant 60 mg (N = 1198) |
|---|---|---|
| Weight decreased | 3 (1.5%) | 25 (2.1%) |

Table 41 provides a subset analysis for percentage change from baseline in body weight (kg) at the end of the double-blind treatment period (week 12 (LOCF) ANCOVA) for Study A (safety population). Table 42 provides a subset analysis for 5% responders in body weight (kg) at the end of the double-blind treatment period [week 12 (LOCF) ANCOVA] for Study A (that is, Table 42 sets out a subset analysis for participants who lost at least 5% of baseline body weight at the end of the treatment period). The "Guidance Population" refers to patients with BMIs greater than or equal to 30 kg/m$^2$ or BMI greater than or equal to 27 kg/m$^2$ in the presence of obesity-related comorbidities (e.g., type 2 diabetes, hypertension, dyslipidemia, sleep apnea, cardiovascular disease).

TABLE 41

Subset Analysis for Percentage Change from Baseline in Body Weight (kg) at the end of the double-blind treatment period [week 12 (LOCF) ANCOVA] Study A, Safety Population

| Subgroup | Statistics | Placebo | Atogepant 10 mg | Atogepant 30 mg | Atogepant 60 mg |
|---|---|---|---|---|---|
| Overall | N | 222 | 221 | 228 | 231 |
| N = 902 | Baseline weight | 84.61 | 83.6 | 85.69 | 82.52 |
|  | LS Mean (SE) | 0.37 (0.20) | 0.14 (0.20) | −0.61 (0.20) | −1.27 (0.20) |
|  | LSMD vs. Placebo (95% CI) |  | −0.23 (−0.79, 0.32) | −0.98 (−1.53, −0.43) | −1.54 (−2.19, −1.09) |
|  | p value |  | 0.4138 | 0.0005 | <.0001 |
| BMI ≥30 | N | 97 | 98 | 119 | 90 |
| (S.E) | Baseline weight | 104.07 | 102.06 | 101.56 | 102.68 |
| N = 404 | LS Mean (SE) | 0.52 (0.29) | 0.14 (0.29) | −0.36 (0.26) | −1.29 (0.30) |
|  | LSMD vs. Placebo (95% CI) |  | −0.39 (−1.17, 0.40) | −0.88 (−1.63, −0.13) | −1.81 (−2.62, −1.01) |
|  | p value |  | 0.3345 | 0.021 | <.0001 |
| Guidance | N | 126 | 127 | 148 | 128 |
| Population | Baseline weight | 98.15 | 96.83 | 97.02 | 95.18 |
| (S.E) | LS Mean (SE) | 0.36 (0.27) | 0.13 (0.27) | −0.63 (0.25) | −1.40 (0.27) |
| N = 529 | LSMD vs. Placebo (95% CI) |  | −0.23 (−0.96, 0.49) | −1.00 (−1.69, −0.30) | −1.76 (−2.49, −1.04) |

TABLE 42

Subset Analysis for 5% Responders in Body Weight (kg) at the end of the double-blind treatment period [Week 12 (LOCF) ANCOVA] - Study A

| Subgroup and Statistics | Placebo | Atogepant 10 mg | Atogepant 30 mg | Atogepant 60 mg |
|---|---|---|---|---|
| Overall (N) | 222 | 221 | 228 | 231 |
| Responder, n/N1 | 9/220 (5.0) | 11/220 (5.0) | 9/225 (4.0) | 32/228 (14.0) |
| Odds Ratio vs. Placebo (95% CI) |  | 1.22 (0.50, 3.02) | 1.00 (0.39, 2.56) | 3.78 (1.76, 8.13) |
| Nominal p-value |  | 0.6613 | 0.9937 | 0.0007 |
| BMI ≥30 (N) S.E | 97 | 98 | 119 | 90 |
| Responder, n/N1 | 5/96 (5.2) | 3/97 (3.1) | 1/117 (0.9) | 8.88 (9.1) |
| Odds Ratio vs. Placebo (95% CI) |  | 0.57 (0.13, 2.47) | 0.15 (0.02, 1.34) | 1.82 (0.57, 5.82) |
| Nominal p-value |  | 0.4545 | 0.0898 | 0.312 |
| Guidance Population (N) S.E | 126 | 127 | 148 | 128 |
| Responder, n/N1 | 7/125 (5.6) | 5/126 (4.0) | 4/146 (2.7) | 17/126 (13.5) |
| Odds Ratio vs. Placebo (95% CI) |  | 0.69 (0.21, 2.26) | 0.47 (0.13, 1.66) | 2.55 (1.01, 6.44) |
| Nominal p-value |  | 0.542 | 0.2429 | 0.0479 |

Table 43 provides a subset analysis for percentage change from baseline in body weight (kg) at the end of the open label treatment period [week 52 (LOCF) Logistic Regression Approach] for Study B. Table 44 presents data regarding participants who lost at least 5% of baseline body weight (kg) at the end of the open-label treatment period [Week 52 (LOCF) ANCOVA] for Study B (safety population).

TABLE 43

Subset Analysis for Percentage Change from Baseline in Body Weight (kg) at the end of the Open-Label Treatment Period [Week 52 (LOCF) Logistic Regression Approach] - Study B Safety Population

| Subgroup | Statistics | SOC | Atogepant 60 mg QD |
|---|---|---|---|
| Overall | N | 196 | 543 |
| N = 739 | Baseline weight | 83.94 | 84.2 |
|  | LS Mean (SE) | 0.19 (0.423) | −1.57 (0.249) |
|  | LSMD vs. Placebo (95% CI) |  | −1.76 (−2.72, −0.80) |
|  | p value |  | 0.0003 |
| BMI >=30 | N | 85 | 250 |
| N = 335 | Baseline weight | 102.99 | 101.1 |
|  | LS Mean (SE) | 0.38 (0.60) | −2.27 (0.35) |
|  | LSMD vs. Placebo (95% CI) |  | −2.65 (−4.02, −1.27) |
|  | p value |  | 0.0002 |
| Guidance | N | 99 | 307 |
| Population | Baseline weight | 99.77 | 97.42 |
| (S.E) | LS Mean (SE) | 0.40 (0.55) | −2.09 (0.31) |
| N = 406 | LSMD vs. Placebo (95% CI) |  | −2.49 (−3.73, −1.26) |
|  | p value |  | <.0001 |

TABLE 44

Participants who lost at least 5% of baseline body weight (kg) at the end of the open label treatment period [week 52 (LOCF) ANCOVA] - Study B Safety Population

| Statistics | SOC | Atogepant 60 mg QD |
|---|---|---|
| Overall |  |  |
| Responder, n/N1 (%) | 27/190 (14.2) | 119/531 (22.4) |
| Odds Ratio vs. Placebo (95% CI) |  | 1.75 (1.11, 2.75) |
| Nominal p-value | — | 0.0165 |
| BMI >=30 |  |  |
| Responder, n/N1 (%) | 9/84 (10.7) | 58/247 (23.5) |
| Odds Ratio vs. Placebo (95% CI) |  | 2.56 (1.20, 5.42) |
| Nominal p-value | — | 0.0145 |
| Guidance Population |  |  |
| Responder, n/N1 | 9/98 (9.2) | 70/302 (23.2) |
| Odds Ratio vs. Placebo (95% CI) |  | 2.98 (1.43, 6.23) |
| Nominal p-value | — | 0.0036 |

As shown above, a clear dose-dependent weight reduction was observed for percentage change from baseline in body weight for Study A based on ANCOVA analysis. For Study A, the responder rate (>=5% weight loss) at week 12 was higher in the atogepant 60 mg group compared to atogepant 10 mg and 30 mg. For Study B, a clear difference in the percentages of patients who lost at least 5% of baseline body weight was observed in the atogepant 60 mg daily group (22.4%) compared to the SOC group (14.2%); it should be noted that patients in the SOC group were heterogeneous, and may have taken medications associated with weight loss, weight gain, or neither.

In Study A, baseline BMI did not affect the % weight change; the placebo-adjusted difference was consistent across BMI categories. In Study B, a slightly larger weight reduction was observed in the special populations (BMI>=30) based on ANCOVA analysis.

The time course of weight loss associated with atogepant use was also evaluated in the Study B population. FIGS. 21-24 show CDF plots at 3 months (FIG. 21), 6 months (FIG. 22), 9 months (FIG. 23), and 12 months (FIG. 24) in the safety population based on observed data. The change from baseline in weight over time for the Study B safety population is summarized in Table 45. The percentage change from baseline in weight over time for Study B (Safety Population) is shown in Table 46.

TABLE 45

Change from baseline in weight over time - Study B Safety Population

|  | Atogepant 60 mg | | SOC | |
|---|---|---|---|---|
| Week | n | Mean (SD) | n | Mean (SD) |
| 4 | 529 | −0.39 (1.79) | 189 | −0.01 (1.61) |
| 8 | 498 | −0.72 (2.29) | 180 | −0.06 (2.14) |
| 12 | 480 | −1.04 (2.76) | 175 | 0.07 (2.71) |
| 16 | 456 | −1.27 (3.24) | 172 | 0.09 (3.33) |
| 20 | 446 | −1.62 (3.81) | 166 | 0.12 (3.93) |
| 24 | 243 | −1.82 (4.10) | 157 | −0.05 (4.23) |
| 28 | 426 | −1.79 (4.41) | 150 | 0.13 (4.78) |
| 32 | 412 | −2.00 (4.79) | 147 | 0.11 (5.00) |
| 36 | 406 | −2.01 (4.82) | 142 | 0.12 (5.48) |
| 40 | 398 | −2.11 (5.62) | 140 | 0.03 (5.54) |
| 44 | 388 | −1.84 (5.22) | 141 | 0.12 (5.83) |
| 48 | 382 | −1.70 (5.28) | 139 | 0.43 (5.99) |
| 52 | 366 | −1.54 (5.33) | 131 | 0.24 (6.04) |
| End of the OL Period | 531 | −1.42 (4.87) | 190 | 0.20 (5.33) |

TABLE 46

Percentage change from baseline in weight over time - Study B, Safety Population

|  | Atogepant 60 mg | | SOC | |
|---|---|---|---|---|
| Week | n | Mean (SD) | n | Mean (SD) |
| 4 | 529 | −0.42 (2.11) | 189 | −0.04 (1.95) |
| 8 | 498 | −0.82 (2.65) | 180 | −0.13 (2.57) |
| 12 | 480 | −1.18 (3.16) | 175 | 0.08 (3.22) |
| 16 | 456 | −1.48 (3.75) | 172 | 0.13 (3.83) |
| 20 | 446 | −1.86 (4.36) | 166 | 0.15 (4.49) |
| 24 | 243 | −2.08 (4.78) | 157 | −0.07 (4.73) |
| 28 | 426 | −2.02 (5.14) | 150 | 0.10 (5.14) |
| 32 | 412 | −2.24 (5.45) | 147 | 0.10 (5.49) |
| 36 | 406 | −2.26 (5.60) | 142 | 0.14 (6.05) |
| 40 | 398 | −2.38 (6.70) | 140 | 0.00 (6.02) |
| 44 | 388 | −2.04 (6.14) | 141 | 0.13 (6.28) |
| 48 | 382 | −1.85 (6.23) | 139 | 0.53 (6.49) |
| 52 | 366 | −1.71 (6.39) | 131 | 0.33 (6.61) |
| End of the OL Period | 531 | −1.57 (5.75) | 190 | 0.19 (5.83) |

As discussed above, the SOC group was heterogeneous, and encompassed multiple potential options for standard of care medications. A comparison of atogepant 60 mg to those patients who initially took topiramate is shown in Table 47.

TABLE 47

Percentage Change from Baseline in Weight
Over Time, Study B, Safety Population

| Week | Atogepant 60 mg | | Topiramate Initial Use | |
|---|---|---|---|---|
| | n | Mean (SD) | n | Mean (SD) |
| 4 | 529 | −0.42 (2.11) | 57 | −0.57 (1.74) |
| 8 | 498 | −0.82 (2.65) | 53 | −0.93 (3.06) |
| 12 | 480 | −1.18 (3.16) | 48 | −1.17 (3.76) |
| 16 | 456 | −1.48 (3.75) | 47 | −0.57 (5.32) |
| 20 | 446 | −1.86 (4.36) | 45 | −0.94 (6.55) |
| 24 | 243 | −2.08 (4.78) | 43 | −1.53 (7.06) |
| 28 | 426 | −2.02 (5.14) | 40 | −1.35 (8.17) |
| 32 | 412 | −2.24 (5.45) | 38 | −1.31 (8.79) |
| 36 | 406 | −2.26 (5.60) | 38 | −1.41 (9.46) |
| 40 | 398 | −2.38 (6.70) | 36 | −1.57 (9.69) |
| 44 | 388 | −2.04 (6.14) | 35 | −1.80 (9.67) |
| 48 | 382 | −1.85 (6.23) | 35 | −1.51 (9.58) |
| 52 | 366 | −1.71 (6.39) | 30 | −1.90 (10.03) |
| End of the OL Period | 531 | −1.57 (5.75) | 58 | −1.14 (7.76) |

Table 48 provides a summary of final total daily dose among initial treatment in Study B. The most common daily dose for topiramate in Study B was 25 mg.

TABLE 48

Summary of final total daily dose among initial treatment

| | 10 mg | 12.5 mg | 20 mg | 25 mg | 50 mg | 100 mg | Total |
|---|---|---|---|---|---|---|---|
| Amitriptyline | 19 | 1 | 1 | 21 | 1 | 1 | 43 |
| Topiramate | — | 2 | — | 33 | 29 | 6 | 70 |

As shown above, in the Study B long term safety study, atogepant led to a gradual weight reduction from week 4 to week 40 (2.11 kg reduction at week 40); the weight reduction then slightly decreased to −1.54 kg at week 52, and −1.42 at the end of the OL period. At the end of the OL period, the percentage reduction of weight was −1.57 for atogepant 60 mg, and −1.14 for topiramate.

The invention claimed is:

1. A method for the preventive treatment of migraine in a patient having migraine headaches, the method comprising administering to the patient 60 mg atogepant, or a pharmaceutically acceptable salt thereof, once daily for more than 12 weeks;
   wherein administration of atogepant is associated with a reduction in mean monthly migraine days, and wherein administration of atogepant is associated with a reduction from baseline in body weight.

2. The method of claim 1, wherein administration of atogepant results in a reduction in mean monthly migraine days of at least about 3.6 days.

3. The method of claim 1, wherein administration of atogepant results in a reduction in mean monthly migraine days of at least about 3.8 days.

4. The method of claim 1, wherein administration of atogepant results in a reduction in mean monthly migraine days of at least about 4.2 days.

5. The method of claim 1, wherein administration of atogepant results in at least 50% reduction in monthly migraine days.

6. The method of claim 1, wherein administration of atogepant results in a reduction in body weight from baseline of at least about 0.5 kg.

7. The method of claim 1, wherein administration of atogepant results in a reduction in body weight from baseline of at least about 0.8 kg.

8. The method of claim 1, wherein administration of atogepant results in a reduction in body weight from baseline of at least about 1.4 kg.

9. The method of claim 1, wherein at least about 22% of patients achieve a weight decrease of greater than about 5% relative to baseline.

10. The method of claim 1, wherein at least about 4.9% of patients achieve a weight loss of greater than 7% relative to baseline body weight.

* * * * *